(12) United States Patent
Baker, Jr. et al.

(10) Patent No.: US 11,083,788 B2
(45) Date of Patent: Aug. 10, 2021

(54) NANOEMULSION COMPOSITIONS FOR PREVENTING, SUPPRESSING OR ELIMINATING ALLERGIC AND INFLAMMATORY DISEASE

(71) Applicant: THE REGENTS OF THE UNIVERSITY OF MICHIGAN, Ann Arbor, MI (US)

(72) Inventors: James R. Baker, Jr., Ann Arbor, MI (US); Anna U. Bielinska, Ann Arbor, MI (US); Douglas Smith, Ann Arbor, MI (US); Paul E. Makidon, Ann Arbor, MI (US); Jessica J. O'Konek, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/517,916

(22) PCT Filed: Oct. 9, 2015

(86) PCT No.: PCT/US2015/054943
§ 371 (c)(1),
(2) Date: Apr. 7, 2017

(87) PCT Pub. No.: WO2016/057921
PCT Pub. Date: Apr. 14, 2016

(65) Prior Publication Data
US 2017/0246294 A1    Aug. 31, 2017

Related U.S. Application Data

(60) Provisional application No. 62/062,644, filed on Oct. 10, 2014.

(51) Int. Cl.
| | | |
|---|---|---|
| *A61K 39/35* | (2006.01) | |
| *A61K 9/107* | (2006.01) | |
| *A61K 9/00* | (2006.01) | |
| *A61K 47/22* | (2006.01) | |
| *A61K 47/44* | (2017.01) | |
| *A61K 47/26* | (2006.01) | |
| *A61K 9/14* | (2006.01) | |
| *A61K 39/29* | (2006.01) | |
| *C12N 7/00* | (2006.01) | |
| *A61K 39/00* | (2006.01) | |

(52) U.S. Cl.
CPC .......... *A61K 39/35* (2013.01); *A61K 9/0043* (2013.01); *A61K 9/1075* (2013.01); *A61K 9/143* (2013.01); *A61K 39/292* (2013.01); *A61K 47/22* (2013.01); *A61K 47/26* (2013.01); *A61K 47/44* (2013.01); *C12N 7/00* (2013.01); *A61K 2039/543* (2013.01); *A61K 2039/545* (2013.01); *A61K 2039/55505* (2013.01); *A61K 2039/55511* (2013.01); *A61K 2039/55566* (2013.01); *A61K 2039/57* (2013.01); *C12N 2730/10134* (2013.01)

(58) Field of Classification Search
None
See application file for complete search history.

(56) References Cited

U.S. PATENT DOCUMENTS

| | | |
|---|---|---|
| 3,854,480 A | 12/1974 | Zaffaroni |
| 4,452,775 A | 6/1984 | Kent |
| 4,596,556 A | 6/1986 | Morrow et al. |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,675,189 A | 6/1987 | Kent et al. |
| 4,895,452 A | 1/1990 | Yiournas et al. |
| 5,057,540 A | 10/1991 | Kensil et al. |
| 5,103,497 A | 4/1992 | Hicks |
| 5,133,974 A | 7/1992 | Paradissi et al. |
| 5,284,656 A | 2/1994 | Platz et al. |
| 5,407,686 A | 4/1995 | Patel et al. |
| 5,451,569 A | 9/1995 | Wong et al. |
| 5,510,104 A | 4/1996 | Allen |
| 5,547,677 A | 8/1996 | Wright |

(Continued)

FOREIGN PATENT DOCUMENTS

| | | |
|---|---|---|
| EP | 0468520 | 1/1992 |
| EP | 0362279 | 1/1995 |

(Continued)

OTHER PUBLICATIONS

Kuby Immunology, 4th Edition, Chapter 18, "Vaccines," pp. 449-465 (2001).*

(Continued)

*Primary Examiner* — Nora M Rooney
(74) *Attorney, Agent, or Firm* — Casimir Jones, S.C.; Melissa E. Karabinis

(57) ABSTRACT

The present invention provides methods and compositions for the stimulation of immune responses and for treating or preventing allergic disease and responses and inflammatory disease and responses. In particular, the present invention provides nanoemulsion compositions and methods of using the same for the induction of immune responses that prevent or treat allergic disease by reducing allergic response. Compositions and methods of the invention find use in, among other things, clinical (e.g. therapeutic and preventative medicine (e.g., vaccination)) and research applications.

11 Claims, 9 Drawing Sheets

(56) References Cited

U.S. PATENT DOCUMENTS

| | | | |
|---|---|---|---|
| 5,549,901 A | 8/1996 | Wright | |
| 5,618,840 A | 4/1997 | Wright | |
| 5,700,679 A | 12/1997 | Wright | |
| 5,736,152 A | 4/1998 | Dunn | |
| 5,985,309 A | 11/1999 | Edwards et al. | |
| 5,993,412 A | 11/1999 | Deily et al. | |
| 5,997,848 A | 12/1999 | Patton et al. | |
| 6,015,832 A | 1/2000 | Baker, Jr. et al. | |
| 6,051,256 A | 4/2000 | Platz et al. | |
| RE37,053 E | 2/2001 | Hanes et al. | |
| 6,294,204 B1 | 9/2001 | Rossling et al. | |
| 6,423,344 B1 | 7/2002 | Platz et al. | |
| 6,436,443 B2 | 8/2002 | Edwards et al. | |
| 6,447,753 B2 | 9/2002 | Edwards et al. | |
| 6,503,480 B1 | 1/2003 | Edwards et al. | |
| 6,506,803 B1 | 1/2003 | Baker, Jr. et al. | |
| 6,518,239 B1 | 2/2003 | Kuo et al. | |
| 6,559,189 B2 | 5/2003 | Baker, Jr. et al. | |
| 6,592,904 B2 | 7/2003 | Platz et al. | |
| 6,635,283 B2 | 10/2003 | Edwards et al. | |
| 6,635,676 B2 | 10/2003 | Edwards et al. | |
| 6,651,655 B1 | 11/2003 | Licalsi et al. | |
| 8,889,117 B2 * | 11/2014 | Mellman | A61K 39/00 424/85.1 |
| 2002/0045667 A1 | 4/2002 | Baker, Jr. et al. | |
| 2004/0043041 A1 | 3/2004 | Baker, Jr. et al. | |
| 2005/0208083 A1 | 9/2005 | Annis | |
| 2005/0238660 A1 | 10/2005 | Babiuk et al. | |
| 2005/0281843 A1 | 12/2005 | Singh et al. | |
| 2006/0251684 A1 | 11/2006 | Annis et al. | |
| 2007/0036831 A1 | 2/2007 | Baker et al. | |
| 2012/0107349 A1 * | 5/2012 | Baker, Jr. | A61K 9/1075 424/203.1 |
| 2013/0273113 A1 | 10/2013 | Baker et al. | |

FOREIGN PATENT DOCUMENTS

| | | | |
|---|---|---|---|
| EP | 0517565 | 10/2000 | |
| WO | WO 92/19265 | 11/1992 | |
| WO | WO 93/13202 | 7/1993 | |
| WO | WO 94/00153 | 1/1994 | |
| WO | WO 95/17210 | 6/1995 | |
| WO | WO 96/02555 | 2/1996 | |
| WO | WO 96/11711 | 4/1996 | |
| WO | WO 96/33739 | 10/1996 | |
| WO | WO 97/48440 | 12/1997 | |
| WO | WO 98/16247 | 4/1998 | |
| WO | WO 98/20734 | 5/1998 | |
| WO | WO 98/28037 | 7/1998 | |
| WO | WO 98/56414 | 12/1998 | |
| WO | WO 99/10008 | 3/1999 | |
| WO | WO 99/11241 | 3/1999 | |
| WO | WO 99/12565 | 3/1999 | |
| WO | WO 99/27961 | 6/1999 | |
| WO | WO 2010/033274 * | 3/2010 | A61K 39/00 |
| WO | WO 2013/036907 | 3/2013 | |
| WO | WO 2013/163176 * | 10/2013 | A61K 39/00 |

OTHER PUBLICATIONS

Kurucz et al. 'Current Animal Models of Bronchial Asthma.' Curr. Pharm. Des. 12:3175-3194, 2006.*
Mukherjee et al. 'Allergic Asthma: Influence of Genetic and Environmental Factors.' J. Biol. Chem. 286(38):32883-32889, 2011.*
O'Koneck et al. 'Nanoemulsion adjuvant-driven redirection of TH2 immunity inhibits allergic reactions in murine models of peanut allergy.' j. Allerg. Clin. Immuno . . . 141(6):2121-2131, 2018.*
Turcanu et al. 'Characterization of lymphocyte responses to peanuts in normal children, peanut-allergic children, and allergic children who acquired tolerance to peanuts.' J. Clin. INvest 111(7): 1065-1072, 2003.*

Adjei et al., Bioavailability of leuprolide following intratracheal administration to beagle dogs. Int. J. Pharmaceutics 1990; 61(1-2):135-144.
Adjei, et al., Pulmonary delivery of peptide drugs: effect of particle size on bioavailability of leuprolide acetate in healthy male volunteers. Pharm Res. Jun. 1990;7(6):565-9.
Braquet et al., Effect of endothelin-1 on blood pressure and bronchopulmonary system of the guinea pig. J Cardiovasc Pharmacol. 1989;13 Suppl 5:S143-6.
Brazolot-Millan et al., CpG DNA can induce strong Th1 humoral and cell-mediated immune responses against hepatitis B surface antigen in young mice. Proc Natl Acad Sci U S A. Dec. 22, 1998;95(26):15553-8.
Brown et al., Differential diagnosis of *Bacillus cereus*, *Bacillus anthracis*, and *Bacillus cereus* var. *mycoides*. J Bacteriol. May 1958;75(5):499-509.
Burdon et al., Experimental infection of mice with Bacillus cereus: studies of pathogenesis and pathologic changes. J Infect Dis. Oct. 1967;117(4):307-16.
Burdon et al., On the differentiation of anthrax bacilli from Bacillus cereus. J Infect Dis. Sep.-Oct. 1960;107:224-34.
Butterton et al., Development of a germfree mouse model of Vibrio cholerae infection. Infect Immun. Oct. 1996;64(10):4373-7.
Carter et al., The route of enteric infection in normal mice. J Exp Med. May 1, 1974;139(5):1189-203.
Castleman et al., Pathogenesis of bronchiolitis and pneumonia induced in neonatal and weanling rats by parainfluenza (Sendai) virus. Am J Pathol. Nov. 1987;129(2):277-86.
Castleman, Respiratory tract lesions in weanling outbred rats infected with Sendai virus. Am J Vet Res. Jun. 1983;44(6):1024-31.
Collins et al., Comparative immunogenicity of heat-killed and living oral *Salmonella* vaccines. Infect Immun. Oct. 1972;6(4):451-8.
Collins, Salmonellosis in orally infected specific pathogen-free C57B1 mice. Infect Immun. Feb. 1972;5(2):191-8.
Debs et al., Lung-specific delivery of cytokines induces sustained pulmonary and systemic immunomodulation in rats. J Immunol. May 15, 1988;140(10):3482-8.
Donovan et al., Prevention of murine influenza A virus pneumonitis by surfactant nano-emulsions. Antivir Chem Chemother. Jan. 2000;11(1):41-9.
Finkelstein et al., Pathogenesis Experimental Cholera in Infant Rabbits. I. Observations on the Intraintestinal Infection and Experimental Cholera Produced With Cell-Free Products. J Infect Dis. Jun. 1964;114:203-16.
Formal et al., Experimental Shigella infections. VI. Role of the small intestine in an experimental infection in guinea pigs. J Bacteriol. Jan. 1963;85:119-25.
Freter, Experimental enteric Shigella and Vibrio infections in mice and guinea pigs. J Exp Med. Sep. 1, 1956;104(3):411-8.
Freter, The fatal enteric cholera infection in the guinea pig, achieved by inhibition of normal enteric flora. J Infect Dis. Jul.-Aug. 1955;97(1):57-65.
Graham, New approaches to vaccine adjuvants: inhibiting the inhibitor. PLoS Med. Jan. 2006;3(1):e57.
Halvorson, Biochemistry of spores of aerobic bacilli with special reference to germination. Bacteriol Rev. Jun. 1957;21(2):112-31.
Hamouda et al., A novel surfactant nanoemulsion with broad-spectrum sporicidal activity against *Bacillus* species. J Infect Dis. Dec. 1999;180(6):1939-49.
Hamouda et al., Antimicrobial mechanism of action of surfactant lipid preparations in enteric Gram-negative bacilli. J Appl Microbiol. Sep. 2000;89(3):397-403.
Hills, Chemical factors in the germination of spore-bearing aerobes: observations on the influence of species, strain and conditions of growth. J Gen Microbiol. Jan. 1950;4(1):38-47.
Hubbard, et al. (1989) Annals of Internal Medicine, vol. III, pp. 206-212.
Illum et al., Hyaluronic acid ester microspheres as a nasal delivery system for insulin. Journal of Controlled Release 1994; 29(1-2):133-141.
Jacoby et al., Sendai viral pneumonia in aged BALB/c mice. Exp Gerontol. Jan.-Feb. 1994;29(1):89-100.

(56) References Cited

OTHER PUBLICATIONS

Johnson et al., Age-dependent resistance to viral encephalitis: studies of infections due to Sindbis virus in mice. J Infect Dis. Mar. 1972;125(3):257-62.
Johnson, Virus Invasion of the Central Nervous System: A Study of Sindbis Virus Infection in the Mouse Using Fluorescent Antibody. Am J Pathol. Jun. 1965;46:929-43.
Kensil et al., Separation and characterization of saponins with adjuvant activity from Quillaja saponaria Molina cortex. J Immunol. Jan. 15, 1991;146(2):431-7.
Kensil, Saponins as vaccine adjuvants. Crit Rev Ther Drug Carrier Syst. 1996;13(1-2):1-55.
Labrec et al., Epithelial Cell Penetration as an Essential Step in the Pathogenesis of Bacillary Dysentery. J Bacteriol. Nov. 1964;88(5):1503-18.
Lacaille-Dubois and Wagner (1996) Phytomedicine vol. 2 pp. 363-386.
Levine et al., New knowledge on pathogenesis of bacterial enteric infections as applied to vaccine development. Microbiol Rev. Dec. 1983;47(4):510-50.
Massion et al., Parainfluenza (Sendai) virus infects ciliated cells and secretory cells but not basal cells of rat tracheal epithelium. Am J Respir Cell Mol Biol. Oct. 1993;9(4):361-70.
McCluskie et al., CpG DNA is a potent enhancer of systemic and mucosal immune responses against hepatitis B surface antigen with intranasal administration to mice. J Immunol. Nov. 1, 1998;161(9):4463-6.
Mims et al., Parainfluenza virus Sendai infection in macrophages, ependyma, choroid plexus, vascular endothelium and respiratory tract of mice. Am J Pathol. Mar. 1973;70(3):315-28.
Mutsch et al., Use of the inactivated intranasal influenza vaccine and the risk of Bell's palsy in Switzerland. N Engl J Med. Feb. 26, 2004;350(9):896-903.

Naughton et al., A rat model of infection by *Salmonella typhimurium* or Salm. enteritidis. J Appl Bacteriol. Dec. 1996;81(6):651-6.
O'Konek et al., Modulation of existing Th2 immune responses with a mucosal nanoemulsion-based vaccine, poster presented at Keystone Conference Oct. 8-13, 2014, Seattle, WA, 1 page.
Sandusky et al., An evaluation of aureomycin and chloromycetin in experimental Clostridium welchii infection. Surgery. Oct. 1950;28(4):632-41.
Smith et al., Pulmonary deposition and clearance of aerosolized alpha-1-proteinase inhibitor administered to dogs and to sheep. J Clin Invest. Oct. 1989;84(4):1145-54.
Stevens et al., Comparison of clindamycin, rifampin, tetracycline, metronidazole, and penicillin for efficacy in prevention of experimental gas gangrene due to Clostridium perfringens. J Infect Dis. Feb. 1987;155(2):220-8.
Stevens et al., Comparison of single and combination antimicrobial agents for prevention of experimental gas gangrene caused by Clostridium perfringens. Antimicrob Agents Chemother. Feb. 1987;31(2):312-6.
Takeuchi et al., Experimental bacillary dysentery. An electron microscopic study of the response of the intestinal mucosa to bacterial invasion. Am J Pathol. Dec. 1965;47(6):1011-44.
Yanagita, Biochemical aspects on the germination of conidiospores of Aspergillus niger. Arch Mikrobiol. 1957;26(4):329-44.
International Search Report and Written Opinion for PCT/US2015/054943, dated Jan. 8, 2016, 8 pages.
Oeswein et al., Aerosolization of Protein Pharamceuticals. Respiratory Drug Delivery II 1990;1:14-49.
Extended European Search Report for EP15849784.2, dated Apr. 30, 2018, 9 pages.
Baker, Jr. et al. "Nasal immunization with a novel nanoemulsion adjuvant modifies Th2-polarized immune responses" Journal of Allergry and Clinical Immunology, vol. 121, No. 3, Mar. 2008, p. 796.

* cited by examiner

A

B

NANOEMULSION COMPOSITIONS FOR PREVENTING, SUPPRESSING OR ELIMINATING ALLERGIC AND INFLAMMATORY DISEASE

STATEMENT REGARDING FEDERALLY SPONSORED RESEARCH OR DEVELOPMENT

This invention was made with government support under HHSN272200900031C awarded by the National Institutes of Health/National Institute of Allergy and Infectious Diseases. The government has certain rights in the invention.

FIELD OF THE INVENTION

The present invention provides methods and compositions for the stimulation of immune responses and for treating or preventing allergic disease and responses and inflammatory disease and responses. In particular, the present invention provides nanoemulsion compositions and methods of using the same for the induction of immune responses that prevent or treat allergic disease by reducing allergic response. Compositions and methods of the invention find use in, among other things, clinical (e.g. therapeutic and preventative medicine (e.g., vaccination)) and research applications.

BACKGROUND OF THE INVENTION

Allergic diseases such as allergic atopic dermatitis, urticarial, allergic rhinitis and respiratory allergies (e.g., pollen allergies), food allergies, and allergic asthma exist as serious health issues in the United States and in other countries.

Additionally, allergic reactions to substances such as pollens (hay fever) or other components of plants, cat fur and other animal hairs, dust including the house dust mite droppings it contains, insect poison, foods such as milk or nuts, or perfumes and other components of cosmetics are well known and a growing problem for increasing numbers of people.

Conventional treatment for allergies include medications such as steroids or other types of drugs that inhibit the release of inflammatory substances in mast cells. However, they have multiple drawbacks in that they often trigger a number of undesirable side effects, don't address the underlying immunological bases of the disease, and must be continually taken by a patient in order to provide a benefit. "Oral immunotherapy," a treatment for food allergy where allergen-inducing foods are fed to patients under controlled circumstances, has been able to desensitize some individuals to food antigens; however, this procedure involves frequent and prolonged oral intake of the offending food, has significant risk for severe adverse reactions and usually does not induce long-term oral tolerance to the food.

SUMMARY OF THE INVENTION

The present invention provides methods and compositions for the stimulation of immune responses and for treating or preventing allergic disease and responses and inflammatory disease and responses. In particular, the present invention provides nanoemulsion compositions and methods of using the same for the induction of immune responses that prevent or treat allergic disease by reducing allergic response. Compositions and methods of the invention find use in, among other things, clinical (e.g. therapeutic and preventative medicine (e.g., vaccination)) and research applications.

In one embodiment, the invention provides a method for treating an allergic disease in a subject comprising administering to the subject a therapeutically effective amount of a nanoemulsion-based vaccine. The invention is not limited to any particular allergic disease. Indeed, compositions and methods of the invention may be utilized to prevent and/or treat a variety of allergic diseases including but not limited to those described herein. In another embodiment, the invention provides a method for treating an inflammatory disease in a subject comprising administering to the subject a therapeutically effective amount of a nanoemulsion-based vaccine. The invention is not limited to any particular inflammatory disease. Indeed, compositions and methods of the invention may be utilized to prevent and/or treat a variety of inflammatory diseases including but not limited to those described herein. In one embodiment, the therapeutically effective amount of a nanoemulsion-based vaccine reduces an allergic immune response in the subject. The invention provides multiple benefits regarding the reduction of allergic immune responses in a subject. In one embodiment, a therapeutically effective amount of a nanoemulsion-based vaccine reduces the expression of Th2 type cytokines (e.g., IL-4, IL-5, IL-13) in the subject. In one embodiment, a therapeutically effective amount of a nanoemulsion-based vaccine reduces the expression of Th2 associated immunoglobulins (e.g., reduces the IgG1 titer) in the subject. In another embodiment, the therapeutically effective amount of a nanoemulsion-based vaccine modulates aberrant Th2 immune responses associated with the allergic disease. For example, in one embodiment, the therapeutically effective amount of a nanoemulsion-based vaccine increases Th1 associated immune responses in the subject and reduces Th2 associated immune responses in the subject. In one embodiment, the Th1 associated immune response is increased expression of IFN-gamma. In another embodiment, the Th1 associated immune response is increased expression of TNF-alpha. In yet another embodiment, the Th1 associated immune response is increased expression of IL-17. In still a further embodiment, the Th1 associated immune response is increased expression IgG2a and/or IgG2b. In one embodiment, a nanoemulsion-based vaccine increases expression of IFN-gamma, TNF-alpha, IL-17, IgG2a and/or IgG2b, while at the same time reduces expression of Th2 cytokines (e.g., IL-4, IL-5, and/or IL-13). In one embodiment, the administering the nanoemulsion-based vaccine comprises intranasal administration. The invention is not limited by the type of nanoemulsion based vaccine utilized. Indeed, any nanoemulsion based vaccine or composition described herein may be utilized.

In another embodiment of the invention, there is provided a method of generating an immune response in a host, including a human, comprising administering thereto an immunogenic nanoemulsion adjuvant of the present invention (e.g., independently and/or in combination with one or more antigenic (e.g., microbial pathogen (e.g., bacteria, viruses, etc.) protein, glycoprotein, lipoprotein, peptide, glycopeptide, lipopeptide, toxoid, carbohydrate, tumor-specific antigen))) components. In one embodiment, a host immune response attained via administration of a nanoemulsion adjuvant to a host subject is a humoral immune response. In another embodiment, a host immune response attained via administration of a nanoemulsion adjuvant to a host subject is a cell-mediated immune response.

The present invention is not limited by the type of antigenic component (e.g., pathogen, pathogen component, antigen, immunogen, etc.) that can be utilized with (e.g., combined with, co-administered, administered before or after, etc.) a nanoemulsion adjuvant (e.g., to be used as a nanoemulsion-based vaccine for the treatment of allergic disease). In one embodiment, the antigen/immunogen is selected from virus, bacteria, fungus and pathogen products derived from the virus, bacteria, or fungus. The present invention is not limited to a particular virus. A variety of viral immunogens are contemplated including, but not limited to, influenza A virus, avian influenza virus, H5N1 influenza virus, H1N1 influenza virus, West Nile virus, SARS virus, Marburg virus, Arenaviruses, Nipah virus, alphaviruses, filoviruses, herpes simplex virus I, herpes simplex virus II, *sendai* virus, *sindbis* virus, vaccinia virus, parvovirus, human immunodeficiency virus, hepatitis B virus, hepatitis C virus, hepatitis A virus, cytomegalovirus, human papilloma virus, picornavirus, hantavirus, junin virus, and ebola virus. The present invention is not limited to a particular bacteria. A variety of bacterial immunogens are contemplated including, but not limited to, *Bacillus cereus, Bacillus circulans* and *Bacillus megaterium, Bacillus anthracis*, bacterial of the genus *Brucella, Vibrio cholera, Coxiella burnetii, Francisella tularensis, Chlamydia psittaci, Ricinus communis, Rickettsia prowazekii*, bacteria of the genus *Salmonella, Cryptosporidium parvum, Burkholderia pseudomallei, Clostridium perfringens, Clostridium botulinum, Vibrio cholerae, Streptococcus pyogenes, Streptococcus agalactiae, Streptococcus pneumonia, Staphylococcus aureus, Neisseria gonorrhea, Haemophilus influenza, Escherichia coli, Salmonella typhimurium, Shigella dysenteriae, Proteus mirabilis, Pseudomonas aeruginosa, Yersinia pestis, Yersinia enterocolitica*, and *Yersinia pseudotuberculosis*. The present invention is also not limited to a particular fungus. A variety of fungal immunogens are contemplated including, but not limited to, *Candida* and *Aspergillus*.

In a preferred embodiment, a nanoemulsion composition (e.g., nanoemulsion based vaccine) provided herein skews an immune response toward a Th1 type response. In some embodiments, a nanoemulsion composition (e.g., nanoemulsion based vaccine) provided herein provides a balanced Th1/Th2 response and/or polarization (e.g., an IgG subclass distribution and cytokine response indicative of a balanced Th1/Th2 response) when administered to a subject. Thus, a variety of immune responses may be generated and/or measured in a subject administered a nanoemulsion composition (e.g., nanoemulsion based vaccine) of the present invention including, but not limited to, activation, proliferation and/or differentiation of cells of the immune system (e.g., B cells, T cells, dendritic cells, antigen presenting cells (APCs), macrophages, natural killer (NK) cells, etc.); up-regulated or down-regulated expression of markers and/or cytokines; stimulation of IgA, IgM, IgE, and/or IgG titers; splenomegaly (e.g., increased spleen cellularity); hyperplasia, mixed cellular infiltrates in various organs, and/or other responses (e.g., of cells) of the immune system that can be assessed with respect to immune stimulation known in the art.

In a preferred embodiment, administering a nanoemulsion composition (e.g., nanoemulsion based vaccine) comprises contacting a mucosal surface of the subject with the nanoemulsion composition. The present invention is not limited by the mucosal surface contacted. In some preferred embodiments, the mucosal surface comprises nasal mucosa. In some embodiments, the mucosal surface comprises vaginal mucosa. In some embodiments, administrating comprises parenteral administration. The present invention is not limited by the route chosen for administration of a nanoemulsion composition (e.g., nanoemulsion based vaccine) provided. In some embodiments, inducing an immune response primes the immune system of a host to respond to (e.g., to produce a Th1 and/or Th1/Th2 balanced response (e.g., thereby providing protective immunity) one or more pathogens (e.g., *B. anthracis*, vaccinia virus, *C. botulinum, Y. pestis* and/or HIV, etc.) in the host subject (e.g., human or animal subject). In some embodiments, the immunity comprises systemic immunity. In some embodiments, the immunity comprises mucosal immunity. In some embodiments, the immune response comprises increased expression of IFN-γ and/or TNF-α in the subject. In some embodiments, the immune response comprises a systemic IgG response. In some embodiments, the immune response comprises a mucosal IgA response.

In some embodiments, the present invention provides an immunogenic composition for eliciting an immune response in a host, including a human, the composition comprising: (a) at least one antigen and/or immunogen; and (b) a nanoemulsion adjuvant. In some embodiments, the composition comprises an additional adjuvant (e.g., a second nanoemulsion adjuvant and/or a non-nanoemulsion adjuvant (e.g., CpG oligonucleotide, toxin, or other adjuvant described herein).

In yet another aspect of the invention, there is provided a method of modulating and/or inducing an immune response (e.g., toward and/or away from a Th1 and/or Th2 type response) in a subject (e.g., toward an antigen) comprising providing a host subject and a nanoemulsion composition (e.g., nanoemulsion based vaccine) of the invention, and administering the nanoemulsion composition to the host subject under conditions such that an immune response is induced and/or modulated in the host subject. In some embodiments, the host immune response is specific for the nanoemulsion adjuvant. In some embodiments, the host immune response comprises enhanced expression and/or activity of Th1 type cytokines (e.g., IL-2, IL-12, IFN-γ and/or TNF-α, etc.) while concurrently lacking enhanced expression and/or activity of Th2 type cytokines (e.g., IL-4, IL-5, IL-10, etc.). In some embodiments, the host immune response comprises reduced expression of Th2 type cytokines (e.g., IL-4, IL-5, IL-10, etc.) while concurrently lacking enhanced expression and/or activity of Th1 type cytokines (e.g., (e.g., IL-2, IL-12, IFN-γ and/or TNF-α, etc.). In some embodiments, a nanoemulsion composition administered to a subject induces expression and/or activity of Th1-type cytokines that increases to a greater extent than the level of expression and/or activity of Th2-type cytokines. For example, in some embodiments, a subject administered a nanoemulsion composition induces a greater than 2 fold, 3 fold, greater than 5 fold, greater than 10 fold, greater than 20 fold, greater than 25 fold, greater than 30 fold or more enhanced expression of Th1 type cytokines (e.g., IL-2, IL-12, IFN-γ and/or TNF-α). In some embodiments, a subject administered a nanoemulsion composition induces enhanced expression of Th1 type cytokines (e.g., IL-2, IL-12, IFN-γ and/or TNF-α) and decreased expression of Th2 type cytokines (e.g., IL-4, IL-5, and/or IL-10). In some embodiments, the host immune response comprises enhanced IL-17 cytokine expression and/or activity. In some embodiments, the host immune response is specific for an antigen co-administered with the nanoemulsion composition. In some embodiments, administering the nanoemulsion composition to the host subject (e.g., in combination with an antigenic component (e.g., whole cell pathogen or component thereof)) induces and/or enhances the generation of one or more antibodies in the subject (e.g., IgG and/or IgA antibodies) that are not generated or generated at low levels in the host subject in the absence of administration of the nanoemulsion composition. As described herein, antigens and/or immunogens that may be included in an immunogenic nanoemulsion adjuvant composition of the present invention, include, but are not limited to, microbial pathogens, bacteria, viruses, proteins, glycoproteins lipoproteins, peptides, glycopeptides, lipopeptides, toxoids, carbohydrates, and tumor-specific antigens. In some embodiments, mixtures of two or more antigens/immunogens may be utilized.

In some embodiments, a nanoemulsion composition is formulated to comprise between 0.1 and 500 µg of a protein antigen (e.g., derived or isolated from a pathogen and/or a recombinant form of an immunogenic pathogen component). However, the present invention is not limited to this amount of protein antigen. For example, in some embodiments, more than 500 µg of protein antigen is present in an adjuvant for administration to a subject. In some embodiments, less than 0.1 µg of protein antigen is present in an adjuvant for administration to a subject. In one embodiment, the protein antigen is a known allergen (e.g., a peanut antigen, allergen described herein or other type of protein allergen known in the art).

In some embodiments, a pathogen (e.g., a virus) is inactivated by the nanoemulsion and is then administered to the subject under conditions such that between about 10 and $10^7$ pfu (e.g., about $10^2$, $10^3$, $10^4$, $10^5$, or $10^6$ pfu) of the inactivated pathogen is present in a dose administered to the subject. However, the present invention is not limited to this amount of pathogen present in a nanoemulsion adjuvant administered. For example, in some embodiments, more than $10^7$ pfu of the inactivated pathogen (e.g., $10^8$ pfu, $10^9$ pfu, or more) is present in a dose administered to the subject.

In one embodiment, a composition comprising a 10% nanoemulsion solution is utilized (e.g., in a nanoemulsion based vaccine). However, the present invention is not limited to this amount (e.g., percentage) of nanoemusion. For example, in some embodiments, a composition comprises less than 10% nanoemulsion (e.g., 9%, 8%, 7%, 6%, 5%, 4%, 3%, 2%, 1%, 0.5% or less). In some embodiments, a composition comprises more than 10% nanoemulsion (e.g., 15%, 20%, 25%, 30%, 35%, 40%. 45%, 50%, 60%, 70% or more). In some embodiments, a nanoemulsion utilized is any of the nanoemulsions described herein. In one embodiment, the nanoemulsion comprises oil, water, surfactant (e.g., polysorbate surfactant), alcohol (e.g., ethanol), and a cationic compound (e.g., cationic halogen containing compound (e.g., cetylpyridinium chloride (CPC))). In one embodiment, an immune responses resulting from administration of a nanoemulsion (e.g., individually and/or in combination with immunogenic components) prevents a subject from displaying signs or symptoms of allergic disease, or treats signs, symptoms or the underlying etiology of allergic disease.

In one embodiment, a nanoemulsion composition further comprises one or more additional adjuvants. The present invention is not limited by the type of additional adjuvant utilized. In some embodiments, the additional adjuvant is a CpG oligonucleotide. In some embodiments, the additional adjuvant is monophosphoryl lipid A. A number of other adjuvants that find use in the present invention are described herein. In some embodiments, the subject is a human.

DESCRIPTION OF THE DRAWING

The following figures form part of the present specification and are included to further demonstrate certain aspects and embodiments of the present invention. The invention may be better understood by reference to one or more of these figures in combination with the description of specific embodiments presented herein.

DEFINITIONS

Figure 1:
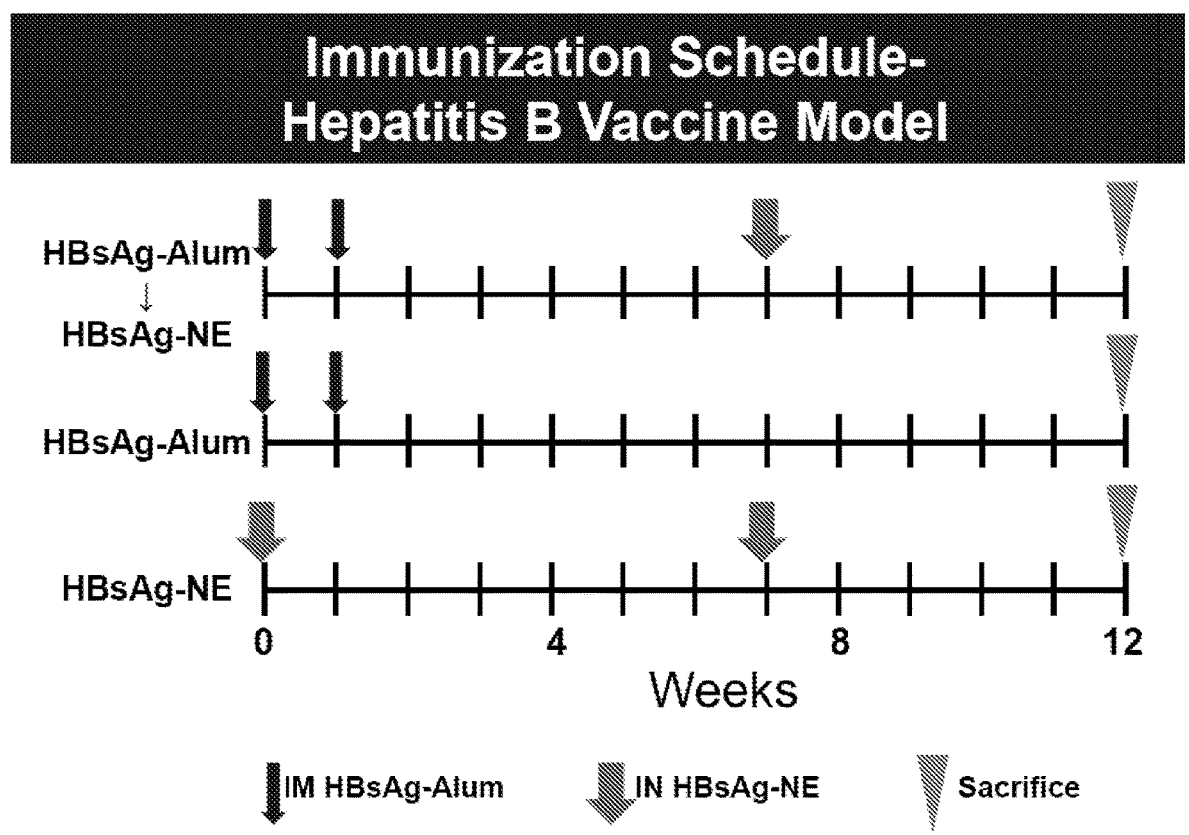
FIG. 1 shows an immunization schedule developed in order to induce a Th2 polarized immune response directed at hepatitis B surface antigen (HBsAg) and modulate that established immune response with a NE adjuvanted HBsAg vaccine.

To facilitate an understanding of the present invention, a number of terms and phrases are defined below:

As used herein, the term "microorganism" refers to any species or type of microorganism, including but not limited to, bacteria, viruses, archaea, fungi, protozoans, *mycoplasma*, prions, and parasitic organisms. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism.

As used herein the term "pathogen," and grammatical equivalents, refers to an organism (e.g., biological agent), including microorganisms, that causes a disease state (e.g., infection, pathologic condition, disease, etc.) in another organism (e.g., animals and plants) by directly infecting the other organism, or by producing agents that causes disease in another organism (e.g., bacteria that produce pathogenic toxins and the like). "Pathogens" include, but are not limited to, viruses, bacteria, archaea, fungi, protozoans, *mycoplasma*, prions, and parasitic organisms.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc.

As used herein, the term "fungi" is used in reference to eukaryotic organisms such as molds and yeasts, including dimorphic fungi.

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms (e.g., diarrhea, nausea, fever, pain, blisters, boils, rash, hyper-immune responses, hyper-sensitivity, immune suppression, inflammation, etc.) that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a virus or bacteria)), may be responsive to environmental factors (e.g., allergens, malnutrition, industrial hazards, and/or climate), may be responsive to an inherent defect of the organism (e.g., genetic anomalies) or to combinations of these and other factors.

The terms "host" or "subject," as used herein, refer to an individual to be treated by (e.g., administered) the compositions and methods of the present invention. Subjects include, but are not limited to, mammals (e.g., murines, simians, equines, bovines, porcines, canines, felines, and the like), and most preferably includes humans. In the context of the invention, the term "subject" generally refers to an individual who will be administered or who has been administered one or more compositions of the present invention (e.g., a composition for inducing an immune response).

As used herein, the terms "inactivating," "inactivation" and grammatical equivalents, when used in reference to a microorganism (e.g., a pathogen (e.g., a bacterium or a virus)), refer to the killing, elimination, neutralization and/or reducing of the capacity of the microorganism (e.g., a pathogen (e.g., a bacterium or a virus)) to infect and/or cause a pathological response and/or disease in a host.

As used herein, the term "fusigenic" is intended to refer to an emulsion that is capable of fusing with the membrane of a microbial agent (e.g., a bacterium or bacterial spore). Specific examples of fusigenic emulsions are described herein.

As used herein, the term "lysogenic" refers to an emulsion (e.g., a nanoemulsion) that is capable of disrupting the membrane of a microbial agent (e.g., a virus (e.g., viral envelope) or a bacterium or bacterial spore). In preferred embodiments of the present invention, the presence of a lysogenic and a fusigenic agent in the same composition produces an enhanced inactivating effect compared to either agent alone. Methods and compositions (e.g., for inducing an immune response (e.g., used as a vaccine) using this improved antimicrobial composition are described in detail herein.

The term "emulsion," as used herein, includes classic oil-in-water or water in oil dispersions or droplets, as well as other lipid structures that can form as a result of hydrophobic forces that drive apolar residues (e.g., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. Similarly, the term "nanoemulsion," as used herein, refers to oil-in-water dispersions comprising small lipid structures. For example, in some embodiments, the nanoemulsions comprise an oil phase having droplets with a mean particle size of approximately 0.1 to 5 microns (e.g., about 150, 200, 250, 300, 350, 400, 450, 500 nm or larger in diameter), although smaller and larger particle sizes are contemplated. The terms "emulsion" and "nanoemulsion" are often used herein, interchangeably, to refer to the nanoemulsions of the present invention.

As used herein, the terms "contact," "contacted," "expose," and "exposed," when used in reference to a nanoemulsion and a live microorganism, refer to bringing one or more nanoemulsions into contact with a microorganism (e.g., a pathogen) such that the nanoemulsion inactivates the microorganism or pathogenic agent, if present. The present invention is not limited by the amount or type of nanoemulsion used for microorganism inactivation. A variety of nanoemulsion that find use in the present invention are described herein and elsewhere (e.g., nanoemulsions described in U.S. Pat. Apps. 20020045667 and 20040043041, and U.S. Pat. Nos. 6,015,832, 6,506,803, 6,635,676, and 6,559,189, each of which is incorporated herein by reference in its entirety for all purposes). Ratios and amounts of nanoemulsion (e.g., sufficient for inactivating the microorganism (e.g., virus inactivation)) and microorganisms (e.g., sufficient to provide an antigenic composition (e.g., a composition capable of inducing an immune response)) are contemplated in the present invention including, but not limited to, those described herein.

The term "surfactant" refers to any molecule having both a polar head group, which energetically prefers solvation by water, and a hydrophobic tail that is not well solvated by water. The term "cationic surfactant" refers to a surfactant with a cationic head group. The term "anionic surfactant" refers to a surfactant with an anionic head group.

The terms "Hydrophile-Lipophile Balance Index Number" and "HLB Index Number" refer to an index for correlating the chemical structure of surfactant molecules with their surface activity. The HLB Index Number may be calculated by a variety of empirical formulas as described, for example, by Meyers, (See, e.g., Meyers, *Surfactant Science and Technology*, VCH Publishers Inc., New York, pp. 231-245 (1992)), incorporated herein by reference. As used herein where appropriate, the HLB Index Number of a surfactant is the HLB Index Number assigned to that surfactant in McCutcheon's Volume 1: Emulsifiers and Detergents North American Edition, 1996 (incorporated herein by reference). The HLB Index Number ranges from 0 to about 70 or more for commercial surfactants. Hydrophilic surfactants with high solubility in water and solubilizing properties are at the high end of the scale, while surfactants with low solubility in water that are good solubilizers of water in oils are at the low end of the scale.

As used herein the term "interaction enhancers" refers to compounds that act to enhance the interaction of an emulsion with a microorganism (e.g., with a cell wall of a bacteria (e.g., a Gram negative bacteria) or with a viral envelope (e.g., Vaccinia virus envelope)). Contemplated interaction enhancers include, but are not limited to, chelating agents (e.g., ethylenediaminetetraacetic acid (EDTA), ethylenebis (oxyethylenenitrilo)tetraacetic acid (EGTA), and the like) and certain biological agents (e.g., bovine serum albumin (BSA) and the like).

The terms "buffer" or "buffering agents" refer to materials, that when added to a solution, cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution.

The terms "chelator" or "chelating agent" refer to any materials having more than one atom with a lone pair of electrons that are available to bond to a metal ion.

The term "solution" refers to an aqueous or non-aqueous mixture.

As used herein, the term "a composition for inducing an immune response" refers to a composition that, once administered to a subject (e.g., once, twice, three times or more (e.g., separated by weeks, months or years)), stimulates, generates and/or elicits an immune response in the subject (e.g., modulating an existing immune response (e.g., an allergic immune response) and/or resulting in total or partial immunity to a microorganism (e.g., pathogen) capable of causing disease). In preferred embodiments of the invention, the composition comprises a nanoemulsion and an immunogen. In further preferred embodiments, the composition comprising a nanoemulsion and an immunogen comprises one or more other compounds or agents including, but not limited to, therapeutic agents, physiologically tolerable liquids, gels, carriers, diluents, adjuvants, excipients, salicylates, steroids, immunosuppressants, immunostimulants, antibodies, cytokines, antibiotics, binders, fillers, preservatives, stabilizing agents, emulsifiers, and/or buffers. An immune response may be an innate (e.g., a non-specific) immune response or a learned (e.g., acquired) immune response (e.g. that decreases the infectivity, morbidity, or onset of mortality in a subject (e.g., caused by exposure to a pathogenic microorganism) or that prevents infectivity, morbidity, or onset of mortality in a subject (e.g., caused by exposure to a pathogenic microorganism)). Thus, in some preferred embodiments, a composition comprising a nanoemulsion and an immunogen is administered to a subject as a vaccine (e.g., to prevent or attenuate a disease (e.g., allergic disease (e.g., by providing to the subject total or partial immunity against the disease or the total or partial attenuation (e.g., suppression) of a sign, symptom or condition of the disease (e.g., sign, symptom or condition of an allergic disease)))).

As used herein, the term "adjuvant" refers to any substance that can stimulate an immune response (e.g., a mucosal immune response). Some adjuvants can cause activation of a cell of the immune system (e.g., an adjuvant can cause an immune cell to produce and secrete a cytokine). Examples of adjuvants that can cause activation of a cell of the immune system include, but are not limited to, the nanoemulsion formulations described herein, saponins purified from the bark of the *Q. saponaria* tree, such as QS21 (a glycolipid that elutes in the 21st peak with HPLC fractionation; Aquila Biopharmaceuticals, Inc., Worcester, Mass.); poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.). Traditional adjuvants are well known in the art and include, for example, aluminum phosphate or hydroxide salts ("alum"). In some embodiments, compositions of the present invention (e.g., comprising HIV or an immunogenic epitope thereof (e.g., gp120)) are administered with one or more adjuvants (e.g., to skew the immune response towards a Th1 and/or Th2 type response).

As used herein, the term "an amount effective to induce an immune response" (e.g., of a composition for inducing an immune response), refers to the dosage level required (e.g., when administered to a subject) to stimulate, generate and/or elicit an immune response in the subject. An effective amount can be administered in one or more administrations (e.g., via the same or different route), applications or dosages and is not intended to be limited to a particular formulation or administration route. Accordingly, a "therapeutically effective amount" (e.g., of a composition for inducing an immune response), refers to the dosage level or amount of a composition required (e.g., when administered to a subject) to stimulate, generate and/or elicit a therapeutic benefit in a subject. An therapeutically effective amount can be administered in one or more administrations (e.g., via the same or different route), applications or dosages and is not intended to be limited to a particular formulation or administration route.

As used herein, the term "under conditions such that said subject generates an immune response" refers to any qualitative or quantitative induction, generation, and/or stimulation of an immune response (e.g., innate or acquired).

A used herein, the term "immune response" refers to a response by the immune system of a subject. For example, immune responses include, but are not limited to, a detectable alteration (e.g., increase) in Toll-like receptor (TLR) activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

As used herein, the terms "toll receptors" and "TLRs" refer to a class of receptors (e.g., TLR1, TLR2, TLR3, TLR4, TLR5, TLR6, TLR7, TLR8, TLR9, TLRT0, TLR 11) that recognize special patterns of pathogens, termed pathogen-associated molecular patterns (See, e.g., Janeway and Medzhitov, (2002) Annu. Rev. Immunol. 20, 197-216). These receptors are expressed in innate immune cells (e.g., neutrophils, monocytes, macrophages, dendritic cells) and in other types of cells such as endothelial cells. Their ligands include bacterial products such as LPS, peptidoglycans, lipopeptides, and CpG DNA. TLRs are receptors that bind to exogenous ligands and mediate innate immune responses leading to the elimination of invading microbes. The TLR-triggered signaling pathway leads to activation of transcription factors including NFkB, which is important for the induced expression of proinflammatory cytokines and chemokines. TLRs also interact with each other. For example, TLR2 can form functional heterodimers with TLR1 or TLR6. The TLR2/1 dimer has different ligand binding profile than the TLR2/6 dimer (Ozinsky et al., 2000). In some embodiments, a nanoemulsion adjuvant activates cell signaling through a TLR (e.g., TLR2 and/or TLR4). Thus, methods described herein include a nanoemulsion adjuvant composition (e.g., composition comprising NE adjuvant optionally combined with one or more immunogens (e.g., proteins and/or NE adjuvant inactivated pathogen (e.g., a virus (e.g., VV)))) that when administered to a subject, activates one or more TLRs and stimulates an immune response (e.g., innate and/or adaptive/acquired immune response) in a subject. Such an adjuvant can activate TLRs (e.g., TLR2 and/or TLR4) by, for example, interacting with TLRs (e.g., NE adjuvant binding to TLRs) or activating any downstream cellular pathway that occurs upon binding of a ligand to a TLR. NE adjuvants described herein that activate TLRs can also enhance the availability or accessibility of any endogenous or naturally occurring ligand of TLRs. A NE adjuvant that activates one or more TLRs can alter transcription of genes, increase translation of mRNA or increase the activity of proteins that are involved in mediating TLR cellular processes. For example, NE adjuvants described herein that activate one or more TLRs (e.g., TLR2 and/or TLR4) can induce expression of one or more cytokines (e.g., IL-8, IL-12p40, and/or IL-23)

As used herein, the term "immunity" refers to protection from disease (e.g., preventing or attenuating (e.g., suppression) of a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired/adaptive (e.g., immune responses that are mediated by B and T cells following a previous exposure to antigen (e.g., that exhibit increased specificity and reactivity to the antigen)).

As used herein, the terms "immunogen" and "antigen" refer to an agent (e.g., a microorganism (e.g., bacterium, virus or fungus) and/or portion or component thereof (e.g., a protein antigen (e.g., gp120 or rPA))) that is capable of eliciting an immune response in a subject. In preferred embodiments, immunogens elicit immunity against the immunogen (e.g., microorganism (e.g., pathogen or a pathogen product)) when administered in combination with a nanoemulsion of the present invention.

As used herein, the term "pathogen product" refers to any component or product derived from a pathogen including, but not limited to, polypeptides, peptides, proteins, nucleic acids, membrane fractions, and polysaccharides.

As used herein, the term "enhanced immunity" refers to an increase in the level of adaptive and/or acquired immunity in a subject to a given immunogen (e.g., microorganism (e.g., pathogen)) following administration of a composition (e.g., composition for inducing an immune response of the present invention) relative to the level of adaptive and/or acquired immunity in a subject that has not been administered the composition (e.g., composition for inducing an immune response of the present invention).

As used herein, the terms "purified" or "to purify" refer to the removal of contaminants or undesired compounds from a sample or composition. As used herein, the term "substantially purified" refers to the removal of from about 70 to 90%, up to 100%, of the contaminants or undesired compounds from a sample or composition.

As used herein, the terms "administration" and "administering" refer to the act of giving a composition of the present invention (e.g., a composition for inducing an immune response (e.g., a composition comprising a nanoemulsion and an immunogen)) to a subject. Exemplary routes of administration to the human body include, but are not limited to, through the eyes (ophthalmic), mouth (oral), skin (transdermal), nose (nasal), lungs (inhalant), oral mucosa (buccal), ear, rectal, by injection (e.g., intravenously, subcutaneously, intraperitoneally, etc.), topically, and the like.

As used herein, the terms "co-administration" and "co-administering" refer to the administration of at least two agent(s) (e.g., a composition comprising a nanoemulsion and an immunogen and one or more other agents—e.g., an adjuvant) or therapies to a subject. In some embodiments, the co-administration of two or more agents or therapies is concurrent. In other embodiments, a first agent/therapy is administered prior to a second agent/therapy. In some embodiments, co-administration can be via the same or different route of administration. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent. In other embodiments, co-administration is preferable to elicit an immune response in a subject to two or more different immunogens (e.g., microorganisms (e.g., pathogens)) at or near the same time (e.g., when a subject is unlikely to be available for subsequent administration of a second, third, or more composition for inducing an immune response).

As used herein, the term "topically" refers to application of a compositions of the present invention (e.g., a composition comprising a nanoemulsion and an immunogen) to the surface of the skin and/or mucosal cells and tissues (e.g., alveolar, buccal, lingual, masticatory, vaginal or nasal mucosa, and other tissues and cells which line hollow organs or body cavities).

In some embodiments, the compositions of the present invention are administered in the form of topical emulsions, injectable compositions, ingestible solutions, and the like. When the route is topical, the form may be, for example, a spray (e.g., a nasal spray), a cream, or other viscous solution (e.g., a composition comprising a nanoemulsion and an immunogen in polyethylene glycol).

The terms "pharmaceutically acceptable" or "pharmacologically acceptable," as used herein, refer to compositions that do not substantially produce adverse reactions (e.g., toxic, allergic or immunological reactions) when administered to a subject.

As used herein, the term "pharmaceutically acceptable carrier" refers to any of the standard pharmaceutical carriers including, but not limited to, phosphate buffered saline solution, water, and various types of wetting agents (e.g., sodium lauryl sulfate), any and all solvents, dispersion media, coatings, sodium lauryl sulfate, isotonic and absorption delaying agents, disintrigrants (e.g., potato starch or sodium starch glycolate), polyethylethe glycol, and the like. The compositions also can include stabilizers and preservatives. Examples of carriers, stabilizers and adjuvants have been described and are known in the art (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a composition of the present invention that is physiologically tolerated in the target subject. "Salts" of the compositions of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compositions of the present invention are contemplated as being pharmaceutically acceptable. However, salts of acids and bases that are non-pharmaceutically acceptable may also find use, for example, in the preparation or purification of a pharmaceutically acceptable composition.

As used herein, the term "at risk for disease" refers to a subject that is predisposed to experiencing a particular disease. This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk (e.g., a subject may be "at risk for disease" simply by being exposed to and interacting with other people), nor is it intended that the present invention be limited to any particular disease.

"Nasal application", as used herein, means applied through the nose into the nasal or sinus passages or both. The application may, for example, be done by drops, sprays, mists, coatings or mixtures thereof applied to the nasal and sinus passages.

"Vaginal application", as used herein, means applied into or through the vagina so as to contact vaginal mucosa. The application may contact the urethra, cervix, fornix, uterus or other area surrounding the vagina. The application may, for example, be done by drops, sprays, mists, coatings, lubricants or mixtures thereof applied to the vagina or surrounding tissue.

As used herein, the term "kit" refers to any delivery system for delivering materials. In the context of immunogenic agents (e.g., compositions comprising a nanoemulsion and an immunogen), such delivery systems include systems that allow for the storage, transport, or delivery of immunogenic agents and/or supporting materials (e.g., written instructions for using the materials, etc.) from one location to another. For example, kits include one or more enclosures (e.g., boxes) containing the relevant immunogenic agents (e.g., nanoemulsions) and/or supporting materials. As used herein, the term "fragmented kit" refers to delivery systems comprising two or more separate containers that each contain a subportion of the total kit components. The containers may be delivered to the intended recipient together or separately. For example, a first container may contain a composition comprising a nanoemulsion and an immunogen for a particular use, while a second container contains a second agent (e.g., an antibiotic or spray applicator). Indeed, any delivery system comprising two or more separate containers that each contains a subportion of the total kit components are included in the term "fragmented kit." In contrast, a "combined kit" refers to a delivery system containing all of the components of an immunogenic agent needed for a particular use in a single container (e.g., in a single box housing each of the desired components). The term "kit" includes both fragmented and combined kits.

DETAILED DESCRIPTION OF THE INVENTION

Allergic disease, as well as inflammatory disease, are associated with aberrant immune responses.

For example, epithelial cells play an important role in orchestrating the inflammation of allergy and asthma through the release of multiple cytokines, including stem cell factor and several chemokines that attract eosinophils. T helper type 2 (Th2) cells orchestrate the inflammatory response in asthma through the release of IL-4 and IL-13 (which stimulate B cells to synthesize IgE), IL-5 (which is involved in eosinophilic inflammation), and IL-9 (which stimulates mast cell proliferation).

Th2 cells predominate in most patients with allergies and asthma and differentiate from uncommitted precursor T cells under the influence of IL-4. Th2 cells orchestrate allergic inflammation through the release of the Th2 cytokines IL-4, IL-5, IL-9, and IL-13. Th1 cells differentiate under the influence of IL-12 and IL-27 and suppress Th2 cells through the release of IFN-γ. Th17 cells differentiate under the influence of IL-6 and IL-23. Tregs normally suppress other Th cells through the release of TGF-β and IL-10 and may have impaired function in allergy asthma.

IL-4 plays a critical role in the differentiation of Th2 cells from uncommitted Th0 cells and may be important in initial sensitization to allergens. It is also important for isotype switching of B cells from producers of IgG to producers of IgE. IL-13 mimics IL-4 in inducing IgE secretion and causing structural changes in the airways but does not play a role in promoting Th2 cell differentiation. IL-13 has attracted particular attention as a therapeutic target for the treatment of asthma, as it not only induces airway hyperresponsiveness (AHR) in animal models of asthma but also produces several of the structural changes seen in chronic asthma, including goblet cell hyperplasia, airway smooth muscle proliferation, and subepithelial fibrosis. IL-13 induces inflammation through stimulating the expression of multiple chemokines, including CCL11 (also known as eotaxin) from structural cells in the airways, including epithelial cells. IL-13 induces AHR and mucus hypersecretion.

IL-9 overexpression in mice induces inflammation mediated by eosinophils, mucus hyperplasia, mastocytosis, AHR, and increased expression of other Th2 cytokines and IgE. IL-9 blockade inhibits pulmonary eosinophilia, mucus hypersecretion, and AHR after allergen challenge of sensitized mice. Asthmatic patients show increased expression of IL-9 and its receptor in the airways.

Accordingly, the present invention provides methods and compositions for the stimulation of immune responses and for treating or preventing allergic disease and responses and inflammatory disease and responses. In particular, the present invention provides nanoemulsion compositions and methods of using the same for the induction of immune responses that prevent or treat allergic disease by reducing allergic response. Compositions and methods of the invention find use in, among other things, clinical (e.g. therapeutic and preventative medicine (e.g., vaccination)) and research applications.

Th2 immune responses are characterized by the production of IgE antibodies and high levels of Th2 cytokines and are associated with inadequate protection against some pathogens as well as cancer, colitis, asthma and allergy. Most currently used vaccine adjuvants induce predominantly Th2 response. Immunotherapies that have been attempted to shift immune responses from Th2 to Th1 have generally required prolonged immunization protocols and have not induced long-lasting Th1 responses. Accordingly, experiments were performed during development of embodiments of the invention in order to assess the ability of various nanoemulsion adjuvants to modulate existing Th2 polarized immune responses (e.g., in the context of allergy, inflammatory disease and other Th2 mediated disease) and shift and/or skew the Th2 polarized response towards a balanced Th1/Th17/Th2 profile (e.g., in order to reduce or eliminate signs, symptoms or morbidity associated with Th2 mediated disease).

Nanoemulsions (NE) has previously been observed to induce robust IgA and IgG antibody responses and Th1/Th17 cellular immunity, resulting in protection against a variety of respiratory and mucosal infections. Due to the observation that IN immunization with NE could induce Th1 type immune response, while Th2 cytokine responses were only marginally altered (neither up or down in a vaccination scheme), it was tested whether NE could be used as a therapeutic vaccine in order to redirect existing Th2 polarized immunity towards a balanced Th1/Th17/Th2 profile in the context of allergic or inflammatory disease.

Experiments were conducted during development of embodiments of the invention in order to establish Th2 polarized immune responses in a mouse model of allergic disease. To this end, a first set of experiments was conducted and sought to determine whether an established Th2 immune response could be modulated into a less strong Th2 immune response and/or into a Th1 or a balanced Th1/Th2 type response. As shown in Example 1, a Th2 immune response was established by intramuscular immunization with alum-adjuvanted hepatitis B surface antigen (HBs), and a single subsequent IN immunization with NE-HBs resulted in increased Th1 associated immune responses (IFN-gamma, TNF-alpha, IgG2a, and IgG2b) and IL-17, while concurrently decreasing Th2 cytokines (IL-4 and IL-5) and IgG1 presence (See Example 1).

Next, a mouse model of allergic disease was tested. In particular, a mouse model of allergic hypersensitivity to ovalbumin was established and the ability of nanoemulsion based vaccine tested in order to determine if NE-based vaccine might also be able to modulate the robust Th2 mediated immune responses associated with allergic disease (e.g., allergic hyper-responsiveness/hyper-sensitivity).

As shown in Example 2, there were significant benefits achieved in a mouse model of allergic hypersensitivity to ovalbumin upon administration of a nanoemulsion vaccine described herein. In particular, mice that had been administered alum-adjuvanted OVA in order to establish a Th2 allergic immune response, and subsequently administered NE-based vaccine, displayed a significantly modulated Th2 polarized immune response characterized by a skewing toward a Th1 immune response, resulting in a balanced Th1/Th2 immune response (See Example 2, FIG. 5 and FIG. 6). The ability of the NE-based vaccine to alter the allergic, disease associated, robust Th2 immune responses was surprising as other trials described in the literature attempting to do so have failed. Yet, the data accumulated during experiments conducted during development of embodiments of the invention indicate the ability of intranasal immunization with NE-based vaccine to modulate the allergic response away from the disease associated Th2 response (characterized by robust expression of Th2 cytokines (IL-4 and IL-5) and IgG1) and toward a balanced Th1/Th2 response (characterized by reduced Th2 response and increased IFN-gamma, TNF-alpha, IgG2a, and IgG2b, and IL-17.

Accordingly, in a preferred embodiment, the invention provides a method for treating an allergic disease in a subject comprising administering to the subject a therapeutically effective amount of a nanoemulsion-based vaccine. In one embodiment, NE-based vaccines are used to modulate (e.g., reduce or skew away from) Th2 immune responses (e.g., underling allergic disease) and promote Th1/Th17 immunity (e.g., skew towards a Th1 type immune response and/or a more balanced Th1/Th2 immune response) as a therapeutic for allergic disease, inflammatory disease, or any other disease associated with Th2 immunity. The invention is not limited to any particular allergic disease. Indeed, compositions and methods of the invention may be utilized to prevent and/or treat a variety of allergic diseases including but not limited to asthma, respiratory allergy (e.g., pollen allergy), stinging insect allergy, allergic rhinitis (hay fever), food allergy, drug allergy, latex allergy, atopic dermatitis (eczema), or other allergic disease known in the art. In one embodiment, the invention provides methods of modulating existing Th2 immune responses with a mucosal nanoemulsion-based vaccine (e.g., vaccinate a subject against a certain allergy (e.g., a peanut allergy)). This means that nanoemulsion could be used to vaccinate people against allergies (e.g., peanut, etc). In another embodiment, the invention provides the ability to redirect Th2-polarized immune responses in a subject (e.g., in a subject with Th2 mediated disease) toward a Th1-type immune response (e.g., skew toward a Th1 type immune response and/or generate a more balanced Th1/Th2 type immune response) via exposing the subject to (e.g., nasally administering) a NE vaccine. In one embodiment, the invention provides a more effective benefit (e.g., more significantly reduced sign, symptom or cause of disease, or a longer lived reduction of sign, symptom or condition of disease) than the benefit attained with conventional allergy shots.

In some embodiments, administration (e.g., mucosal administration) of a nanoemulsion composition of the invention primes, enables and/or enhances induction of both humoral (e.g., development of specific antibodies) and cellular (e.g., cytotoxic T lymphocyte) immune responses (e.g., thereby ameliorating signs, symptoms or conditions of allergic disease). In some embodiments, a nanoemulsion composition of the present invention is used in a vaccine (e.g., as an immunostimulatory adjuvant (e.g., that elicits and/or enhances immune responses (e.g., innate and or adaptive immune responses) in a host administered the nanoemulsion adjuvant).

Furthermore, in some embodiments, a composition of the present invention (e.g., a composition comprising a NE adjuvant) induces (e.g., when administered to a subject) both systemic and mucosal immune responses (e.g., generates systemic and or mucosal immunity (e.g., thereby reducing or preventing signs, symptoms or conditions of allergic disease)). Thus, in some embodiments, administration of a composition of the present invention to a subject results in protection against an exposure to one or a plurality of allergens and/or allergic substances (e.g., peanut allergen, biting or stinging insect allergen, respiratory allergen, etc.).

In some embodiments, the present invention provides nanoemulsion adjuvant compositions that replace the use of other adjuvants (e.g., adjuvants that cause inflammation, morbidity, and/or adverse side reactions in a host administered the composition). For example, in some embodiments, a nanoemulsion adjuvant of the invention is utilized in an immunogenic composition (e.g., a vaccine) in place of a Th1-type adjuvant. In some embodiments, a nanoemulsion adjuvant of the invention provides, when administered to a host subject, an immune response (e.g., an innate, cell mediated, adaptive and/or acquired immune response) that is similar to, the same as, or greater than an immune response elicited by a conventional adjuvant compositions (e.g., cholera toxin, CpG oligonucleotide, alum, and/or other adjuvant described herein) without adverse and/or unwanted side-effects.

The present invention is not limited to any particular nanoemulsion, pathogen or allergen. Exemplary immunogenic compositions (e.g., vaccine compositions) and methods of administering the compositions are described in more detail below.

I. Nanoemulsions

Nanoemulsion compositions utilized in some embodiments of the present invention have demonstrated anti-pathogen effect. For example, nanoemulsion compositions have been shown to inactivate bacteria (both vegetative and spore forms), virus, and fungi. In some embodiments of the present invention, pathogens are inactivated by exposure to nanoemulsions before being administered to a subject (e.g., to induce an immune response (e.g., for use as a vaccine)). Nanoemulsion adjuvant compositions can be used to rapidly inactivate bacteria. In certain embodiments, the compositions are particularly effective at inactivating Gram positive bacteria. In preferred embodiments, the inactivation of bacteria occurs after about five to ten minutes. Thus, bacteria may be contacted with an emulsion and will be inactivated in a rapid and efficient manner. It is expected that the period of time between the contacting and inactivation may be as little as 5-10 minutes where the bacteria is directly exposed to the emulsion. However, it is understood that when nanoemulsions are employed in a therapeutic context and applied systemically, the inactivation may occur over a longer period of time including, but not limited to, 5, 10, 15, 20, 25 30, 60 minutes post application. Further, in additional embodiments, inactivation may take two, three, four, five or six hours to occur.

Nanoemulsion can also rapidly inactivate certain Gram negative bacteria for use in generating the vaccines of the present invention. In such methods, the bacteria inactivating emulsions are premixed with a compound that increases the interaction of the emulsion by the cell wall. The use of these enhancers in the vaccine compositions of the present invention is discussed herein below. It should be noted that certain emulsions (e.g., those comprising enhancers) are effective against certain Gram positive and negative bacteria.

Nanoemulsion can also be mixed with an allergen, allergenic substance or other material that causes an allergic response in a subject for use in generating a nanoemulsion composition of the present invention. In such methods, an allergen, allergenic substance or other material that causes an allergic response is mixed with a nanoemulsion described herein. Optionally, other components described herein are mixed into the nanoemulsion composition.

Nanoemulsion adjuvants can also be utilized as anti-sporicidals. Without being bound to any theory (an understanding of the mechanism is not necessary to practice the present invention, and the present invention is not limited to any particular mechanism), it is proposed the that the sporicidal ability of these emulsions occurs through initiation of germination without complete reversion to the vegetative form leaving the spore susceptible to disruption by the emulsions. The initiation of germination could be mediated by the action of the emulsion or its components.

The bacteria-inactivating oil-in-water emulsions used in some embodiments of the present invention can be used to inactivate a variety of bacteria and bacterial spores upon contact. For example, the presently disclosed emulsions can be used to inactivate *Bacillus* including *B. cereus, B. circulans* and *B. megatetium*, also including *Clostridium* (e.g., *C. botulinum* and *C. tetani*). The nanoemulsions utilized in some embodiments of the present invention may be particularly useful in inactivating certain biological warfare agents (e.g., *B. anthracis*). In addition, the formulations of the present invention also find use in combating *C. perfringens, H. influenzae, N. gonorrhoeae, S. agalactiae, S. pneumonia, S. pyogenes* and *V. cholerae* classical and Eltor.

Nanoemulsion adjuvant compositions of the present invention have anti-viral properties.

Yet another property of the nanoemulsion adjuvants used in some embodiments of the present invention is that they possess antifungal activity. Common agents of fungal infections include various species of the genii *Candida* and *Aspergillus*, and types thereof, as well as others. While external fungus infections can be relatively minor, systemic fungal infections can give rise to serious medical consequences. There is an increasing incidence of fungal infections in humans, attributable in part to an increasing number of patients having impaired immune systems. Fungal disease, particularly when systemic, can be life threatening to patients having an impaired immune system.

II. Nanoemulsion Adjuvant Compositions and Compositions for Inducing Immune Responses In some embodiments, the present invention provides compositions for inducing immune responses comprising a nanoemulsion adjuvant (e.g., independently and/or combined with one or more immunogens (e.g., inactivated pathogens or pathogen products) or allergen, allergenic substance or other material that causes an allergic response). A variety of nanoemulsion that find use in the present invention are described herein and elsewhere (e.g., nanoemulsions described in U.S. Pat. Apps. 20020045667 and 20040043041, and U.S. Pat. Nos. 6,015,832, 6,506,803, 6,635,676, and 6,559,189, each of which is incorporated herein by reference in its entirety for all purposes).

Nanoemulsion adjuvants (e.g., independently or combined with one or more immunogens (e.g., pathogens or pathogen products) or allergen, allergenic substance or other material that causes an allergic response) of the present invention may be combined in any suitable amount utilizing a variety of delivery methods. Any suitable pharmaceutical formulation may be utilized, including, but not limited to, those disclosed herein. Suitable formulations may be tested for immunogenicity using any suitable method. For example, in some embodiments, immunogenicity is investigated by quantitating both specific T-cell responses (e.g., cytokine profiles) and antibody titer. Nanoemulsion compositions of the present invention may also be tested in animal models of infectious disease states. Suitable animal models, pathogens, and assays for immunogenicity include, but are not limited to, those described herein.

Adjuvants have been traditionally developed from pro-inflammatory substances, such as a toxin or microbiological component, found to trigger signaling pathways and cytokine production (See, e.g., Graham, B. S., Plos Medicine, 2006. 3(1): p. e57). Also, enterotoxin-based adjuvants, such as cholera toxin, have been associated with inducing inflammation in the nasal mucosa and with production of the inflammatory cytokines and transport of the vaccine along olfactory neurons into the olfactory bulbs (See, e.g., van Ginkel, F. W., et al., Infect Immun., 2005. 73(10): p. 6892-6902). Some patients treated with a flu vaccine based on one of these toxins (NASALFLU, BERNA Biotech), developed Bell's palsy (See, e.g., Mutsch, M., et al., New England Journal of Medicine, 2004. 350(9): p. 896-903) presumably due to the vaccine in the olfactory bulb. This finding led to NASALFLU being withdrawn. In contrast, in some embodiments, the present invention provides nanoemulsion adjuvants (e.g., $W_{80}5EC$, $P_{40}75EC$, etc.) with no significant inflammation in animals and no evidence of the composition in the olfactory bulb. Thus, the present invention provides, in some embodiments, compositions and methods for inducing immune responses (e.g., immunity to) to pathogens or allergens, allergenic substances or other material that causes an allergic response utilizing needle-free mucosal administration, induction of systemic immunity comparable with conventional vaccines, as well as mucosal and cellular immune responses that are not elicited by injected, non-nanoemulsion adjuvant-based (e.g., aluminum-based) vaccines.

In some embodiments, the present invention provides methods of inducing an immune response and compositions useful in such methods (e.g., a nanoemulsion adjuvant composition). In some embodiments, methods of inducing an immune response in a host subject provided by the present invention are used for vaccination. For example, in some embodiments, the present invention provides a composition comprising a nanoemulsion adjuvant and one or a plurality of immunogens (e.g., derived from a plurality of pathogens (e.g., one or a plurality of pathogens inactivated by a nanoemulsion of the present invention and/or one or a plurality of protein and/or peptide antigens derived from (e.g., isolated and/or recombinantly produced from) one or a plurality of pathogens)); as well as methods of administering the composition (e.g., nasally administering) to a subject under conditions such that the subject generates an immune response to the one or a plurality of pathogens and/or immunogens. In some embodiments, administrating comprises mucosal administration. In some embodiments, inducing an immune response induces immunity to one or a plurality of immunogens in the subject. In some embodiments, inducing an immune response to the immunogens induces immunity to the plurality of pathogens from which the immunogens are derived. In some embodiments, immunity comprises systemic immunity. In some embodiments, immunity comprises mucosal immunity. In some embodiments, the immune response comprises a systemic IgG response to the immunogens (e.g., comparable to monovalent vaccine formulations). In some embodiments, the immune response comprises a mucosal IgA response to the immunogens. In some embodiments, the immune response to a multivalent immunogenic composition is characterized by a balanced Th1/Th2 polarization (e.g., an IgG subclass distribution and cytokine response indicative of a balanced Th1/Th2 response).

Thus, as described herein, the present invention, in one embodiment, provides adjuvant mixtures useful for formulating immunogenic compositions, suitable to be used as, for example, vaccines. As described in Examples 1-2, the immunogenic composition elicits an immune response by the host (e.g., host cells) to which it is administered (e.g., including the production of cytokines and other immune factors). In some embodiments, an adjuvant composition is formulated to include at least one antigen (e.g., pathogenic antigen or allergic antigen). An antigen may be an inactivated pathogen or an antigenic fraction of a pathogen, or an allergen, allergenic substance or other material that causes an allergic response. The pathogen may be, for example, a virus, a bacterium or a parasite. The pathogen may be inactivated by a chemical agent, such as formaldehyde, glutaraldehyde, beta-propiolactone, ethyleneimine and derivatives, the nanoemulsion adjuvant itself, or other compounds. The pathogen may also be inactivated by a physical agent, such as UV radiation, gamma radiation, "heat shock" and X-ray radiation. An antigenic fraction of a pathogen can be produced by means of chemical or physical decomposition methods, followed, if desired, by separation of a fraction by means of chromatography, centrifugation and similar techniques. Alternatively, antigens or haptens can be prepared by means of organic synthetic methods, or, in the case of, for example, polypeptides and proteins, by means of recombinant DNA methods. In some embodiments, an adjuvant composition of the invention is co-administered with a vaccine available in the marketplace (e.g., in order to generate a more robust immune response, in order to skew the immune response (e.g., toward a Th1 and away from a Th2 response) or to balance the type of immune response elicited by the vaccine).

In some embodiments, the present invention provides positively charged nanoemusion adjuvants (e.g., comprising a positive surface charge (e.g., due to the presence of a cationic compound (e.g., CPC))) that possesses greater efficacy at eliciting immune responses (e.g., innate immune responses and/or adaptive/acquired immune responses) than nanoemulsion adjuvants lacking a positive charge (e.g., lacking a positive surface charge (e.g., due to the absence of a cationic compound (e.g., CPC))). Although an understanding of a mechanism is not necessary to practice the present invention, and the present invention is not limited to any particular mechanism of action, in some embodiments, a nanoemulsion adjuvant possessing a positive charge (e.g., a positive surface charge (e.g., due to the presence of a cationic compound in the nanoemulsion (e.g., CPC))) possesses greater adhesion to mucosa (e.g., when administered intranasally) than non-positively charged emulsions (e.g., due to the positively charged surface of the emulsion). In some embodiments, a nanoemulsion adjuvant possessing a positive charge (e.g., a positive surface charge (e.g., due to the presence of a cationic compound in the nanoemulsion (e.g., CPC))) is more readily internalized by phagocytic cells (e.g., macrophages, dendritic cells, B cells, etc.) or other cells than is a non-positively charged nanoemulsion (e.g., leading to greater internalization of antigen (e.g., by antigen presenting cells), processing of antigen, and/or presentation of antigen to B and/or T cells). Thus, in some embodiments, greater internalization and/or processing of antigen and/or presentation of antigen to B and/or T cells leads to stronger, more robust immune responses (e.g., to an antigen administered in a nanoemulsion possessing a positive charge (e.g., a positive surface charge (e.g., due to the presence of a cationic compound in the nanoemulsion (e.g., CPC))).

In some embodiments, the present invention provides nanoemulsion adjuvants that generate a desired immune response in a subject administered the adjuvant (e.g., an adaptive immune response). For example, in some embodiments, the present invention provides nanoemulsion adjuvants that skew a host's immune response, when combined with and/or mixed with one or a plurality of antigens, away from Th2 type immune response and toward a Th1 type immune response. In particular, conventional alum based vaccines for a variety of diseases such as respiratory syncytial virus (RSV), anthrax, and hepatitis B virus each lead to a predominant Th2 type immune response in a subject administered the vaccine (e.g., characterized by enhanced expression of Th2 type cytokines and the production of IgG1 antibodies). However, immunogenic compositions (e.g., vaccines) produced with nanoemulsion adjuvant compositions of the invention and methods of using the same are able to redirect the conventionally observed Th2 type immune response in host subjects administered conventional vaccines. Moreover, the present invention also provides compositions and methods of using the same that are able to redirect and/or modulate immune responses underlying allergic disease. For example, compositions and methods of the invention are able to modulate (e.g., reduce or skew away from) Th2 immune responses (e.g., underling allergic disease) and promote Th1/Th17 immunity (e.g., skew towards a Th1 type immune response and/or a more balanced Th1/Th2 immune response) as a therapeutic for allergic disease, inflammatory disease, or any other disease associated with Th2 immunity.

Accordingly, in some embodiments, the present invention provides compositions and methods for skewing and/or redirecting allergic and/or inflammatory immune responses (e.g., away from Th2 type immune responses and toward Th1 type immune responses). In some embodiments, skewing and/or redirecting a host's immune response (e.g., away from Th2 type immune responses and toward Th1 type immune responses) to one or a plurality of immunogens/antigens comprises providing one or more antigens or allergens (e.g., recombinant antigens, isolated and/or purified antigens, and/or killed whole pathogens) that are historically associated with generation of a Th2 type immune response when administered to a subject, combining the one or more antigens or allergens with a nanoemulsion of the invention, and administering a therapeutically effective amounts of a nanoemulsion-antigen or nanoemulsion-allergen mixture to a subject under conditions sufficient to induce the desired immune response.

In some embodiments, the present invention provides adjuvants that reduce the number of booster injections (e.g., of an antigen containing composition) required to achieve protection. In some embodiments, the present invention provides adjuvants that result in a higher proportion of recipients achieving seroconversion. In some embodiments, the present invention provides adjuvants that are useful for selectively skewing adaptive immunity toward Th1 immune responses. In some embodiments, the present invention provides adjuvants that elicit optimal responses in subjects in which most contemporary vaccination strategies are not optimally effective (e.g., in very young and/or very old populations). In some embodiments, the present invention provides adjuvants that provide efficacy and safety needed for vaccination regimens that involve different delivery routes and elicitation of distinct types of immunity. In some embodiments, the present invention provides adjuvants that stimulate antibody responses and have little toxicity and that can be utilized with a range of antigens or allergens for which they provide adjuvanticity and the types of immune responses they elicit.

Nanoemulsions

The present invention is not limited by the type of nanoemulsion adjuvant utilized. Indeed, a variety of nanoemulsion adjuvants are contemplated to be useful in the present invention.

For example, in some embodiments, a nanoemulsion comprises (i) an aqueous phase; (ii) an oil phase; and at least one additional compound. In some embodiments of the present invention, these additional compounds are admixed into either the aqueous or oil phases of the composition. In other embodiments, these additional compounds are admixed into a composition of previously emulsified oil and aqueous phases. In certain of these embodiments, one or more additional compounds are admixed into an existing emulsion composition immediately prior to its use. In other embodiments, one or more additional compounds are admixed into an existing emulsion composition prior to the compositions immediate use.

Additional compounds suitable for use in a nanoemulsion of the present invention include, but are not limited to, one or more organic, and more particularly, organic phosphate based solvents, surfactants and detergents, cationic halogen containing compounds, germination enhancers, interaction enhancers, food additives (e.g., flavorings, sweeteners, bulking agents, and the like) and pharmaceutically acceptable compounds (e.g., carriers). Certain exemplary embodiments of the various compounds contemplated for use in the compositions of the present invention are presented below. Unless described otherwise, nanoemulsions are described in undiluted form.

Nanoemulsion adjuvant compositions of the present invention are not limited to any particular nanoemulsion. Any number of suitable nanoemulsion compositions may be utilized in the vaccine compositions of the present invention, including, but not limited to, those disclosed in Hamouda et al., J. Infect Dis., 180:1939 (1999); Hamouda and Baker, J. Appl. Microbiol., 89:397 (2000); and Donovan et al., Antivir. Chem. Chemother., 11:41 (2000). Preferred nanoemulsions of the present invention are those that are non-toxic to animals. In preferred embodiments, nanoemulsions utilized in the methods of the present invention are stable, and do not decompose even after long storage periods (e.g., one or more years). Additionally, preferred emulsions maintain stability even after exposure to high temperature and freezing. This is especially useful if they are to be applied in extreme conditions (e.g., extreme heat or cold).

Some embodiments of the present invention employ an oil phase containing ethanol. For example, in some embodiments, the emulsions of the present invention contain (i) an aqueous phase and (ii) an oil phase containing ethanol as the organic solvent and optionally a germination enhancer, and (iii) TYLOXAPOL as the surfactant (preferably 2-5%, more preferably 3%). This formulation is highly efficacious for inactivation of pathogens and is also non-irritating and non-toxic to mammalian subjects (e.g., and thus can be used for administration to a mucosal surface).

In some other embodiments, the emulsions of the present invention comprise a first emulsion emulsified within a second emulsion, wherein (a) the first emulsion comprises (i) an aqueous phase; and (ii) an oil phase comprising an oil and an organic solvent; and (iii) a surfactant; and (b) the second emulsion comprises (i) an aqueous phase; and (ii) an oil phase comprising an oil and a cationic containing compound; and (iii) a surfactant.

Exemplary Formulations

The following description provides a number of exemplary emulsions including formulations for compositions BCTP and $X_8W_{60}PC$. BCTP comprises a water-in oil nanoemulsion, in which the oil phase was made from soybean oil, tri-n-butyl phosphate, and TRITON X-100 in 80% water. $X_8W_{60}PC$ comprises a mixture of equal volumes of BCTP with $W_{80}8P$. $W_{80}8P$ is a liposome-like compound made of glycerol monostearate, refined oya sterols (e.g., GENEROL sterols), TWEEN 60, soybean oil, a cationic ion halogen-containing CPC and peppermint oil. The GENEROL family are a group of a polyethoxylated soya sterols (Henkel Corporation, Ambler, Pa.). Exemplary emulsion formulations useful in the present invention are provided in Table 1. These particular formulations may be found in U.S. Pat. No. 5,700,679 (NN); U.S. Pat. Nos. 5,618,840; 5,549,901 ($W_{80}8P$); and U.S. Pat. No. 5,547,677, each of which is hereby incorporated by reference in their entireties. Certain other emulsion formulations are presented U.S. patent application Ser. No. 10/669,865, hereby incorporated by reference in its entirety.

The $X_8W_{60}PC$ emulsion is manufactured by first making the $W_{80}8P$ emulsion and BCTP emulsions separately. A mixture of these two emulsions is then re-emulsified to produce a fresh emulsion composition termed $X_8W_{60}PC$. Methods of producing such emulsions are described in U.S. Pat. Nos. 5,103,497 and 4,895,452 (each of which is herein incorporated by reference in their entireties).

TABLE 1

| | Oil Phase Formula | Water to Oil Phase Ratio (Vol/Vol) |
|---|---|---|
| BCTP | 1 vol. Tri(N- butyl)phosphate<br>1 vol. TRITON X-100<br>8 vol. Soybean oil | 4:1 |
| NN | 86.5 g Glycerol monooleate<br>60.1 ml Nonoxynol-9<br>24.2 g GENEROL 122<br>3.27 g Cetylpyridinium chloride<br>554 g Soybean oil | 3:1 |
| $W_{80}8P$ | 86.5 g Glycerol monooleate<br>21.2 g Polysorbate 60<br>24.2 g GENEROL 122<br>3.27 g Cetylpyridinium chloride<br>4 ml Peppermint oil<br>554 g Soybean oil | 3.2:1 |
| SS | 86.5 g Glycerol monooleate<br>21.2 g Polysorbate 60<br>24.2 g GENEROL 122<br>3.27 g Cetylpyridinium chloride<br>554 g Soybean oil | 3.2:1<br>(1% bismuth<br>in water) |

The compositions listed above are only exemplary and those of skill in the art will be able to alter the amounts of the components to arrive at a nanoemulsion composition suitable for the purposes of the present invention. Those skilled in the art will understand that the ratio of oil phase to water as well as the individual oil carrier, surfactant CPC and organic phosphate buffer, components of each composition may vary.

Although certain compositions comprising BCTP have a water to oil ratio of 4:1, it is understood that the BCTP may be formulated to have more or less of a water phase. For example, in some embodiments, there is 3, 4, 5, 6, 7, 8, 9, 10, or more parts of the water phase to each part of the oil phase. The same holds true for the $W_{80}8P$ formulation. Similarly, the ratio of Tri (N-butyl) phosphate:TRITON X-100:soybean oil also may be varied.

Although Table 1 lists specific amounts of glycerol monooleate, polysorbate 60, GENEROL 122, cetylpyridinium chloride, and carrier oil for $W_{80}8P$, these are merely exemplary. An emulsion that has the properties of $W_{80}8P$ may be formulated that has different concentrations of each of these components or indeed different components that will fulfill the same function. For example, the emulsion may have between about 80 to about 100 g of glycerol monooleate in the initial oil phase. In other embodiments, the emulsion may have between about 15 to about 30 g polysorbate 60 in the initial oil phase. In yet another embodiment the composition may comprise between about 20 to about 30 g of a GENEROL sterol, in the initial oil phase.

Individual components of nanoemulsions (e.g. in an immunogenic composition of the present invention) can function both to inactivate a pathogen as well as to contribute to the non-toxicity of the emulsions. For example, the active component in BCTP, TRITON-X100, shows less ability to inactivate a virus at concentrations equivalent to 11% BCTP. Adding the oil phase to the detergent and solvent markedly reduces the toxicity of these agents in tissue culture at the same concentrations. While not being bound to any theory (an understanding of the mechanism is not necessary to practice the present invention, and the present invention is not limited to any particular mechanism), it is suggested that the nanoemulsion enhances the interaction of its components with the pathogens thereby facilitating the inactivation of the pathogen and reducing the toxicity of the individual components. Furthermore, when all the components of BCTP are combined in one composition but are not in a nanoemulsion structure, the mixture is not as effective at inactivating a pathogen as when the components are in a nanoemulsion structure.

Numerous additional embodiments presented in classes of formulations with like compositions are presented below. The following compositions recite various ratios and mixtures of active components. One skilled in the art will appreciate that the below recited formulation are exemplary and that additional formulations comprising similar percent ranges of the recited components are within the scope of the present invention.

In certain embodiments of the present invention, a nanoemulsion comprises from about 3 to 8 vol. % of TYLOXAPOL, about 8 vol. % of ethanol, about 1 vol. % of cetylpyridinium chloride (CPC), about 60 to 70 vol. % oil (e.g., soybean oil), about 15 to 25 vol. % of aqueous phase (e.g., $DiH_2O$ or PBS), and in some formulations less than about 1 vol. % of 1N NaOH. Some of these embodiments comprise PBS. It is contemplated that the addition of 1N NaOH and/or PBS in some of these embodiments, allows the user to advantageously control the pH of the formulations, such that pH ranges from about 7.0 to about 9.0, and more preferably from about 7.1 to 8.5 are achieved. For example, one embodiment of the present invention comprises about 3 vol. % of TYLOXAPOL, about 8 vol. % of ethanol, about 1 vol. % of CPC, about 64 vol. % of soybean oil, and about 24 vol. % of $DiH_2O$ (designated herein as Y3EC). Another similar embodiment comprises about 3.5 vol. % of TYLOXAPOL, about 8 vol. % of ethanol, and about 1 vol. % of CPC, about 64 vol. % of soybean oil, and about 23.5 vol. % of $DiH_2O$ (designated herein as Y3.5EC). Yet another embodiment comprises about 3 vol. % of TYLOXAPOL, about 8 vol. % of ethanol, about 1 vol. % of CPC, about 0.067 vol. % of 1N NaOH, such that the pH of the formulation is about 7.1, about 64 vol. % of soybean oil, and about 23.93 vol. % of $DiH_2O$ (designated herein as Y3EC pH 7.1). Still another embodiment comprises about 3 vol. % of TYLOXAPOL, about 8 vol. % of ethanol, about 1 vol. % of CPC, about 0.67 vol. % of 1N NaOH, such that the pH of the formulation is about 8.5, and about 64 vol. % of soybean oil, and about 23.33 vol. % of $DiH_2O$ (designated herein as Y3EC pH 8.5). Another similar embodiment comprises about 4% TYLOXAPOL, about 8 vol. % ethanol, about 1% CPC, and about 64 vol. % of soybean oil, and about 23 vol. % of $DiH_2O$ (designated herein as Y4EC). In still another embodiment the formulation comprises about 8% TYLOXAPOL, about 8% ethanol, about 1 vol. % of CPC, and about 64 vol. % of soybean oil, and about 19 vol. % of $DiH_2O$ (designated herein as Y8EC). A further embodiment comprises about 8 vol. % of TYLOXAPOL, about 8 vol. % of ethanol, about 1 vol. % of CPC, about 64 vol. % of soybean oil, and about 19 vol. % of 1×PBS (designated herein as Y8EC PBS).

In some embodiments of the present invention, a nanoemulsion comprises about 8 vol. % of ethanol, and about 1 vol. % of CPC, and about 64 vol. % of oil (e.g., soybean oil), and about 27 vol. % of aqueous phase (e.g., $DiH_2O$ or PBS) (designated herein as EC).

In some embodiments, a nanoemulsion comprises from about 8 vol. % of sodium dodecyl sulfate (SDS), about 8 vol. % of tributyl phosphate (TBP), and about 64 vol. % of oil (e.g., soybean oil), and about 20 vol. % of aqueous phase (e.g., $DiH_2O$ or PBS) (designated herein as S8P).

In some embodiments, a nanoemulsion comprises from about 1 to 2 vol. % of TRITON X-100, from about 1 to 2 vol. % of TYLOXAPOL, from about 7 to 8 vol. % of ethanol, about 1 vol. % of cetylpyridinium chloride (CPC), about 64 to 57.6 vol. % of oil (e.g., soybean oil), and about 23 vol. % of aqueous phase (e.g., $DiH_2O$ or PBS). Additionally, some of these formulations further comprise about 5 mM of L-alanine/Inosine, and about 10 mM ammonium chloride. Some of these formulations comprise PBS. It is contemplated that the addition of PBS in some of these embodiments, allows the user to advantageously control the pH of the formulations. For example, one embodiment of the present invention comprises about 2 vol. % of TRITON X-100, about 2 vol. % of TYLOXAPOL, about 8 vol. % of ethanol, about 1 vol. % CPC, about 64 vol. % of soybean oil, and about 23 vol. % of aqueous phase $DiH_2O$. In another embodiment the formulation comprises about 1.8 vol. % of TRITON X-100, about 1.8 vol. % of TYLOXAPOL, about 7.2 vol. % of ethanol, about 0.9 vol. % of CPC, about 5 mM L-alanine/Inosine, and about 10 mM ammonium chloride, about 57.6 vol. % of soybean oil, and the remainder of 1×PBS (designated herein as 90% X2Y2EC/GE).

In alternative embodiments, a nanoemulsion comprises from about 5 vol. % of TWEEN 80, from about 8 vol. % of ethanol, from about 1 vol. % of CPC, about 64 vol. % of oil (e.g., soybean oil), and about 22 vol. % of $DiH_2O$ (designated herein as $W_{80}$5EC). In yet another alternative embodiment, a nanoemulsion comprises from about 5 vol. % of TWEEN 80, from about 8 vol. % of ethanol, about 64 vol. % of oil (e.g., soybean oil), and about 23 vol. % of $DiH_2O$ (designated herein as $W_{80}$5E).

In some embodiments, the present invention provides a nanoemulsion comprising from about 5 vol. % of Poloxamer-407, from about 8 vol. % of ethanol, from about 1 vol. % of CPC, about 64 vol. % of oil (e.g., soybean oil), and about 22 vol. % of $DiH_2O$ (designated herein as $P_{407}$5EC). Although an understanding of the mechanism is not necessary to practice the present invention, and the present invention is not limited to any particular mechanism, in some embodiments, a nanoemulsion comprising Poloxamer-407 does not elicit and/or augment immune responses (e.g., in the lung) in a subject. In some embodiments, various dilutions of a nanoemulsion provided herein (e.g., $P_{407}$5EC) can be utilized to treat (e.g., kill and/or inhibit growth of) bacteria. In some embodiments, undiluted nanoemulsion is utilized. In some embodiments, $P_{407}$5EC is diluted (e.g., in serial, two fold dilutions) to obtain a desired concentration of one of the constituents of the nanoemulsion (e.g., CPC).

In still other embodiments of the present invention, a nanoemulsion comprises from about 5 vol. % of TWEEN 20, from about 8 vol. % of ethanol, from about 1 vol. % of CPC, about 64 vol. % of oil (e.g., soybean oil), and about 22 vol. % of $DiH_2O$ (designated herein as $W_{20}$5EC).

In still other embodiments of the present invention, a nanoemulsion comprises from about 2 to 8 vol. % of TRITON X-100, about 8 vol. % of ethanol, about 1 vol. % of CPC, about 60 to 70 vol. % of oil (e.g., soybean, or olive oil), and about 15 to 25 vol. % of aqueous phase (e.g., $DiH_2O$ or PBS). For example, the present invention contemplates formulations comprising about 2 vol. % of TRITON X-100, about 8 vol. % of ethanol, about 64 vol. % of soybean oil, and about 26 vol. % of $DiH_2O$ (designated herein as X2E). In other similar embodiments, a nanoemulsion comprises about 3 vol. % of TRITON X-100, about 8 vol. % of ethanol, about 64 vol. % of soybean oil, and about 25 vol. % of DiH$_2$O (designated herein as X3E). In still further embodiments, the formulations comprise about 4 vol. % Triton of X-100, about 8 vol. % of ethanol, about 64 vol. % of soybean oil, and about 24 vol. % of DiH$_2$O (designated herein as X4E). In yet other embodiments, a nanoemulsion comprises about 5 vol. % of TRITON X-100, about 8 vol. % of ethanol, about 64 vol. % of soybean oil, and about 23 vol. % of DiH$_2$O (designated herein as X5E). In some embodiments, a nanoemulsion comprises about 6 vol. % of TRITON X-100, about 8 vol. % of ethanol, about 64 vol. % of soybean oil, and about 22 vol. % of DiH$_2$O (designated herein as X6E). In still further embodiments of the present invention, a nanoemulsion comprises about 8 vol. % of TRITON X-100, about 8 vol. % of ethanol, about 64 vol. % of soybean oil, and about 20 vol. % of DiH$_2$O (designated herein as X8E). In still further embodiments, a nanoemulsion comprises about 8 vol. % of TRITON X-100, about 8 vol. % of ethanol, about 64 vol. % of olive oil, and about 20 vol. % of DiH$_2$O (designated herein as X8E O). In yet another embodiment, a nanoemulsion comprises 8 vol. % of TRITON X-100, about 8 vol. % ethanol, about 1 vol. % CPC, about 64 vol. % of soybean oil, and about 19 vol. % of DiH$_2$O (designated herein as X8EC).

In alternative embodiments of the present invention, a nanoemulsion comprises from about 1 to 2 vol. % of TRITON X-100, from about 1 to 2 vol. % of TYLOXAPOL, from about 6 to 8 vol. % TBP, from about 0.5 to 1.0 vol. % of CPC, from about 60 to 70 vol. % of oil (e.g., soybean), and about 1 to 35 vol. % of aqueous phase (e.g., DiH$_2$O or PBS). Additionally, certain of these nanoemulsions may comprise from about 1 to 5 vol. % of trypticase soy broth, from about 0.5 to 1.5 vol. % of yeast extract, about 5 mM L-alanine/Inosine, about 10 mM ammonium chloride, and from about 20-40 vol. % of liquid baby formula. In some embodiments comprising liquid baby formula, the formula comprises a casein hydrolysate (e.g., Neutramigen, or Progestimil, and the like). In some of these embodiments, a nanoemulsion further comprises from about 0.1 to 1.0 vol. % of sodium thiosulfate, and from about 0.1 to 1.0 vol. % of sodium citrate. Other similar embodiments comprising these basic components employ phosphate buffered saline (PBS) as the aqueous phase. For example, one embodiment comprises about 2 vol. % of TRITON X-100, about 2 vol. % TYLOXAPOL, about 8 vol. % TBP, about 1 vol. % of CPC, about 64 vol. % of soybean oil, and about 23 vol. % of DiH$_2$O (designated herein as X2Y2EC). In still other embodiments, the inventive formulation comprises about 2 vol. % of TRITON X-100, about 2 vol. % TYLOXAPOL, about 8 vol. % TBP, about 1 vol. % of CPC, about 0.9 vol. % of sodium thiosulfate, about 0.1 vol. % of sodium citrate, about 64 vol. % of soybean oil, and about 22 vol. % of DiH$_2$O (designated herein as X2Y2PC STS1). In another similar embodiment, a nanoemulsion comprises about 1.7 vol. % TRITON X-100, about 1.7 vol. % TYLOXAPOL, about 6.8 vol. % TBP, about 0.85% CPC, about 29.2% NEUTRAMIGEN, about 54.4 vol. % of soybean oil, and about 4.9 vol. % of DiH$_2$O (designated herein as 85% X2Y2PC/baby). In yet another embodiment of the present invention, a nanoemulsion comprises about 1.8 vol. % of TRITON X-100, about 1.8 vol. % of TYLOXAPOL, about 7.2 vol. % of TBP, about 0.9 vol. % of CPC, about 5 mM L-alanine/Inosine, about 10 mM ammonium chloride, about 57.6 vol. % of soybean oil, and the remainder with 0.1×PBS (designated herein as 90% X2Y2 PC/GE). In still another embodiment, a nanoemulsion comprises about 1.8 vol. % of TRITON X-100, about 1.8 vol. % of TYLOXAPOL, about 7.2 vol. % TBP, about 0.9 vol. % of CPC, and about 3 vol. % trypticase soy broth, about 57.6 vol. % of soybean oil, and about 27.7 vol. % of DiH$_2$O (designated herein as 90% X2Y2PC/TSB). In another embodiment of the present invention, a nanoemulsion comprises about 1.8 vol. % TRITON X-100, about 1.8 vol. % TYLOXAPOL, about 7.2 vol. % TBP, about 0.9 vol. % CPC, about 1 vol. % yeast extract, about 57.6 vol. % of soybean oil, and about 29.7 vol. % of DiH$_2$O (designated as 90% X2Y2PC/YE).

In some embodiments of the present invention, a nanoemulsion comprises about 3 vol. % of TYLOXAPOL, about 8 vol. % of TBP, and about 1 vol. % of CPC, about 60 to 70 vol. % of oil (e.g., soybean or olive oil), and about 15 to 30 vol. % of aqueous phase (e.g., DiH$_2$O or PBS). In a particular embodiment of the present invention, a nanoemulsion comprises about 3 vol. % of TYLOXAPOL, about 8 vol. % of TBP, and about 1 vol. % of CPC, about 64 vol. % of soybean, and about 24 vol. % of DiH$_2$O (designated herein as Y3PC).

In some embodiments of the present invention, a nanoemulsion comprises from about 4 to 8 vol. % of TRITON X-100, from about 5 to 8 vol. % of TBP, about 30 to 70 vol. % of oil (e.g., soybean or olive oil), and 0 to 30 vol. % of aqueous phase (e.g., DiH$_2$O or PBS). Additionally, certain of these embodiments further comprise about 1 vol. % of CPC, about 1 vol. % of benzalkonium chloride, about 1 vol. % cetylyridinium bromide, about 1 vol. % cetyldimethyletylammonium bromide, 500 µM EDTA, about 10 mM ammonium chloride, about 5 mM Inosine, and about 5 mM L-alanine. For example, in a certain preferred embodiment, a nanoemulsion comprises about 8 vol. % of TRITON X-100, about 8 vol. % of TBP, about 64 vol. % of soybean oil, and about 20 vol. % of DiH$_2$O (designated herein as X8P). In another embodiment of the present invention, a nanoemulsion comprises about 8 vol. % of TRITON X-100, about 8 vol. % of TBP, about 1% of CPC, about 64 vol. % of soybean oil, and about 19 vol. % of DiH$_2$O (designated herein as X8PC). In still another embodiment, a nanoemulsion comprises about 8 vol. % TRITON X-100, about 8 vol. % of TBP, about 1 vol. % of CPC, about 50 vol. % of soybean oil, and about 33 vol. % of DiH$_2$O (designated herein as ATB-X1001). In yet another embodiment, the formulations comprise about 8 vol. % of TRITON X-100, about 8 vol. % of TBP, about 2 vol. % of CPC, about 50 vol. % of soybean oil, and about 32 vol. % of DiH$_2$O (designated herein as ATB-X002). In some embodiments, a nanoemulsion comprises about 4 vol. % TRITON X-100, about 4 vol. % of TBP, about 0.5 vol. % of CPC, about 32 vol. % of soybean oil, and about 59.5 vol. % of DiH$_2$O (designated herein as 50% X8PC). In some embodiments, a nanoemulsion comprises about 8 vol. % of TRITON X-100, about 8 vol. % of TBP, about 0.5 vol. % CPC, about 64 vol. % of soybean oil, and about 19.5 vol. % of DiH$_2$O (designated herein as X8PC$_{1/2}$). In some embodiments of the present invention, a nanoemulsion comprises about 8 vol. % of TRITON X-100, about 8 vol. % of TBP, about 2 vol. % of CPC, about 64 vol. % of soybean oil, and about 18 vol. % of DiH$_2$O (designated herein as X8PC2). In other embodiments, a nanoemulsion comprises about 8 vol. % of TRITON X-100, about 8% of TBP, about 1% of benzalkonium chloride, about 50 vol. % of soybean oil, and about 33 vol. % of DiH$_2$O (designated herein as X8P BC). In an alternative embodiment of the present invention, a nanoemulsion comprises about 8 vol. % of TRITON X-100, about 8 vol. % of TBP, about 1 vol. % of cetylyridinium bromide, about 50 vol. % of soybean oil, and about 33 vol. % of DiH$_2$O (designated herein as X8P CPB). In another exemplary embodiment of the present invention, a nanoemulsion comprises about 8 vol. % of TRITON X-100, about 8 vol. % of TBP, about 1 vol. % of cetyldimethyletylammonium bromide, about 50 vol. % of soybean oil, and about 33 vol. % of DiH$_2$O (designated herein as X8P CTAB). In still further embodiments, a nanoemulsion comprises about 8 vol. % of TRITON X-100, about 8 vol. % of TBP, about 1 vol. % of CPC, about 500 µM EDTA, about 64 vol. % of soybean oil, and about 15.8 vol. % DiH$_2$O (designated herein as X8PC EDTA). In some embodiments, a nanoemulsion comprises 8 vol. % of TRITON X-100, about 8 vol. % of TBP, about 1 vol. % of CPC, about 10 mM ammonium chloride, about 5 mM Inosine, about 5 mM L-alanine, about 64 vol. % of soybean oil, and about 19 vol. % of DiH$_2$O or PBS (designated herein as X8PC GE$_{1x}$). In another embodiment of the present invention, a nanoemulsion comprises about 5 vol. % of TRITON X-100, about 5% of TBP, about 1 vol. % of CPC, about 40 vol. % of soybean oil, and about 49 vol. % of DiH$_2$O (designated herein as X5P$_5$C).

In some embodiments of the present invention, a nanoemulsion comprises about 2 vol. % TRITON X-100, about 6 vol. % TYLOXAPOL, about 8 vol. % ethanol, about 64 vol. % of soybean oil, and about 20 vol. % of DiH$_2$O (designated herein as X2Y6E).

In an additional embodiment of the present invention, a nanoemulsion comprises about 8 vol. % of TRITON X-100, and about 8 vol. % of glycerol, about 60 to 70 vol. % of oil (e.g., soybean or olive oil), and about 15 to 25 vol. % of aqueous phase (e.g., DiH$_2$O or PBS). Certain nanoemulsion compositions (e.g., used to generate an immune response (e.g., for use as a vaccine) comprise about 1 vol. % L-ascorbic acid. For example, one particular embodiment comprises about 8 vol. % of TRITON X-100, about 8 vol. % of glycerol, about 64 vol. % of soybean oil, and about 20 vol. % of DiH$_2$O (designated herein as X8G). In still another embodiment, a nanoemulsion comprises about 8 vol. % of TRITON X-100, about 8 vol. % of glycerol, about 1 vol. % of L-ascorbic acid, about 64 vol. % of soybean oil, and about 19 vol. % of DiH$_2$O (designated herein as X8GV$_c$).

In still further embodiments, a nanoemulsion comprises about 8 vol. % of TRITON X-100, from about 0.5 to 0.8 vol. % of TWEEN 60, from about 0.5 to 2.0 vol. % of CPC, about 8 vol. % of TBP, about 60 to 70 vol. % of oil (e.g., soybean or olive oil), and about 15 to 25 vol. % of aqueous phase (e.g., DiH$_2$O or PBS). For example, in one particular embodiment a nanoemulsion comprises about 8 vol. % of TRITON X-100, about 0.70 vol. % of TWEEN 60, about 1 vol. % of CPC, about 8 vol. % of TBP, about 64 vol. % of soybean oil, and about 18.3 vol. % of DiH$_2$O (designated herein as X8W60PC$_1$). In some embodiments, a nanoemulsion comprises about 8 vol. % of TRITON X-100, about 0.71 vol. % of TWEEN 60, about 1 vol. % of CPC, about 8 vol. % of TBP, about 64 vol. % of soybean oil, and about 18.29 vol. % of DiH$_2$O (designated herein as W60$_{0.7}$X8PC). In yet other embodiments, a nanoemulsion comprises from about 8 vol. % of TRITON X-100, about 0.7 vol. % of TWEEN 60, about 0.5 vol. % of CPC, about 8 vol. % of TBP, about 64 to 70 vol. % of soybean oil, and about 18.8 vol. % of DiH$_2$O (designated herein as X8W60PC$_2$). In still other embodiments, a nanoemulsion comprises about 8 vol. % of TRITON X-100, about 0.71 vol. % of TWEEN 60, about 2 vol. % of CPC, about 8 vol. % of TBP, about 64 vol. % of soybean oil, and about 17.3 vol. % of DiH$_2$O. In another embodiment of the present invention, a nanoemulsion comprises about 0.71 vol. % of TWEEN 60, about 1 vol. % of CPC, about 8 vol. % of TBP, about 64 vol. % of soybean oil, and about 25.29 vol. % of DiH$_2$O (designated herein as W60$_{0.7}$PC).

In another embodiment of the present invention, a nanoemulsion comprises about 2 vol. % of dioctyl sulfosuccinate, either about 8 vol. % of glycerol, or about 8 vol. % TBP, in addition to, about 60 to 70 vol. % of oil (e.g., soybean or olive oil), and about 20 to 30 vol. % of aqueous phase (e.g., DiH$_2$O or PBS). For example, in some embodiments, a nanoemulsion comprises about 2 vol. % of dioctyl sulfosuccinate, about 8 vol. % of glycerol, about 64 vol. % of soybean oil, and about 26 vol. % of DiH$_2$O (designated herein as D2G). In another related embodiment, a nanoemulsion comprises about 2 vol. % of dioctyl sulfosuccinate, and about 8 vol. % of TBP, about 64 vol. % of soybean oil, and about 26 vol. % of DiH$_2$O (designated herein as D2P).

In still other embodiments of the present invention, a nanoemulsion comprises about 8 to 10 vol. % of glycerol, and about 1 to 10 vol. % of CPC, about 50 to 70 vol. % of oil (e.g., soybean or olive oil), and about 15 to 30 vol. % of aqueous phase (e.g., DiH$_2$O or PBS). Additionally, in certain of these embodiments, a nanoemulsion further comprises about 1 vol. % of L-ascorbic acid. For example, in some embodiments, a nanoemulsion comprises about 8 vol. % of glycerol, about 1 vol. % of CPC, about 64 vol. % of soybean oil, and about 27 vol. % of DiH$_2$O (designated herein as GC). In some embodiments, a nanoemulsion comprises about 10 vol. % of glycerol, about 10 vol. % of CPC, about 60 vol. % of soybean oil, and about 20 vol. % of DiH$_2$O (designated herein as GC10). In still another embodiment of the present invention, a nanoemulsion comprises about 10 vol. % of glycerol, about 1 vol. % of CPC, about 1 vol. % of L-ascorbic acid, about 64 vol. % of soybean or oil, and about 24 vol. % of DiH$_2$O (designated herein as GCV$_c$).

In some embodiments of the present invention, a nanoemulsion comprises about 8 to 10 vol. % of glycerol, about 8 to 10 vol. % of SDS, about 50 to 70 vol. % of oil (e.g., soybean or olive oil), and about 15 to 30 vol. % of aqueous phase (e.g., DiH$_2$O or PBS). Additionally, in certain of these embodiments, a nanoemulsion further comprise about 1 vol. % of lecithin, and about 1 vol. % of p-Hydroxybenzoic acid methyl ester. Exemplary embodiments of such formulations comprise about 8 vol. % SDS, 8 vol. % of glycerol, about 64 vol. % of soybean oil, and about 20 vol. % of DiH$_2$O (designated herein as S8G). A related formulation comprises about 8 vol. % of glycerol, about 8 vol. % of SDS, about 1 vol. % of lecithin, about 1 vol. % of p-Hydroxybenzoic acid methyl ester, about 64 vol. % of soybean oil, and about 18 vol. % of DiH$_2$O (designated herein as S8GL1B1).

In yet another embodiment of the present invention, a nanoemulsion comprises about 4 vol. % of TWEEN 80, about 4 vol. % of TYLOXAPOL, about 1 vol. % of CPC, about 8 vol. % of ethanol, about 64 vol. % of soybean oil, and about 19 vol. % of DiH$_2$O (designated herein as W$_{80}$4Y4EC).

In some embodiments of the present invention, a nanoemulsion comprises about 0.01 vol. % of CPC, about 0.08 vol. % of TYLOXAPOL, about 10 vol. % of ethanol, about 70 vol. % of soybean oil, and about 19.91 vol. % of DiH$_2$O (designated herein as Y.08EC.01).

In yet another embodiment of the present invention, a nanoemulsion comprises about 8 vol. % of sodium lauryl sulfate, and about 8 vol. % of glycerol, about 64 vol. % of soybean oil, and about 20 vol. % of DiH$_2$O (designated herein as SLS8G).

The specific formulations described above are simply examples to illustrate the variety of nanoemulsion adjuvants that find use in the present invention. The present invention contemplates that many variations of the above formulations, as well as additional nanoemulsions, find use in the methods of the present invention. Candidate emulsions can be easily tested to determine if they are suitable. First, the desired ingredients are prepared using the methods described herein, to determine if an emulsion can be formed. If an emulsion cannot be formed, the candidate is rejected. For example, a candidate composition made of 4.5% sodium thiosulfate, 0.5% sodium citrate, 10% n-butanol, 64% soybean oil, and 21% DiH$_2$O does not form an emulsion.

Second, the candidate emulsion should form a stable emulsion. An emulsion is stable if it remains in emulsion form for a sufficient period to allow its intended use (e.g., to generate an immune response in a subject). For example, for emulsions that are to be stored, shipped, etc., it may be desired that the composition remain in emulsion form for months to years. Typical emulsions that are relatively unstable, will lose their form within a day. For example, a candidate composition made of 8% 1-butanol, 5% TWEEN 10, 1% CPC, 64% soybean oil, and 22% DiH$_2$O does not form a stable emulsion. Nanoemulsions that have been shown to be stable include, but are not limited to, 8 vol. % of TRITON X-100, about 8 vol. % of TBP, about 64 vol. % of soybean oil, and about 20 vol. % of DiH$_2$O (designated herein as X8P); 5 vol. % of TWEEN 20, from about 8 vol. % of ethanol, from about 1 vol. % of CPC, about 64 vol. % of oil (e.g., soybean oil), and about 22 vol. % of DiH$_2$O (designated herein as W$_{20}$5EC); 0.08% Triton X-100, 0.08% Glycerol, 0.01% Cetylpyridinium Chloride, 99% Butter, and 0.83% diH$_2$O (designated herein as 1% X8GC Butter); 0.8% Triton X-100, 0.8% Glycerol, 0.1% Cetylpyridinium Chloride, 6.4% Soybean Oil, 1.9% diH$_2$O, and 90% Butter (designated herein as 10% X8GC Butter); 2% W$_{20}$5EC, 1% Natrosol 250L NF, and 97% diH$_2$O (designated herein as 2% W$_{20}$5EC L GEL); 1% Cetylpyridinium Chloride, 5% TWEEN 20, 8% Ethanol, 64% 70 Viscosity Mineral Oil, and 22% diH$_2$O (designated herein as W$_{20}$5EC 70 Mineral Oil); 1% Cetylpyridinium Chloride, 5% TWEEN 20, 8% Ethanol, 64% 350 Viscosity Mineral Oil, and 22% diH$_2$O (designated herein as W$_{20}$5EC 350 Mineral Oil). In some embodiments, nanoemulsions of the present invention are stable for over a week, over a month, or over a year.

Third, the candidate emulsion should have efficacy for its intended use. For example, a nanoemulsion should inactivate (e.g., kill or inhibit growth of) a pathogen to a desired level (e.g., 1 log, 2 log, 3 log, 4 log, . . . reduction). Using the methods described herein, one is capable of determining the suitability of a particular candidate emulsion against the desired pathogen. Generally, this involves exposing the pathogen to the emulsion for one or more time periods in a side-by-side experiment with the appropriate control samples (e.g., a negative control such as water) and determining if, and to what degree, the emulsion inactivates (e.g., kills and/or neutralizes) the microorganism. For example, a candidate composition made of 1% ammonium chloride, 5% TWEEN 20, 8% ethanol, 64% soybean oil, and 22% DiH$_2$O was shown not to be an effective emulsion. The following candidate emulsions were shown to be effective using the methods described herein: 5% TWEEN 20, 5% Cetylpyridinium Chloride, 10% Glycerol, 60% Soybean Oil, and 20% diH$_2$O (designated herein as W$_{20}$5GC5); 1% Cetylpyridinium Chloride, 5% TWEEN 20, 10% Glycerol, 64% Soybean Oil, and 20% diH$_2$O (designated herein as W$_{20}$5GC); 1% Cetylpyridinium Chloride, 5% TWEEN 20, 8% Ethanol, 64% Olive Oil, and 22% diH$_2$O (designated herein as W$_{20}$5EC Olive Oil); 1% Cetylpyridinium Chloride, 5% TWEEN 20, 8% Ethanol, 64% Flaxseed Oil, and 22% diH$_2$O (designated herein as W$_{20}$5EC Flaxseed Oil); 1% Cetylpyridinium Chloride, 5% TWEEN 20, 8% Ethanol, 64% Corn Oil, and 22% diH$_2$O (designated herein as W$_{20}$5EC Corn Oil); 1% Cetylpyridinium Chloride, 5% TWEEN 20, 8% Ethanol, 64% Coconut Oil, and 22% diH$_2$O (designated herein as W$_{20}$5EC Coconut Oil); 1% Cetylpyridinium Chloride, 5% TWEEN 20, 8% Ethanol, 64% Cottonseed Oil, and 22% diH$_2$O (designated herein as W$_{20}$5EC Cottonseed Oil); 8% Dextrose, 5% TWEEN 10, 1% Cetylpyridinium Chloride, 64% Soybean Oil, and 22% diH$_2$O (designated herein as W$_{20}$5C Dextrose); 8% PEG 200, 5% TWEEN 10, 1% Cetylpyridinium Chloride, 64% Soybean Oil, and 22% diH$_2$O (designated herein as W$_{20}$5C PEG 200); 8% Methanol, 5% TWEEN 10, 1% Cetylpyridinium Chloride, 64% Soybean Oil, and 22% diH$_2$O (designated herein as W$_{20}$5C Methanol); 8% PEG 1000, 5% TWEEN 10, 1% Cetylpyridinium Chloride, 64% Soybean Oil, and 22% diH$_2$O (designated herein as W$_{20}$5C PEG 1000); 2% W$_{20}$5EC, 2% Natrosol 250H NF, and 96% diH$_2$O (designated herein as 2% W$_{20}$5EC Natrosol 2, also called 2% W$_{20}$5EC GEL); 2% W$_{20}$5EC, 1% Natrosol 250H NF, and 97% diH$_2$O (designated herein as 2% W$_{20}$5EC Natrosol 1); 2% W$_{20}$5EC, 3% Natrosol 250H NF, and 95% diH$_2$O (designated herein as 2% W$_{20}$5EC Natrosol 3); 2% W$_{20}$5EC, 0.5% Natrosol 250H NF, and 97.5% diH$_2$O (designated herein as 2% W$_{20}$5EC Natrosol 0.5); 2% W$_{20}$5EC, 2% Methocel A, and 96% diH$_2$O (designated herein as 2% W$_{20}$5EC Methocel A); 2% W$_{20}$5EC, 2% Methocel K, and 96% diH$_2$O (designated herein as 2% W$_{20}$5EC Methocel K); 2% Natrosol, 0.1% X8PC, 0.1×PBS, 5 mM L-alanine, 5 mM Inosine, 10 mM Ammonium Chloride, and diH$_2$O (designated herein as 0.1% X8PC/GE+2% Natrosol); 2% Natrosol, 0.8% Triton X-100, 0.8% Tributyl Phosphate, 6.4% Soybean Oil, 0.1% Cetylpyridinium Chloride, 0.1×PBS, 5 mM L-alanine, 5 mM Inosine, 10 mM Ammonium Chloride, and diH$_2$O (designated herein as 10% X8PC/GE+2% Natrosol); 1% Cetylpyridinium Chloride, 5% TWEEN 20, 8% Ethanol, 64% Lard, and 22% diH$_2$O (designated herein as W$_{20}$5EC Lard); 1% Cetylpyridinium Chloride, 5% TWEEN 20, 8% Ethanol, 64% Mineral Oil, and 22% diH$_2$O (designated herein as W$_{20}$5EC Mineral Oil); 0.1% Cetylpyridinium Chloride, 2% Nerolidol, 5% TWEEN 20, 10% Ethanol, 64% Soybean Oil, and 18.9% diH$_2$O (designated herein as W$_{20}$5EC$_{0.1}$N); 0.1% Cetylpyridinium Chloride, 2% Farnesol, 5% TWEEN 20, 10% Ethanol, 64% Soybean Oil, and 18.9% diH$_2$O (designated herein as W$_{20}$5EC$_{0.1}$F); 0.1% Cetylpyridinium Chloride, 5% TWEEN 20, 10% Ethanol, 64% Soybean Oil, and 20.9% diH$_2$O (designated herein as W$_{20}$5EC$_{0.1}$); 10% Cetylpyridinium Chloride, 8% Tributyl Phosphate, 8% Triton X-100, 54% Soybean Oil, and 20% diH$_2$O (designated herein as X8PC$_{10}$); 5% Cetylpyridinium Chloride, 8% Triton X-100, 8% Tributyl Phosphate, 59% Soybean Oil, and 20% diH$_2$O (designated herein as X8PC$_5$); 0.02% Cetylpyridinium Chloride, 0.1% TWEEN 20, 10% Ethanol, 70% Soybean Oil, and 19.88% diH$_2$O (designated herein as W$_{20}$0.1EC$_{0.02}$); 1% Cetylpyridinium Chloride, 5% TWEEN 20, 8% Glycerol, 64% Mobil 1, and 22% diH$_2$O (designated herein as W$_{20}$5GC Mobil 1); 7.2% Triton X-100, 7.2% Tributyl Phosphate, 0.9% Cetylpyridinium Chloride, 57.6% Soybean Oil, 0.1×PBS, 5 mM L-alanine, 5 mM Inosine, 10 mM Ammonium Chloride, and 25.87% diH$_2$O (designated herein as 90% X8PC/GE); 7.2% Triton X-100, 7.2% Tributyl Phosphate, 0.9% Cetylpyridinium Chloride, 57.6% Soybean Oil, 1% EDTA, 5 mM L-alanine, 5 mM Inosine, 10 mM Ammonium Chloride, 0.1×PBS, and diH$_2$O (designated herein as 90% X8PC/GE EDTA); and 7.2% Triton X-100, 7.2% Tributyl Phosphate, 0.9% Cetylpyridinium Chloride, 57.6% Soybean Oil, 1% Sodium Thiosulfate, 5 mM L-alanine, 5 mM Inosine, 10 mM Ammonium Chloride, 0.1×PBS, and diH$_2$O (designated herein as 90% X8PC/GE STS).

In preferred embodiments of the present invention, the nanoemulsions are non-toxic (e.g., to humans, plants, or animals), non-irritant (e.g., to humans, plants, or animals), and non-corrosive (e.g., to humans, plants, or animals or the environment), while retaining stability when mixed with other agents (e.g., a composition comprising an immunogen (e.g., bacteria, fungi, viruses, and spores). While a number of the above described nanoemulsions meet these qualifications, the following description provides a number of preferred non-toxic, non-irritant, non-corrosive, anti-microbial nanoemulsions of the present invention (hereinafter in this section referred to as "non-toxic nanoemulsions").

In some embodiments the non-toxic nanoemulsions comprise surfactant lipid preparations (SLPs) for use as broad-spectrum antimicrobial agents that are effective against bacteria and their spores, enveloped viruses, and fungi. In preferred embodiments, these SLPs comprise a mixture of oils, detergents, solvents, and cationic halogen-containing compounds in addition to several ions that enhance their biocidal activities. These SLPs are characterized as stable, non-irritant, and non-toxic compounds compared to commercially available bactericidal and sporicidal agents, which are highly irritant and/or toxic.

Ingredients for use in the non-toxic nanoemulsions include, but are not limited to: detergents (e.g., TRITON X-100 (5-15%) or other members of the TRITON family, TWEEN 60 (0.5-2%) or other members of the TWEEN family, or TYLOXAPOL (1-10%)); solvents (e.g., tributyl phosphate (5-15%)); alcohols (e.g., ethanol (5-15%) or glycerol (5-15%)); oils (e.g., soybean oil (40-70%)); cationic halogen-containing compounds (e.g., cetylpyridinium chloride (0.5-2%), cetylpyridinium bromide (0.5-2%)), or cetyldimethylethyl ammonium bromide (0.5-2%)); quaternary ammonium compounds (e.g., benzalkonium chloride (0.5-2%), N-alkyldimethylbenzyl ammonium chloride (0.5-2%)); ions (calcium chloride (1 mM-40 mM), ammonium chloride (1 mM-20 mM), sodium chloride (5 mM-200 mM), sodium phosphate (1 mM-20 mM)); nucleosides (e.g., inosine (50 μM-20 mM)); and amino acids (e.g., L-alanine (50 μM-20 mM)). Emulsions are prepared, for example, by mixing in a high shear mixer for 3-10 minutes. The emulsions may or may not be heated before mixing at 82° C. for 1 hour.

Quaternary ammonium compounds for use in the present include, but are not limited to, N-alkyldimethyl benzyl ammonium saccharinate; 1,3,5-Triazine-1,3,5(2H,4H,6H)-triethanol; 1-Decanaminium, N-decyl-N, N-dimethyl-, chloride (or) Didecyl dimethyl ammonium chloride; 2-(2-(p-(Diisobuyl)cresosxy)ethoxy)ehyl dimethyl benzyl ammonium chloride; 2-(2-(p-(Diisobutyl)phenoxy)ethoxy) ethyl dimethyl benzyl ammonium chloride; alkyl 1 or 3 benzyl-1-(2-hydroxethyl)-2-imidazolinium chloride; alkyl bis(2-hydroxyethyl) benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl (ethylbenzyl) ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis (2-hydroxyethyl) octyl hydrogen ammonium chloride; dodecyl dimethyl benzyl ammonium chloride; dodecylcarbamoyl methyl dinethyl benzyl ammonium chloride; heptadecyl hydroxyethylimidazolinium chloride; hexahydro-1,3,5-thris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis (alkyl dimethyl ammonium chloride); quaternary ammonium compounds, dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethylbenzyl ammonium chloride; and n-octadecyl dimethyl benzyl ammonium chloride.

1. Aqueous Phase

In some embodiments, the emulsion comprises an aqueous phase. In certain preferred embodiments, the emulsion comprises about 5 to 50, preferably 10 to 40, more preferably 15 to 30, vol. % aqueous phase, based on the total volume of the emulsion (although other concentrations are also contemplated). In preferred embodiments, the aqueous phase comprises water at a pH of about 4 to 10, preferably about 6 to 8. The water is preferably deionized (hereinafter "DiH$_2$O"). In some embodiments, the aqueous phase comprises phosphate buffered saline (PBS). In some preferred embodiments, the aqueous phase is sterile and pyrogen free.

2. Oil Phase

In some embodiments, the emulsion comprises an oil phase. In certain preferred embodiments, the oil phase (e.g., carrier oil) of the emulsion of the present invention comprises 30-90, preferably 60-80, and more preferably 60-70, vol. % of oil, based on the total volume of the emulsion (although higher and lower concentrations also find use in emulsions described herein).

The oil in the nanoemulsion adjuvant of the invention can be any cosmetically or pharmaceutically acceptable oil. The oil can be volatile or non-volatile, and may be chosen from animal oil, vegetable oil, natural oil, synthetic oil, hydrocarbon oils, silicone oils, semi-synthetic derivatives thereof, and combinations thereof.

Suitable oils include, but are not limited to, mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, $C_{12-15}$ alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (*Simmondsia chinensis* seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, *eucalyptus* leaf oil, lemon grass leaf oil, *melaleuca* leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, *cassia* Bark oil, cinnamon bark oil, *sassafras* Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combinations thereof.

The oil may further comprise a silicone component, such as a volatile silicone component, which can be the sole oil in the silicone component or can be combined with other silicone and non-silicone, volatile and non-volatile oils. Suitable silicone components include, but are not limited to, methylphenylpolysiloxane, simethicone, dimethicone, phenyltrimethicone (or an organomodified version thereof), alkylated derivatives of polymeric silicones, cetyl dimethicone, lauryl trimethicone, hydroxylated derivatives of polymeric silicones, such as dimethiconol, volatile silicone oils, cyclic and linear silicones, cyclomethicone, derivatives of cyclomethicone, hexamethylcyclotrisiloxane, octamethylcyclotetrasiloxane, decamethylcyclopentasiloxane, volatile linear dimethylpolysiloxanes, isohexadecane, isoeicosane, isotetracosane, polyisobutene, isooctane, isododecane, semi-synthetic derivatives thereof, and combinations thereof.

The volatile oil can be the organic solvent, or the volatile oil can be present in addition to an organic solvent. Suitable volatile oils include, but are not limited to, a terpene, monoterpene, sesquiterpene, carminative, azulene, menthol, camphor, thujone, thymol, nerol, linalool, limonene, geraniol, perillyl alcohol, nerolidol, farnesol, ylangene, bisabolol, farnesene, ascaridole, *chenopodium* oil, citronellal, citral, citronellol, chamazulene, yarrow, guaiazulene, chamomile, semi-synthetic derivatives, or combinations thereof.

In one aspect of the invention, the volatile oil in the silicone component is different than the oil in the oil phase.

In some embodiments, the oil phase comprises 3-15, and preferably 5-10 vol. % of an organic solvent, based on the total volume of the emulsion. While the present invention is not limited to any particular mechanism, it is contemplated that the organic phosphate-based solvents employed in the emulsions serve to remove or disrupt the lipids in the membranes of the pathogens. Thus, any solvent that removes the sterols or phospholipids in the microbial membranes finds use in the methods of the present invention. Suitable organic solvents include, but are not limited to, organic phosphate based solvents or alcohols. In some preferred embodiments, non-toxic alcohols (e.g., ethanol) are used as a solvent. The oil phase, and any additional compounds provided in the oil phase, are preferably sterile and pyrogen free.

3. Surfactants and Detergents

In some embodiments, the emulsions further comprises a surfactant or detergent. In some preferred embodiments, the emulsion comprises from about 3 to 15%, and preferably about 10% of one or more surfactants or detergents (although other concentrations are also contemplated). While the present invention is not limited to any particular mechanism, it is contemplated that surfactants, when present in the emulsions, help to stabilize the emulsions. Both non-ionic (non-anionic) and ionic surfactants are contemplated. Additionally, surfactants from the BRIJ family of surfactants find use in the compositions of the present invention. The surfactant can be provided in either the aqueous or the oil phase. Surfactants suitable for use with the emulsions include a variety of anionic and nonionic surfactants, as well as other emulsifying compounds that are capable of promoting the formation of oil-in-water emulsions. In general, emulsifying compounds are relatively hydrophilic, and blends of emulsifying compounds can be used to achieve the necessary qualities. In some formulations, nonionic surfactants have advantages over ionic emulsifiers in that they are substantially more compatible with a broad pH range and often form more stable emulsions than do ionic (e.g., soap-type) emulsifiers.

The surfactant in the nanoemulsion adjuvant of the invention can be a pharmaceutically acceptable ionic surfactant, a pharmaceutically acceptable nonionic surfactant, a pharmaceutically acceptable cationic surfactant, a pharmaceutically acceptable anionic surfactant, or a pharmaceutically acceptable zwitterionic surfactant.

Exemplary useful surfactants are described in Applied Surfactants: Principles and Applications. Tharwat F. Tadros, Copyright 8 2005 WILEY-VCH Verlag GmbH & Co. KGaA, Weinheim ISBN: 3-527-30629-3), which is specifically incorporated by reference. Further, the surfactant can be a pharmaceutically acceptable ionic polymeric surfactant, a pharmaceutically acceptable nonionic polymeric surfactant, a pharmaceutically acceptable cationic polymeric surfactant, a pharmaceutically acceptable anionic polymeric surfactant, or a pharmaceutically acceptable zwitterionic polymeric surfactant. Examples of polymeric surfactants include, but are not limited to, a graft copolymer of a poly(methyl methacrylate) backbone with multiple (at least one) polyethylene oxide (PEO) side chain, polyhydroxystearic acid, an alkoxylated alkyl phenol formaldehyde condensate, a polyalkylene glycol modified polyester with fatty acid hydrophobes, a polyester, semi-synthetic derivatives thereof, or combinations thereof.

Surface active agents or surfactants, are amphipathic molecules that consist of a non-polar hydrophobic portion, usually a straight or branched hydrocarbon or fluorocarbon chain containing 8-18 carbon atoms, attached to a polar or ionic hydrophilic portion. The hydrophilic portion can be nonionic, ionic or zwitterionic. The hydrocarbon chain interacts weakly with the water molecules in an aqueous environment, whereas the polar or ionic head group interacts strongly with water molecules via dipole or ion-dipole interactions. Based on the nature of the hydrophilic group, surfactants are classified into anionic, cationic, zwitterionic, nonionic and polymeric surfactants.

Suitable surfactants include, but are not limited to, ethoxylated nonylphenol comprising 9 to 10 units of ethyleneglycol, ethoxylated undecanol comprising 8 units of ethyleneglycol, polyoxyethylene (20) sorbitan monolaurate, polyoxyethylene (20) sorbitan monopalmitate, polyoxyethylene (20) sorbitan monostearate, polyoxyethylene (20) sorbitan monooleate, sorbitan monolaurate, sorbitan monopalmitate, sorbitan monostearate, sorbitan monooleate, ethoxylated hydrogenated ricin oils, sodium laurylsulfate, a diblock copolymer of ethyleneoxide and propyleneoxide, Ethylene Oxide-Propylene Oxide Block Copolymers, and tetra-functional block copolymers based on ethylene oxide and propylene oxide, Glyceryl monoesters, Glyceryl caprate, Glyceryl caprylate, Glyceryl cocate, Glyceryl erucate, Glyceryl hydroxysterate, Glyceryl isostearate, Glyceryl lanolate, Glyceryl laurate, Glyceryl linolate, Glyceryl myristate, Glyceryl oleate, Glyceryl PABA, Glyceryl palmitate, Glyceryl ricinoleate, Glyceryl stearate, Glyceryl thiglycolate, Glyceryl dilaurate, Glyceryl dioleate, Glyceryl dimyristate, Glyceryl disterate, Glyceryl sesuioleate, Glyceryl stearate lactate, Polyoxyethylene cetyl/stearyl ether, Polyoxyethylene cholesterol ether, Polyoxyethylene laurate or dilaurate, Polyoxyethylene stearate or distearate, polyoxyethylene fatty ethers, Polyoxyethylene lauryl ether, Polyoxyethylene stearyl ether, polyoxyethylene myristyl ether, a steroid, Cholesterol, Betasitosterol, Bisabolol, fatty acid esters of alcohols, isopropyl myristate, Aliphati-isopropyl n-butyrate, Isopropyl n-hexanoate, Isopropyl n-decanoate, Isopropyl palmitate, Octyldodecyl myristate, alkoxylated alcohols, alkoxylated acids, alkoxylated amides, alkoxylated sugar derivatives, alkoxylated derivatives of natural oils and waxes, polyoxyethylene polyoxypropylene block copolymers, nonoxynol-14, PEG-8 laurate, PEG-6 Cocoamide, PEG-20 methylglucose sesquistearate, PEG40 lanolin, PEG-40 castor oil, PEG-40 hydrogenated castor oil, polyoxyethylene fatty ethers, glyceryl diesters, polyoxyethylene stearyl ether, polyoxyethylene myristyl ether, and polyoxyethylene lauryl ether, glyceryl dilaurate, glyceryl dimystate, glyceryl distearate, semi-synthetic derivatives thereof, or mixtures thereof.

Additional suitable surfactants include, but are not limited to, non-ionic lipids, such as glyceryl laurate, glyceryl myristate, glyceryl dilaurate, glyceryl dimyristate, semi-synthetic derivatives thereof, and mixtures thereof.

In additional embodiments, the surfactant is a polyoxyethylene fatty ether having a polyoxyethylene head group ranging from about 2 to about 100 groups, or an alkoxylated alcohol having the structure $R_5$—$(OCH_2\ CH_2)_y$—OH, wherein $R_5$ is a branched or unbranched alkyl group having from about 6 to about 22 carbon atoms and y is between about 4 and about 100, and preferably, between about 10 and about 100. Preferably, the alkoxylated alcohol is the species wherein $R_5$ is a lauryl group and y has an average value of 23. In a different embodiment, the surfactant is an alkoxylated alcohol which is an ethoxylated derivative of lanolin alcohol. Preferably, the ethoxylated derivative of lanolin alcohol is laneth-10, which is the polyethylene glycol ether of lanolin alcohol with an average ethoxylation value of 10.

Nonionic surfactants include, but are not limited to, an ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, Bis(polyethylene glycol bis(imidazoyl carbonyl)), nonoxynol-9, Bis(polyethylene glycol bis(imidazoyl carbonyl)), Brij® 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Decyl alpha-D-glucopyranoside, Decyl beta-D-maltopyranoside, n-Dodecanoyl-N-methylglucamide, n-Dodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O—(N-heptylcarbamoyl)-alpha-D-glucopyranoside, Nonaethylene glycol monododecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-beta-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from *Quillaja* bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tergitol, Tergitol, Type TMN-10, Tergitol, Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-100, Triton® X-114, Triton® X-165, Triton® X-305, Triton® X-405, Triton® X-45, Triton® X-705-70, TWEEN® 20, TWEEN® 21, TWEEN® 40, TWEEN® 60, TWEEN® 61, TWEEN® 65, TWEEN® 80, TWEEN® 81, TWEEN® 85, Tyloxapol, n-Undecyl beta-D-glucopyranoside, semi-synthetic derivatives thereof, or combinations thereof.

In addition, the nonionic surfactant can be a poloxamer. Poloxamers are polymers made of a block of polyoxyethylene, followed by a block of polyoxypropylene, followed by a block of polyoxyethylene. The average number of units of polyoxyethylene and polyoxypropylene varies based on the number associated with the polymer. For example, the smallest polymer, Poloxamer 101, consists of a block with an average of 2 units of polyoxyethylene, a block with an average of 16 units of polyoxypropylene, followed by a block with an average of 2 units of polyoxyethylene. Poloxamers range from colorless liquids and pastes to white solids. In cosmetics and personal care products, Poloxamers are used in the formulation of skin cleansers, bath products, shampoos, hair conditioners, mouthwashes, eye makeup remover and other skin and hair products. Examples of Poloxamers include, but are not limited to, Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 Benzoate, and Poloxamer 182 Dibenzoate.

Suitable cationic surfactants include, but are not limited to, a quaternary ammonium compound, an alkyl trimethyl ammonium chloride compound, a dialkyl dimethyl ammonium chloride compound, a cationic halogen-containing compound, such as cetylpyridinium chloride, Benzalkonium chloride, Benzalkonium chloride, Benzyldimethylhexadecylammonium chloride, Benzyldimethyltetradecylammonium chloride, Benzyldodecyldimethylammonium bromide, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Girard's reagent T, Hexadecyltrimethylammonium bromide, Hexadecyltrimethylammonium bromide, N,N',N'-Polyoxyethylene(10)-N-tallow-1,3-diaminopropane, Thonzonium bromide, Trimethyl(tetradecyl)ammonium bromide, 1,3,5-Triazine-1,3,5(2H,4H,6H)-triethanol, 1-Decanaminium, N-decyl-N, N-dimethyl-, chloride, Didecyl dimethyl ammonium chloride, 2-(2-(p-(Diisobutyl)cresosxy)ethoxy)ethyl dimethyl benzyl ammonium chloride, 2-(2-(p-(Diisobutyl)phenoxy)ethoxy)ethyl dimethyl benzyl ammonium chloride, Alkyl 1 or 3 benzyl-1-(2-hydroxethyl)-2-imidazolinium chloride, Alkyl bis(2-hydroxyethyl) benzyl ammonium chloride, Alkyl demethyl benzyl ammonium chloride, Alkyl dimethyl 3,4-dichlorobenzyl ammonium chloride (100% C12), Alkyl dimethyl 3,4-dichlorobenzyl ammonium chloride (50% C14, 40% C12, 10% C16), Alkyl dimethyl 3,4-dichlorobenzyl ammonium chloride (55% C14, 23% C12, 20% C16), Alkyl dimethyl benzyl ammonium chloride, Alkyl dimethyl benzyl ammonium chloride (100% C14), Alkyl dimethyl benzyl ammonium chloride (100% C16), Alkyl dimethyl benzyl ammonium chloride (41% C14, 28% C12), Alkyl dimethyl benzyl ammonium chloride (47% C12, 18% C14), Alkyl dimethyl benzyl ammonium chloride (55% C16, 20% C14), Alkyl dimethyl benzyl ammonium chloride (58% C14, 28% C16), Alkyl dimethyl benzyl ammonium chloride (60% C14, 25% C12), Alkyl dimethyl benzyl ammonium chloride (61% C11, 23% C14), Alkyl dimethyl benzyl ammonium chloride (61% C12, 23% C14), Alkyl dimethyl benzyl ammonium chloride (65% C12, 25% C14), Alkyl dimethyl benzyl ammonium chloride (67% C12, 24% C14), Alkyl dimethyl benzyl ammonium chloride (67% C12, 25% C14), Alkyl dimethyl benzyl ammonium chloride (90% C14, 5% C12), Alkyl dimethyl benzyl ammonium chloride (93% C14, 4% C12), Alkyl dimethyl benzyl ammonium chloride (95% C16, 5% C18), Alkyl dimethyl benzyl ammonium chloride, Alkyl didecyl dimethyl ammonium chloride, Alkyl dimethyl benzyl ammonium chloride, Alkyl dimethyl benzyl ammonium chloride (C12-16), Alkyl dimethyl benzyl ammonium chloride (C12-18), Alkyl dimethyl benzyl ammonium chloride, dialkyl dimethyl benzyl ammonium chloride, Alkyl dimethyl dimethybenzyl ammonium chloride, Alkyl dimethyl ethyl ammonium bromide (90% C14, 5% C16, 5% C12), Alkyl dimethyl ethyl ammonium bromide (mixed alkyl and alkenyl groups as in the fatty acids of soybean oil), Alkyl dimethyl ethylbenzyl ammonium chloride, Alkyl dimethyl ethylbenzyl ammonium chloride (60% C14), Alkyl dimethyl isopropylbenzyl ammonium chloride (50% C12, 30% C14, 17% C16, 3% C18), Alkyl trimethyl ammonium chloride (58% C18, 40% C16, 1% C14, 1% C12), Alkyl trimethyl ammonium chloride (90% C18, 10% C16), Alkyldimethyl(ethylbenzyl) ammonium chloride (C12-18), Di-(C8-10)-alkyl dimethyl ammonium chlorides, Dialkyl dimethyl ammonium chloride, Dialkyl methyl benzyl ammonium chloride, Didecyl dimethyl ammonium chloride, Diisodecyl dimethyl ammonium chloride, Dioctyl dimethyl ammonium chloride, Dodecyl bis (2-hydroxyethyl) octyl hydrogen ammonium chloride, Dodecyl dimethyl benzyl ammonium chloride, Dodecylcarbamoyl methyl dinethyl benzyl ammonium chloride, Heptadecyl hydroxyethylimidazolinium chloride, Hexahydro-1,3,5-tris(2-hydroxyethyl)-s-triazine, Hexahydro-1,3,5-tris(2-hydroxyethyl)-s-triazine, Myristalkonium chloride (and) Quat RNIUM 14, N,N-Dimethyl-2-hydroxypropylammonium chloride polymer, n-Tetradecyl dimethyl benzyl ammonium chloride monohydrate, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Quaternary ammonium compounds, dicoco alkyldimethyl, chloride, Trimethoxysily propyl dimethyl octadecyl ammonium chloride, Trimethoxysilyl quats, Trimethyl dodecylbenzyl ammonium chloride, semi-synthetic derivatives thereof, and combinations thereof.

Exemplary cationic halogen-containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), cetyltrimethylammonium bromide (CTAB), cetyidimethylethylammonium bromide, cetyltributylphosphonium bromide, dodecyltrimethylammonium bromide, and tetrad ecyltrimethylammonium bromide.

In particularly preferred embodiments, the cationic halogen containing compound is CPC, although the compositions of the present invention are not limited to formulation with an particular cationic containing compound.

Suitable anionic surfactants include, but are not limited to, a carboxylate, a sulphate, a sulphonate, a phosphate, chenodeoxycholic acid, chenodeoxycholic acid sodium salt, cholic acid, ox or sheep bile, Dehydrocholic acid, Deoxycholic acid, Deoxycholic acid, Deoxycholic acid methyl ester, Digitonin, Digitoxigenin, N,N-Dimethyldodecylamine N-oxide, Docusate sodium salt, Glycochenodeoxycholic acid sodium salt, Glycocholic acid hydrate, synthetic, Glycocholic acid sodium salt hydrate, synthetic, Glycodeoxycholic acid monohydrate, Glycodeoxycholic acid sodium salt, Glycodeoxycholic acid sodium salt, Glycolithocholic acid 3-sulfate disodium salt, Glycolithocholic acid ethyl ester, N-Lauroylsarcosine sodium salt, N-Lauroylsarcosine solution, N-Lauroylsarcosine solution, Lithium dodecyl sulfate, Lithium dodecyl sulfate, Lithium dodecyl sulfate, Lugol solution, Niaproof 4, Type 4, 1-Octanesulfonic acid sodium salt, Sodium 1-butanesulfonate, Sodium 1-decanesulfonate, Sodium 1-decanesulfonate, Sodium 1-dodecanesulfonate, Sodium 1-heptanesulfonate anhydrous, Sodium 1-heptanesulfonate anhydrous, Sodium 1-nonanesulfonate, Sodium 1-propanesulfonate monohydrate, Sodium 2-bromoethanesulfonate, Sodium cholate hydrate, Sodium choleate, Sodium deoxycholate, Sodium deoxycholate monohydrate, Sodium dodecyl sulfate, Sodium hexanesulfonate anhydrous, Sodium octyl sulfate, Sodium pentanesulfonate anhydrous, Sodium taurocholate, Taurochenodeoxycholic acid sodium salt, Taurodeoxycholic acid sodium salt monohydrate, Taurohyodeoxycholic acid sodium salt hydrate, Taurolithocholic acid 3-sulfate disodium salt, Tauroursodeoxycholic acid sodium salt, Trizma® dodecyl sulfate, TWEEN® 80, Ursodeoxycholic acid, semisynthetic derivatives thereof, and combinations thereof.

Suitable zwitterionic surfactants include, but are not limited to, an N-alkyl betaine, lauryl amindo propyl dimethyl betaine, an alkyl dimethyl glycinate, an N-alkyl amino propionate, CHAPS, minimum 98% (TLC), CHAPS, SigmaUltra, minimum 98% (TLC), CHAPS, for electrophoresis, minimum 98% (TLC), CHAPSO, minimum 98%, CHAPSO, SigmaUltra, CHAPSO, for electrophoresis, 3-(Decyldimethylammonio)propanesulfonate inner salt, 3-Dodecyldimethylammonio)propanesulfonate inner salt, SigmaUltra, 3-(Dodecyldimethylammonio)propanesulfonate inner salt, 3-(N,N-Dimethylmyristylammonio)propanesulfonate, 3-(N,N-Dimethyloctadecylammonio)propanesulfonate, 3-(N,N-Dimethyloctylammonio)propanesulfonate inner salt, 3-(N,N-Dimethylpalmitylammonio)propanesulfonate, semisynthetic derivatives thereof, and combinations thereof.

The present invention is not limited to the surfactants disclosed herein. Additional surfactants and detergents useful in the compositions of the present invention may be ascertained from reference works (e.g., including, but not limited to, McCutheon's Volume 1: Emulsions and Detergents—North American Edition, 2000) and commercial sources.

4. Cationic Halogens Containing Compounds

In some embodiments, the emulsions further comprise a cationic halogen containing compound. In some preferred embodiments, the emulsion comprises from about 0.5 to 1.0 wt. % or more of a cationic halogen containing compound, based on the total weight of the emulsion (although other concentrations are also contemplated). In preferred embodiments, the cationic halogen-containing compound is preferably premixed with the oil phase; however, it should be understood that the cationic halogen-containing compound may be provided in combination with the emulsion composition or in a distinct formulation. Suitable halogen containing compounds may be selected from compounds comprising chloride, fluoride, bromide and iodide ions. In preferred embodiments, suitable cationic halogen containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), and cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen-containing compound is CPC, although the compositions of the present invention are not limited to formulation with any particular cationic containing compound.

5. Germination Enhancers

In other embodiments of the present invention, the nanoemulsions further comprise a germination enhancer. In some preferred embodiments, the emulsions comprise from about 1 mM to 15 mM, and more preferably from about 5 mM to 10 mM of one or more germination enhancing compounds (although other concentrations are also contemplated). In preferred embodiments, the germination enhancing compound is provided in the aqueous phase prior to formation of the emulsion. The present invention contemplates that when germination enhancers are added to the nanoemulsion compositions, the sporicidal properties of the nanoemulsions are enhanced. The present invention further contemplates that such germination enhancers initiate sporicidal activity near neutral pH (between pH 6-8, and preferably 7). Such neutral pH emulsions can be obtained, for example, by diluting with phosphate buffer saline (PBS) or by preparations of neutral emulsions. The sporicidal activity of the nanoemulsion preferentially occurs when the spores initiate germination.

In specific embodiments, it has been demonstrated that the emulsions utilized in the vaccines of the present invention have sporicidal activity. While the present invention is not limited to any particular mechanism and an understanding of the mechanism is not required to practice the present invention, it is believed that the fusigenic component of the emulsions acts to initiate germination and before reversion to the vegetative form is complete the lysogenic component of the emulsion acts to lyse the newly germinating spore. These components of the emulsion thus act in concert to leave the spore susceptible to disruption by the emulsions. The addition of germination enhancer further facilitates the anti-sporicidal activity of the emulsions, for example, by speeding up the rate at which the sporicidal activity occurs.

Germination of bacterial endospores and fungal spores is associated with increased metabolism and decreased resistance to heat and chemical reactants. For germination to occur, the spore must sense that the environment is adequate to support vegetation and reproduction. The amino acid L-alanine stimulates bacterial spore germination (See e.g., Hills, J. Gen. Micro. 4:38 (1950); and Halvorson and Church, Bacteriol Rev. 21:112 (1957)). L-alanine and L-proline have also been reported to initiate fungal spore germination (Yanagita, Arch Mikrobiol 26:329 (1957)). Simple α-amino acids, such as glycine and L-alanine, occupy a central position in metabolism. Transamination or deamination of α-amino acids yields the glycogenic or ketogenic carbohydrates and the nitrogen needed for metabolism and growth. For example, transamination or deamination of L-alanine yields pyruvate, which is the end product of glycolytic metabolism (Embden-Meyerhof Pathway). Oxidation of pyruvate by pyruvate dehydrogenase complex yields acetyl-CoA, NADH, $H^+$, and $CO_2$. Acetyl-CoA is the initiator substrate for the tricarboxylic acid cycle (Kreb's Cycle), which in turns feeds the mitochondrial electron transport chain. Acetyl-CoA is also the ultimate carbon source for fatty acid synthesis as well as for sterol synthesis. Simple α-amino acids can provide the nitrogen, $CO_2$, glycogenic and/or ketogenic equivalents required for germination and the metabolic activity that follows.

In certain embodiments, suitable germination enhancing agents of the invention include, but are not limited to, α-amino acids comprising glycine and the L-enantiomers of alanine, valine, leucine, isoleucine, serine, threonine, lysine, phenylalanine, tyrosine, and the alkyl esters thereof. Additional information on the effects of amino acids on germination may be found in U.S. Pat. No. 5,510,104; herein incorporated by reference in its entirety. In some embodiments, a mixture of glucose, fructose, asparagine, sodium chloride (NaCl), ammonium chloride ($NH_4Cl$), calcium chloride ($CaCl_2$) and potassium chloride (KCl) also may be used. In particularly preferred embodiments of the present invention, the formulation comprises the germination enhancers L-alanine, $CaCl_2$, Inosine and $NH_4Cl$. In some embodiments, the compositions further comprise one or more common forms of growth media (e.g., trypticase soy broth, and the like) that additionally may or may not itself comprise germination enhancers and buffers.

The above compounds are merely exemplary germination enhancers and it is understood that other known germination enhancers will find use in the nanoemulsions utilized in some embodiments of the present invention. A candidate germination enhancer should meet two criteria for inclusion in the compositions of the present invention: it should be capable of being associated with the emulsions disclosed herein and it should increase the rate of germination of a target spore when incorporated in the emulsions disclosed herein. One skilled in the art can determine whether a particular agent has the desired function of acting as an germination enhancer by applying such an agent in combination with the nanoemulsions disclosed herein to a target and comparing the inactivation of the target when contacted by the admixture with inactivation of like targets by the composition of the present invention without the agent. Any agent that increases germination, and thereby decreases or inhibits the growth of the organisms, is considered a suitable enhancer for use in the nanoemulsion compositions disclosed herein.

In still other embodiments, addition of a germination enhancer (or growth medium) to a neutral emulsion composition produces a composition that is useful in inactivating bacterial spores in addition to enveloped viruses, Gram negative bacteria, and Gram positive bacteria for use in the vaccine compositions of the present invention.

6. Interaction Enhancers

In still other embodiments, nanoemulsions comprise one or more compounds capable of increasing the interaction of the compositions (i.e., "interaction enhancer" (e.g., with target pathogens (e.g., the cell wall of Gram negative bacteria such as *Vibrio, Salmonella, Shigella* and *Pseudomonas*)). In preferred embodiments, the interaction enhancer is preferably premixed with the oil phase; however, in other embodiments the interaction enhancer is provided in combination with the compositions after emulsification. In certain preferred embodiments, the interaction enhancer is a chelating agent (e.g., ethylenediaminetetraacetic acid (EDTA) or ethylenebis(oxyethylenenitrilo)tetraacetic acid (EGTA) in a buffer (e.g., tris buffer)). It is understood that chelating agents are merely exemplary interaction enhancing compounds. Indeed, other agents that increase the interaction of the nanoemulsions used in some embodiments of the present invention (e.g., with microbial agents, pathogens, vaccines, etc.) are contemplated. In particularly preferred embodiments, the interaction enhancer is at a concentration of about 50 to about 250 μM. One skilled in the art will be able to determine whether a particular agent has the desired function of acting as an interaction enhancer by applying such an agent in combination with the compositions of the present invention to a target and comparing the inactivation of the target when contacted by the admixture with inactivation of like targets by the composition of the present invention without the agent. Any agent that increases the interaction of an emulsion with bacteria and thereby decreases or inhibits the growth of the bacteria, in comparison to that parameter in its absence, is considered an interaction enhancer.

In some embodiments, the addition of an interaction enhancer to nanoemulsion produces a composition that is useful in inactivating enveloped viruses, some Gram positive bacteria and some Gram negative bacteria for use in a vaccine composition.

7. Quaternary Ammonium Compounds

In some embodiments, nanoemulsions of the present invention include a quaternary ammonium containing compound. Exemplary quaternary ammonium compounds include, but are not limited to, Alkyl dimethyl benzyl ammonium chloride, didecyl dimethyl ammonium chloride, Alkyl dimethyl benzyl and dialkyl dimethyl ammonium chloride, N,N-Dimethyl-2-hydroxypropylammonium chloride polymer, Didecyl dimethyl ammonium chloride, n-Alkyl dimethyl benzyl ammonium chloride, n-Alkyl dimethyl ethylbenzyl ammonium chloride, Dialkyl dimethyl ammonium chloride, n-Alkyl dimethyl benzyl ammonium chloride, n-Tetradecyl dimethyl benzyl ammonium chloride monohydrate, n-Alkyl dimethyl benzyl ammonium chloride, Dialkyl dimethyl ammonium chloride, Hexahydro-1,3,5-tris (2-hydroxyethyl)-s-triazine, Myristalkonium chloride (and) Quat RNIUM 14, Alkyl bis(2-hydroxyethyl) benzyl ammonium chloride, Alkyl demethyl benzyl ammonium chloride, Alkyl dimethyl 3,4-dichlorobenzyl ammonium chloride, Alkyl dimethyl benzyl ammonium chloride, Alkyl dimethyl benzyl dimethylbenzyl ammonium, Alkyl dimethyl dimethybenzyl ammonium chloride, Alkyl dimethyl ethyl ammonium bromide, Alkyl dimethyl ethyl ammonium bromide, Alkyl dimethyl ethylbenzyl ammonium chloride, Alkyl dimethyl isopropylbenzyl ammonium chloride, Alkyl trimethyl ammonium chloride, Alkyl 1 or 3 benzyl-1-(2-hydroxethyl)-2-imidazolinium chloride, Dialkyl methyl benzyl ammonium chloride, Dialkyl dimethyl ammonium chloride, Didecyl dimethyl ammonium chloride, 2-(2-(p-(Diisobutyl)cresosxy)ethoxy)ethyl dimethyl benzyl ammonium chloride, 2-(2-(p-(Diisobutyl)phenoxy)ethoxy)ethyl dimethyl benzyl ammonium chloride, Dioctyl dimethyl ammonium chloride, Dodecyl bis (2-hydroxyethyl) octyl hydrogen ammonium chloride, Dodecyl dimethyl benzyl ammonium chloride, Dodecylcarbamoyl methyl dinethyl benzyl ammonium chloride, Heptadecyl hydroxyethylimidazolinium chloride, Hexahydro-1,3,5-tris(2-hydroxyethyl)- s-triazine, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Quaternary ammonium compounds, dicoco alkyldimethyl, chloride, Trimethoxysilyl quats, and Trimethyl dodecylbenzyl ammonium chloride.

8. Other Components

In some embodiments, a nanoemulsion adjuvant composition comprises one or more additional components that provide a desired property or functionality to the nanoemulsions. These components may be incorporated into the aqueous phase or the oil phase of the nanoemulsions and/or may be added prior to or following emulsification. For example, in some embodiments, the nanoemulsions further comprise phenols (e.g., triclosan, phenyl phenol), acidifying agents (e.g., citric acid (e.g., 1.5-6%), acetic acid, lemon juice), alkylating agents (e.g., sodium hydroxide (e.g., 0.3%)), buffers (e.g., citrate buffer, acetate buffer, and other buffers useful to maintain a specific pH), and halogens (e.g., polyvinylpyrrolidone, sodium hypochlorite, hydrogen peroxide).

Exemplary techniques for making a nanoemulsion are described below. Additionally, a number of specific, although exemplary, formulation recipes are also set forth herein.

In some embodiments, a nanoemulsion adjuvant is administered to a subject before, concurrent with or after administration of a composition comprising an immunogen (e.g., a pathogen and/or pathogen component (e.g., purified, isolated and/or recombinant pathogen peptide and/or protein)). The invention is not limited to the use of any one specific type of composition comprising an immunogen. Indeed, a variety of compositions comprising an immunogen (e.g., utilized for generating an immune response (e.g., for use as a vaccine)) may be utilized with a nanoemulsion adjuvant of the invention. In some embodiments, the composition comprising an immunogen comprises pathogens (e.g., killed pathogens), pathogen components or isolated, purified and/or recombinant parts thereof. Accordingly, in some embodiments, the composition comprising an immunogen comprises a bacterial pathogen or pathogen component including, but not limited to, *Bacillus cereus, Bacillus circulans* and *Bacillus megaterium, Bacillus anthracis*, bacteria of the genus *Brucella, Vibrio cholera, Coxiella burnetii, Francisella tularensis, Chlamydia psittaci, Ricinus communis, Rickettsia prowazekii*, bacterial of the genus *Salmonella* (e.g., *S. typhi*), bacteria of the genus *Shigella, Cryptosporidium parvum, Burkholderia pseudomallei, Clostridium perfringens, Clostridium botulinum, Vibrio cholerae, Streptococcus pyogenes, Streptococcus agalactiae, Streptococcus pneumonia, Staphylococcus aureus, Neisseria gonorrhea, Haemophilus influenzae, Escherichia coli, Salmonella typhimurium, Shigella dysenteriae, Proteus mirabilis, Pseudomonas aeruginosa, Yersinia pestis, Yersinia enterocolitica*, and *Yersinia pseudotuberculosis*). In other embodiments, the composition comprising an immunogen comprises a viral pathogen or pathogen component including, but not limited to, influenza A virus, avian influenza virus, H5N1 influenza virus, West Nile virus, SARS virus, Marburg virus, Arenaviruses, Nipah virus, alphaviruses, filoviruses, herpes simplex virus I, herpes simplex virus II, *sendai, sindbis*, vaccinia, parvovirus, human immunodeficiency virus, hepatitis B virus, hepatitis C virus, hepatitis A virus, cytomegalovirus, human papilloma virus, picornavirus, hantavirus, junin virus, and ebola virus). In still further embodiments, the composition comprising an immunogen comprises a fungal pathogen or pathogen component, including, but not limited to, *Candida albicnas* and *parapsilosis, Aspergillus fumigatus* and *niger, Fusarium* spp, *Trychophyton* spp.

In some embodiments, a nanoemulsion adjuvant is administered to a subject before, concurrent with or after administration of a vaccine containing peptides (e.g., one generally well known in the art, as exemplified by U.S. Pat. Nos. 4,601,903; 4,599,231; 4,599,230; and 4,596,792; each of which is hereby incorporated by reference).

Formulation Techniques

Nanoemulsions of the present invention can be formed using classic emulsion forming techniques. In brief, the oil phase is mixed with the aqueous phase under relatively high shear forces (e.g., using high hydraulic and mechanical forces) to obtain an oil-in-water nanoemulsion. The emulsion is formed by blending the oil phase with an aqueous phase on a volume-to-volume basis ranging from about 1:9 to 5:1, preferably about 5:1 to 3:1, most preferably 4:1, oil phase to aqueous phase. The oil and aqueous phases can be blended using any apparatus capable of producing shear forces sufficient to form an emulsion such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, and U.S. Patent Application Nos. 20070036831, 20060251684, and 20050208083, herein incorporated by reference in their entireties.

In preferred embodiments, compositions used in the methods of the present invention comprise droplets of an oily discontinuous phase dispersed in an aqueous continuous phase, such as water. In preferred embodiments, nanoemulsions of the present invention are stable, and do not decompose even after long storage periods (e.g., greater than one or more years). Furthermore, in some embodiments, nanoemulsions are stable (e.g., in some embodiments for greater than 3 months, in some embodiments for greater than 6 months, in some embodiments for greater than 12 months, in some embodiments for greater than 18 months) after combination with an immunogen. In preferred embodiments, nanoemulsions of the present invention are non-toxic and safe when administered (e.g., via spraying or contacting mucosal surfaces, swallowed, inhaled, etc.) to a subject.

In some embodiments, a portion of the emulsion may be in the form of lipid structures including, but not limited to, unilamellar, multilamellar, and paucliamellar lipid vesicles, micelles, and lamellar phases.

In general, the preferred non-toxic nanoemulsions are characterized by the following: they are approximately 200-800 nm in diameter, although both larger and smaller diameter nanoemulsions are contemplated; the charge depends on the ingredients; they are stable for relatively long periods of time (e.g., up to two years), with preservation of their biocidal activity; they are non-irritant and non-toxic compared to their individual components due, at least in part, to their oil contents that markedly reduce the toxicity of the detergents and the solvents; they are effective at concentrations as low as, for example, 0.1%; they have antimicrobial activity against most vegetative bacteria (including Gram-positive and Gram-negative organisms), fungi, and enveloped and nonenveloped viruses in 15 minutes (e.g., 99.99% killing); and they have sporicidal activity in 1-4 hours (e.g., 99.99% killing) when produced with germination enhancers.

The present invention is not limited by the type of subject administered a composition of the present invention. The present invention is not limited by the particular formulation of a composition comprising a nanoemulsion adjuvant of the present invention. Indeed, a composition comprising a nanoemulsion of the present invention may comprise one or more different agents in addition to the nanoemulsion. These agents or cofactors include, but are not limited to, adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a composition comprising a nanoemulsion of the present invention comprises an agent and/or co-factor that enhance the ability of the nanoemulsion to induce an immune response. In some preferred embodiments, the presence of one or more co-factors or agents reduces the amount of nanoemulsion required for inducing an immune response. The present invention is not limited by the type of co-factor or agent used in a therapeutic agent of the present invention.

In some embodiments, a co-factor or agent used in a nanoemulsion composition is a bioactive agent. For example, in some embodiments, the bioactive agent may be a bioactive agent useful in a cell (e.g., a cell expressing a CFTR). Bioactive agents, as used herein, include diagnostic agents such as radioactive labels and fluorescent labels. Bioactive agents also include molecules affecting the metabolism of a cell (e.g., a cell expressing a CFTR), including peptides, nucleic acids, and other natural and synthetic drug molecules. Bioactive agents include, but are not limited to, adrenergic agent; adrenocortical steroid; adrenocortical suppressant; alcohol deterrent; aldosterone antagonist; amino acid; ammonia detoxicant; anabolic; analeptic; analgesic; androgen; anesthesia, adjunct to; anesthetic; anorectic; antagonist; anterior pituitary suppressant; anthelmintic; anti-acne agent; anti-adrenergic; anti-allergic; anti-amebic; anti-androgen; anti-anemic; anti-anginal; anti-anxiety; anti-arthritic; anti-asthmatic; anti-atherosclerotic; antibacterial; anticholelithic; anticholelithogenic; anticholinergic; anticoagulant; anticoccidal; anticonvulsant; antidepressant; antidiabetic; antidiarrheal; antidiuretic; antidote; anti-emetic; anti-epileptic; anti-estrogen; antifibrinolytic; antifungal; antiglaucoma agent; antihemophilic; antihemorrhagic; antihistamine; antihyperlipidemia; antihyperlipoproteinemic; antihypertensive; antihypotensive; anti-infective; anti-infective, topical; anti-inflammatory; antikeratinizing agent; antimalarial; antimicrobial; antimigraine; antimitotic; antimycotic, antinauseant, antineoplastic, antineutropenic, antiobessional agent; antiparasitic; antiparkinsonian; antiperistaltic, antipneumocystic; antiproliferative; antiprostatic hypertrophy; antiprotozoal; antipruritic; antipsychotic; antirheumatic; antischistosomal; antiseborrheic; antisecretory; antispasmodic; antithrombotic; antitussive; anti-ulcerative; anti-urolithic; antiviral; appetite suppressant; benign prostatic hyperplasia therapy agent; blood glucose regulator; bone resorption inhibitor; bronchodilator; carbonic anhydrase inhibitor; cardiac depressant; cardioprotectant; cardiotonic; cardiovascular agent; choleretic; cholinergic; cholinergic agonist; cholinesterase deactivator; coccidiostat; cognition adjuvant; cognition enhancer; depressant; diagnostic aid; diuretic; dopaminergic agent; ectoparasiticide; emetic; enzyme inhibitor; estrogen; fibrinolytic; fluorescent agent; free oxygen radical scavenger; gastrointestinal motility effector; glucocorticoid; gonad-stimulating principle; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; impotence therapy adjunct; inhibitor; keratolytic; LHRH agonist; liver disorder treatment; luteolysin; memory adjuvant; mental performance enhancer; mood regulator; mucolytic; mucosal protective agent; mydriatic; nasal decongestant; neuromuscular blocking agent; neuroprotective; NMDA antagonist; non-hormonal sterol derivative; oxytocic; plasminogen activator; platelet activating factor antagonist; platelet aggregation inhibitor; post-stroke and post-head trauma treatment; potentiator; progestin; prostaglandin; prostate growth inhibitor; prothyrotropin; psychotropic; pulmonary surface; radioactive agent; regulator; relaxant; repartitioning agent; scabicide; sclerosing agent; sedative; sedative-hypnotic; selective adenosine A1 antagonist; serotonin antagonist; serotonin inhibitor; serotonin receptor antagonist; steroid; stimulant; suppressant; symptomatic multiple sclerosis; synergist; thyroid hormone; thyroid inhibitor; thyromimetic; tranquilizer; amyotrophic lateral sclerosis agent; cerebral ischemia agent; Paget's disease agent; unstable angina agent; uricosuric; vasoconstrictor; vasodilator; vulnerary; wound healing agent; xanthine oxidase inhibitor.

Molecules useful as antimicrobials can be delivered by the methods and compositions of the invention. Antibiotics that may find use in co-administration with a composition comprising a nanoemulsion of the present invention include, but are not limited to, agents or drugs that are bactericidal and/or bacteriostatic (e.g., inhibiting replication of bacteria or inhibiting synthesis of bacterial components required for survival of the infecting organism), including, but not limited to, almecillin, amdinocillin, amikacin, amoxicillin, amphomycin, amphotericin B, ampicillin, azacitidine, azaserine, azithromycin, azlocillin, aztreonam, bacampicillin, bacitracin, benzyl penicilloyl-polylysine, bleomycin, candicidin, capreomycin, carbenicillin, cefaclor, cefadroxil, cefamandole, cefazoline, cefdinir, cefepime, cefixime, cefinenoxime, cefinetazole, cefodizime, cefonicid, cefoperazone, ceforanide, cefotaxime, cefotetan, cefotiam, cefoxitin, cefpiramide, cefpodoxime, cefprozil, cefsulodin, ceftazidime, ceftibuten, ceftizoxime, ceftriaxone, cefuroxime, cephacetrile, cephalexin, cephaloglycin, cephaloridine, cephalothin, cephapirin, cephradine, chloramphenicol, chlortetracycline, cilastatin, cinnamycin, ciprofloxacin, clarithromycin, clavulanic acid, clindamycin, clioquinol, cloxacillin, colistimethate, colistin, cyclacillin, cycloserine, cyclosporine, cyclo-(Leu-Pro), dactinomycin, dalbavancin, dalfopristin, daptomycin, daunorubicin, demeclocycline, detorubicin, dicloxacillin, dihydrostreptomycin, dirithromycin, doxorubicin, doxycycline, epirubicin, erythromycin, eveminomycin, floxacillin, fosfomycin, fusidic acid, gemifloxacin, gentamycin, gramicidin, griseofulvin, hetacillin, idarubicin, imipenem, iseganan, ivermectin, kanamycin, laspartomycin, linezolid, linocomycin, loracarbef, magainin, meclocycline, meropenem, methacycline, methicillin, mezlocillin, minocycline, mitomycin, moenomycin, moxalactam, moxifloxacin, mycophenolic acid, nafcillin, natamycin, neomycin, netilmicin, niphimycin, nitrofurantoin, novobiocin, oleandomycin, oritavancin, oxacillin, oxytetracycline, paromomycin, penicillamine, penicillin G, penicillin V, phenethicillin, piperacillin, plicamycin, polymyxin B, pristinamycin, quinupristin, rifabutin, rifampin, rifamycin, rolitetracycline, sisomicin, spectrinomycin, streptomycin, streptozocin, sulbactam, sultamicillin, tacrolimus, tazobactam, teicoplanin, telithromycin, tetracycline, ticarcillin, tigecycline, tobramycin, troleandomycin, tunicamycin, tyrthricin, vancomycin, vidarabine, viomycin, virginiamycin, BMS-284,756, L-749,345, ER-35,786, S-4661, L-786,392, MC-02479, Pep5, RP 59500, and TD-6424.

In some embodiments, a composition comprising a nanoemulsion of the present invention comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives are contemplated to be useful in the present invention including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. Although an understanding of the mechanism is not necessary to practice the present invention and the present invention is not limited to any particular mechanism of action, in some embodiments, use of a mucoadhesive (e.g., in a composition comprising a nanoemulsion) enhances an immune response in a host subject due to an increase in duration and/or amount of exposure to the nanoemulsion that a subject experiences when a mucoadhesive is used compared to the duration and/or amount of exposure to the nanoemulsion in the absence of using the mucoadhesive.

In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono- ordi-glycerides. In addition, fatty acids such as oleic acid find use in the preparation of injectables. Carrier formulations suitable for mucosal, pulmonary, subcutaneous, intramuscular, intraperitoneal, intravenous, or administration via other routes may be found in Remington's Pharmaceutical Sciences, Mack Publishing Company, Easton, Pa.

A composition comprising a nanoemulsion adjuvant of the present invention can be used therapeutically or as a prophylactic. A composition comprising a nanoemulsion of the present invention can be administered to a subject via a number of different delivery routes and methods.

For example, the compositions of the present invention can be administered to a subject (e.g., mucosally or by pulmonary route) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal or pulmonary surface); being placed on or impregnated onto a nasal and/or pulmonary applicator and applied; being applied by a controlled-release mechanism; applied using a nebulizer, aerosolized, being applied as a liposome; or being applied on a polymer.

In some embodiments, compositions of the present invention are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal and pulmonary techniques), as well as European Publication No. 517,565 and Illum et al., J. Controlled Rel., 1994, 29:133-141 (e.g., for techniques of intranasal administration), each of which is hereby incorporated by reference in its entirety). The present invention is not limited by the route of administration.

Methods of intranasal and pulmonary administration are well known in the art, including the administration of a droplet or spray form of the nanoemulsion into the nasopharynx of a subject to be treated. In some embodiments, a nebulized or aerosolized composition comprising a nanoemulsion is provided. Enteric formulations such as gastro resistant capsules for oral administration, suppositories for rectal or vaginal administration may also form part of this invention. Compositions of the present invention may also be administered via the oral route. Under these circumstances, a composition comprising a nanoemulsion may comprise a pharmaceutically acceptable excipient and/or include alkaline buffers, or enteric capsules. Formulations for nasal delivery may include those with dextran or cyclodextran and saponin as an adjuvant.

In preferred embodiments, a nanoemulsion of the present invention is administered via a pulmonary delivery route and/or means. In some embodiments, an aqueous solution containing the nanoemulsion is gently and thoroughly mixed to form a solution. The solution is sterile filtered (e.g., through a 0.2 micron filter) into a sterile, enclosed vessel. Under sterile conditions, the solution is passed through an appropriately small orifice to make droplets (e.g., between 0.1 and 10 microns).

The particles may be administered using any of a number of different applicators. Suitable methods for manufacture and administration are described in the following U.S. Pat. Nos. 6,592,904; 6,518,239; 6,423,344; 6,294,204; 6,051,256 and 5,997,848 to INHALE (now NEKTAR); and U.S. Pat. No. 5,985,309; RE37,053; U.S. Pat. Nos. 6,436,443; 6,447,753; 6,503,480; and 6,635,283, to Edwards, et al. (MIT, AIR), each of which is hereby incorporated Thus, in some embodiments, compositions of the present invention are administered by pulmonary delivery. For example, a composition of the present invention can be delivered to the lungs of a subject (e.g., a human) via inhalation (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. III, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colo.; Debs, et al. J. Immunol. 1988; 140:3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)). In some embodiments, a composition comprising a nanoemulsion is administered to a subject by more than one route or means (e.g., administered via pulmonary route as well as a mucosal route).

Further contemplated for use in the practice of this invention are a wide range of mechanical devices designed for pulmonary and/or nasal mucosal delivery of pharmaceutical agents including, but not limited to, nebulizers, metered dose inhalers, and powder inhalers, all of which are familiar to those skilled in the art. Some specific examples of commercially available devices suitable for the practice of this invention are the ULTRAVENT nebulizer (Mallinckrodt Inc., St. Louis, Mo.); the ACORN II nebulizer (Marquest Medical Products, Englewood, Colo.); the VENTOLIN metered dose inhaler (Glaxo Inc., Research Triangle Park, N.C.); and the SPINHALER powder inhaler (Fisons Corp., Bedford, Mass.). All such devices require the use of formulations suitable for dispensing of the therapeutic agent. Typically, each formulation is specific to the type of device employed and may involve the use of an appropriate propellant material, in addition to the usual diluents, adjuvants, surfactants, carriers and/or other agents useful in therapy. Also, the use of liposomes, microcapsules or microspheres, inclusion complexes, or other types of carriers is contemplated.

Thus, in some embodiments, a composition comprising a nanoemulsion of the present invention may be used to protect and/or treat a subject susceptible to, or suffering from, a disease by means of administering compositions comprising a nanoemulsion by mucosal, intramuscular, intraperitoneal, intradermal, transdermal, pulmonary, intravenous, subcutaneous or other route of administration described herein. Methods of systemic administration of the nanoemulsion and/or agent co-administered with the nanoemulsion may include conventional syringes and needles, or devices designed for ballistic delivery (See, e.g., WO 99/27961, hereby incorporated by reference), or needleless pressure liquid jet device (See, e.g., U.S. Pat. Nos. 4,596,556; 5,993,412, each of which are hereby incorporated by reference), or transdermal patches (See, e.g., WO 97/48440; WO 98/28037, each of which are hereby incorporated by reference). In some embodiments, the present invention provides a delivery device for systemic administration, pre-filled with the nanoemulsion composition of the present invention.

As described above, the present invention is not limited by the type of subject administered a composition of the present invention. Indeed, a wide variety of subjects are contemplated to be benefited from administration of a composition of the present invention. In preferred embodiments, the subject is a human. In some embodiments, human subjects are of any age (e.g., adults, children, infants, etc.) that have been or are likely to become exposed to a microorganism or allergic substance or material. In some embodiments, the human subjects are subjects that are more likely to receive a direct exposure to pathogenic microorganisms or that are more likely to display signs and symptoms of disease after exposure to a pathogen (e.g., subjects with CF or asthma, subjects in the armed forces, government employees, frequent travelers, persons attending or working in a school or daycare, health care workers, an elderly person, an immunocompromised person, and emergency service employees (e.g., police, fire, EMT employees)). In some embodiments, any one or all members of the general public can be administered a composition of the present invention (e.g., to prevent the occurrence or spread of disease). For example, in some embodiments, compositions and methods of the present invention are utilized to treat a group of people (e.g., a population of a region, city, state and/or country) for their own health (e.g., to prevent or treat disease) and/or to prevent or reduce the risk of disease spread from animals (e.g., birds, cattle, sheep, pigs, etc.) to humans. In some embodiments, the subjects are non-human mammals (e.g., pigs, cattle, goats, horses, sheep, or other livestock; or mice, rats, rabbits or other animal). In some embodiments, compositions and methods of the present invention are utilized in research settings (e.g., with research animals).

A composition comprising a nanoemulsion of the present invention can be administered (e.g., to a subject (e.g., via pulmonary and/or mucosal route)) as a therapeutic or as a prophylactic to prevent microbial infection.

The compositions of the present invention may additionally contain other adjunct components conventionally found in pharmaceutical compositions. Thus, for example, the compositions may contain additional, compatible, pharmaceutically-active materials such as, for example, antipyruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, preferably do not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the nanoemulsion. In some embodiments, nanoemulsion compositions of the present invention are administered in the form of a pharmaceutically acceptable salt. When used the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include, but are not limited to, acetic acid and a salt (1-2% w/v); citric acid and a salt (1-3% w/v); boric acid and a salt (0.5-2.5% w/v); and phosphoric acid and a salt (0.8-2% w/v). Suitable preservatives may include benzalkonium chloride (0.003-0.03% w/v); chlorobutanol (0.3-0.9% w/v); parabens (0.01-0.25% w/v) and thimerosal (0.004-0.02% w/v).

In some embodiments, a composition comprising a nanoemulsion adjuvant is co-administered with one or more antibiotics. For example, one or more antibiotics may be administered with, before and/or after administration of a composition comprising a nanoemulsion. The present invention is not limited by the type of antibiotic co-administered. Indeed, a variety of antibiotics may be co-administered including, but not limited to, β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams,), β-lactamase inhibitors, vancomycin, aminoglycosides and spectinomycin, tetracyclines, chloramphenicol, erythromycin, lincomycin, clindamycin, rifampin, metronidazole, polymyxins, doxycycline, quinolones (e.g., ciprofloxacin), sulfonamides, trimethoprim, and quinolines.

A wide variety of antimicrobial agents are currently available for use in treating bacterial, fungal and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erthromycin and clindamycin); agents that alter protein synthesis and lead to cell death (e.g., aminoglycosides); agents that affect nucleic acid metabolism (e.g., the rifamycins and the quinolones); the antimetabolites (e.g., trimethoprim and sulfonamides); and the nucleic acid analogues such as zidovudine, ganciclovir, vidarabine, and acyclovir which act to inhibit viral enzymes essential for DNA synthesis. Various combinations of antimicrobials may be employed.

The present invention also includes methods involving co-administration of a composition comprising a nanoemulsion adjuvant with one or more additional active and/or anti-infective agents. In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered (e.g., antibiotics, a second type of nanoemulsion, etc.) can be any of the well-known agents in the art, including, but not limited to, those that are currently in clinical use.

In some embodiments, a composition comprising a nanoemulsion is administered to a subject via more than one route. For example, a subject may benefit from receiving mucosal administration (e.g., nasal administration or other mucosal routes described herein) and, additionally, receiving one or more other routes of administration (e.g., pulmonary administration (e.g., via a nebulizer, inhaler, or other methods described herein.

Other delivery systems can include time-release, delayed release or sustained release delivery systems. Such systems can avoid repeated administrations of the compositions, increasing convenience to the subject and a physician. Many types of release delivery systems are available and known to those of ordinary skill in the art. They include polymer based systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, hereby incorporated by reference. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, each of which is hereby incorporated by reference and (b) diffusional systems in which an active component permeates at a controlled rate from a polymer such as described in U.S. Pat. Nos. 3,854,480, 5,133,974 and 5,407,686, each of which is hereby incorporated by reference. In addition, pump-based hardware delivery systems can be used, some of which are adapted for implantation.

The present invention is not limited by the amount of nanoemulsion used. The amount will vary depending upon which specific nanoemulsion(s) is/are employed, and can vary from subject to subject, depending on a number of factors including, but not limited to, the species, age and general condition (e.g., health) of the subject, and the mode of administration. Procedures for determining the appropriate amount of nanoemulsion administered to a subject to induce an immune response in a subject can be readily determined using known means by one of ordinary skill in the art.

In some embodiments, it is expected that each dose (e.g., of a composition comprising a nanoemulsion comprises 1-40% nanoemulsion, in some embodiments, 20% nanoemulsion, in some embodiments less than 20% (e.g., 15%, 10%, 8%, 5% or less nanoemulsion), and in some embodiments greater than 20% nanoemulsion (e.g., 25%, 30%, 35%, 40% or more nanoemulsion). An optimal amount for a particular administration can be ascertained by one of skill in the art using standard studies involving observation of immune responses described herein.

In some embodiments, it is expected that each dose (e.g., of a composition comprising a nanoemulsion is from 0.001 to 40% or more (e.g., 0.001-10%, 0.5-5%, 1-3%, 2%, 6%, 10%, 15%, 20%, 30%, 40% or more) by weight nanoemulsion.

Similarly, the present invention is not limited by the duration of time a nanoemulsion is administered to a subject (e.g., to induce immune priming). In some embodiments, a nanoemulsion is administered one or more times (e.g. twice, three times, four times or more) daily. In some embodiments, a composition comprising a nanoemulsion is administered one or more times a day until a suitable level of immune response is generated and/or the immune response is sustained. In some embodiments, a composition comprising a nanoemulsion of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.5-50% of the nanoemulsion present in the concentrated composition. Concentrated compositions are contemplated to be useful in a setting in which large numbers of subjects may be administered a composition of the present invention (e.g., a hospital). In some embodiments, a composition comprising a nanoemulsion of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

Dosage units may be proportionately increased or decreased based on several factors including, but not limited to, the weight, age, and health status of the subject. In addition, dosage units may be increased or decreased for subsequent administrations.

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Compositions and methods of the present invention are also useful in studying and optimizing nanoemulsions, immunogens, and other components and for screening for new components. Thus, it is not intended that the present invention be limited to any particular subject and/or application setting.

The formulations can be tested in vivo in a number of animal models developed for the study of pulmonary, mucosal and other routes of delivery. As is readily apparent, the compositions of the present invention are useful for preventing and/or treating a wide variety of diseases and infections caused by viruses, bacteria, parasites, and fungi. Not only can the compositions be used prophylactically or therapeutically, as described above, the compositions can also be used in order to prepare antibodies, both polyclonal and monoclonal (e.g., for diagnostic purposes), as well as for immunopurification of an antigen of interest.

In one embodiment, the adjuvant mixtures of the present invention are useful for the production of immunogenic compositions that can be used to generate antigen-specific antibodies that are useful in the specific identification of that antigen in an immunoassay according to a diagnostic embodiment. Such immunoassays include enzyme-linked immunosorbant assays (ELISA), RIAs and other non-enzyme linked antibody binding assays or procedures known in the art. In ELISA assays, the antigen-specific antibodies are immobilized onto a selected surface; for example, the wells of a polystyrene microtiter plate. After washing to remove incompletely adsorbed antibodies, a nonspecific protein, such as a solution of bovine serum albumin (BSA) or casein, that is known to be antigenically neutral with regard to the test sample may be bound to the selected surface. This allows for blocking of nonspecific adsorption sites on the immobilizing surface and thus reduces the background caused by nonspecific bindings of antigens onto the surface. The immobilizing surface is then contacted with a sample, such as clinical or biological materials, to be tested in a manner conducive to immune complex (antigen/antibody) formation. This may include diluting the sample with diluents, such as BSA, bovine gamma globulin (BGG) and/or phosphate buffered saline (PBS)/Tween. The sample is then allowed to incubate for from about 2 to 4 hours, at temperatures such as of the order of about 25-37° C. Following incubation, the sample-contacted surface is washed to remove non-immunocomplexed material. The washing procedure may include washing with a solution such as PBS/Tween, or a borate buffer.

Following formation of specific immunocomplexes between the antigen in the test sample and the bound antigen-specific antibodies, and subsequent washing, the occurrence, and even amount, of immunocomplex formation may be determined by subjecting the immunocomplex to a second antibody having specificity for the antigen. To provide detecting means, the second antibody may have an associated activity, such as an enzymatic activity, that will generate, for example, a color development upon incubating with an appropriate chromogenic substrate. Quantification may then achieved by measuring the degree of color generation using, for example, a visible spectra spectrophotometer. In an additional embodiment, the present invention includes a diagnostic kit comprising antigen-specific antibodies generated by immunization of a host with immunogenic compositions produced according to the present invention.

In some embodiments, the present invention provides a kit comprising a composition comprising a nanoemulsion adjuvant. In some embodiments, the kit further provides a device for administering the composition. The present invention is not limited by the type of device included in the kit. In some embodiments, the device is configured for pulmonary application of the composition of the present invention (e.g., a nasal inhaler or nasal mister). In some embodiments, a kit comprises a composition comprising a nanoemulsion in a concentrated form (e.g., that can be diluted prior to administration to a subject).

In some embodiments, all kit components are present within a single container (e.g., vial or tube). In some embodiments, each kit component is located in a single container (e.g., vial or tube (e.g., a nanoemulsion adjuvant is present in one container and an immunogen is present in a second, separate container)). In some embodiments, one or more kit components are located in a single container (e.g., vial or tube) with other components of the same kit being located in a separate container (e.g., vial or tube). In some embodiments, a kit comprises a buffer. In some embodiments, the kit further comprises instructions for use.

Animal Models

In some embodiments, nanoemulsion adjuvant compositions (e.g., for generating an immune response (e.g., for use as an adjuvant and/or vaccine) are tested in animal models of infectious diseases. The use of well-developed animal models provides a method of measuring the effectiveness and safety of a vaccine before administration to human subjects. Exemplary animal models of disease are shown in Table 2. These animals are commercially available (e.g., from Jackson Laboratories Charles River; Portage, Mich.).

Animal models of *Bacillus cereus* (closely related to *Bacillus anthracis*) are utilized to test Anthrax vaccines of the present invention. Both bacteria are spore forming Gram positive rods and the disease syndrome produced by each bacteria is largely due to toxin production and the effects of these toxins on the infected host (Brown et al., J. Bact., 75:499 (1958); Burdon and Wende, J. Infect Dis., 107:224 (1960); Burdon et al., J. Infect. Dis., 117:307 (1967)). *Bacillus cereus* infection mimics the disease syndrome caused by *Bacillus anthracis*. Mice are reported to rapidly succumb to the effects of *B. cereus* toxin and are a useful model for acute infection. Guinea pigs develop a skin lesion subsequent to subcutaneous infection with *B. cereus* that resembles the cutaneous form of anthrax.

*Clostridium perfringens* infection in both mice and guinea pigs has been used as a model system for the in vivo testing of antibiotic drugs (Stevens et al., Antimicrob. Agents Chemother., 31:312 (1987); Stevens et al., J. Infect. Dis., 155:220 (1987); Alttemeier et al., Surgery, 28:621 (1950); Sandusky et al., Surgery, 28:632 (1950)). *Clostridium tetani* is well known to infect and cause disease in a variety of mammalian species. Mice, guinea pigs, and rabbits have all been used experimentally (Willis, Topley and Wilson's Principles of Bacteriology, Virology and Immunity. Wilson, G., A. Miles, and M. T. Parker, eds. pages 442-475 1983).

*Vibrio cholerae* infection has been successfully initiated in mice, guinea pigs, and rabbits. According to published reports it is preferred to alter the normal intestinal bacterial flora for the infection to be established in these experimental hosts. This is accomplished by administration of antibiotics to suppress the normal intestinal flora and, in some cases, withholding food from the animals (Butterton et al., Infect. Immun., 64:4373 (1996); Levine et al., Microbiol. Rev., 47:510 (1983); Finkelstein et al., J. Infect. Dis., 114:203 (1964); Freter, J. Exp. Med., 104:411 (1956); and Freter, J. Infect. Dis., 97:57 (1955)).

*Shigella flexnerii* infection has been successfully initiated in mice and guinea pigs. As is the case with *vibrio* infections, it is preferred that the normal intestinal bacterial flora be altered to aid in the establishment of infection in these experimental hosts. This is accomplished by administration of antibiotics to suppress the normal intestinal flora and, in some cases, withholding food from the animals (Levine et al., Microbiol. Rev., 47:510 (1983); Freter, J. Exp. Med., 104:411 (1956); Formal et al., J. Bact., 85:119 (1963); LaBrec et al., J. Bact. 88:1503 (1964); Takeuchi et al., Am. J. Pathol., 47:1011 (1965)).

Mice and rats have been used extensively in experimental studies with *Salmonella typhimurium* and *Salmonella enteriditis* (Naughton et al., J. Appl. Bact., 81:651 (1996); Carter and Collins, J. Exp. Med., 139:1189 (1974); Collins, Infect. Immun., 5:191 (1972); Collins and Carter, Infect. Immun., 6:451 (1972)).

Mice and rats are well established experimental models for infection with *Sendai* virus (Jacoby et al., Exp. Gerontol., 29:89 (1994); Massion et al., Am. J. Respir. Cell Mol. Biol. 9:361 (1993); Castleman et al., Am. J. Path., 129:277 (1987); Castleman, Am. J. Vet. Res., 44:1024 (1983); Mims and Murphy, Am. J. Path., 70:315 (1973)).

*Sindbis* virus infection of mice is usually accomplished by intracerebral inoculation of newborn mice. Alternatively, weanling mice are inoculated subcutaneously in the footpad (Johnson et al., J. Infect. Dis., 125:257 (1972); Johnson, Am. J. Path., 46:929 (1965)).

It is preferred that animals are housed for 3-5 days to rest from shipping and adapt to new housing environments before use in experiments. At the start of each experiment, control animals are sacrificed and tissue is harvested to establish baseline parameters. Animals are anesthetized by any suitable method (e.g., including, but not limited to, inhalation of Isofluorane for short procedures or ketamine/xylazine injection for longer procedure).

TABLE 2

Animal Models of Infectious Diseases

| Microorganism | Experimental Animal Species | Experimental Animal Strains | Sex | Age | Route of Infection |
|---|---|---|---|---|---|
| *Francisella philomiraga* | mice | BALB/C | M | 6 W | Intraperitoneal |
| *Neisseria meningitidis* | mice | BALB/C | F | 6-10 W | Intraperitoneal |
|  | rats | COBS/CD | M/F | 4 D | Intranasal |
| *Streptococcus pneumoniae* | mice | BALB/C | F | 6 W | Intranasal |
|  | rats | COBS/CD | M | 6-8 W | Intranasal |
|  | guinea Pigs | Hartley | M/F | 4-5 W | Intranasal |
| *Yersinia pseudotuberculosis* | mice | BALB/C | F | 6 W | Intranasal |
| *Influenza virus* | mice | BALB/C | F | 6 W | Intranasal |
| *Sendai virus* | mice | CD-1 | F | 6 W | Intranasal |
|  | rats | Sprague-Dawley | M | 6-8 W | Intranasal |
| *Sindbis* | mice | CD-1 | M/F | 1-2 D | Intracerebral/SC |
| *Vaccinia* | mice | BALB/C | F | 2-3 W | Intradermal |

Assays for Evaluation of Adjuvants and Vaccines

In some embodiments, nanoemulsion adjuvants and/or vaccines comprising the same are evaluated using one of several suitable model systems. For example, cell-mediated immune responses can be evaluated in vitro. In addition, an animal model may be used to evaluate in vivo immune response and immunity to pathogen challenge. Any suitable animal model may be utilized, including, but not limited to, those disclosed in Table 2.

Before testing a nanoemulsion vaccine in an animal system, the amount of exposure of the pathogen to a nanoemulsion sufficient to inactivate the pathogen is investigated. It is contemplated that pathogens such as bacterial spores require longer periods of time for inactivation by the nanoemulsion in order to be sufficiently neutralized to allow for immunization. The time period required for inactivation may be investigated using any suitable method, including, but not limited to, those described in the illustrative examples below.

In addition, the stability of emulsion-developed vaccines is evaluated, particularly over time and storage condition, to ensure that vaccines are effective long-term. The ability of other stabilizing materials (e.g., dendritic polymers) to enhance the stability and immunogenicity of vaccines is also evaluated.

Once a given nanoemulsion/pathogen vaccine has been formulated to result in pathogen inactivation, the ability of the vaccine to elicit an immune response and provide immunity is optimized. Non-limiting examples of methods for assaying vaccine effectiveness are described in Example 14 below. For example, the timing and dosage of the vaccine can be varied and the most effective dosage and administration schedule determined. The level of immune response is quantitated by measuring serum antibody levels. In addition, in vitro assays are used to monitor proliferation activity by measuring $H^3$-thymidine uptake. In addition to proliferation, Th1 and Th2 cytokine responses (e.g., including but not limited to, levels of include IL-2, TNF-γ, IFN-γ, IL-4, IL-6, IL-11, IL-12, etc.) are measured to qualitatively evaluate the immune response.

Finally, animal models are utilized to evaluate the effect of a nanoemulsion mucosal vaccine. Purified pathogens are mixed in emulsions (or emulsions are contact with a pre-infected animal), administered, and the immune response is determined. The level of protection is then evaluated by challenging the animal with the specific pathogen and subsequently evaluating the level of disease symptoms. The level of immunity is measured over time to determine the necessity and spacing of booster immunizations.

III. Therapeutics and Prophylactics

Furthermore, in preferred embodiments, a nanoemulsion adjuvant composition of the present invention induces (e.g., when administered to a subject) innate and adaptive/acquired immune responses (e.g., both systemic and mucosal immunity). Thus, in some preferred embodiments, administration of a composition of the present invention to a subject results in protection against an exposure (e.g., a mucosal exposure) to a pathogen. Although an understanding of the mechanism is not necessary to practice the present invention and the present invention is not limited to any particular mechanism of action, mucosal administration (e.g., vaccination) provides protection against pathogen infection (e.g., that initiates at a mucosal surface). Although it has heretofore proven difficult to stimulate secretory IgA responses and protection against pathogens that invade at mucosal surfaces (See, e.g., Mestecky et al, Mucosal Immunology. 3ed edn. (Academic Press, San Diego, 2005)), the present invention provides compositions and methods for stimulating mucosal immunity (e.g., a protective IgA response) from a pathogen in a subject.

In some embodiments, the present invention provides a composition (e.g., a composition comprising a NE and immunogenic protein antigens to serve as a mucosal vaccine. This material can easily be produced with NE and pathogen derived protein and induces both mucosal and systemic immunity. The ability to produce this formulation rapidly and administer it via mucosal (e.g., nasal or vaginal) instillation provides a vaccine that can be used in large-scale administrations (e.g., to a population of a town, village, city, state or country).

In some preferred embodiments, the present invention provides a composition for generating an immune response comprising a NE and an immunogen (e.g., a purified, isolated or synthetic protein or derivative, variant, or analogue thereof; or, one or more serotypes of pathogens inactivated by the nanoemulsion). When administered to a subject, a composition of the present invention stimulates an immune response against the immunogen/pathogen within the subject. Although an understanding of the mechanism is not necessary to practice the present invention and the present invention is not limited to any particular mechanism of action, in some embodiments, generation of an immune response (e.g., resulting from administration of a composition comprising a nanoemulsion and an immunogen) stimulates innate and/or adaptive/acquired immune responses that provides total or partial immunity to the subject (e.g., from signs, symptoms or conditions of a disease (e.g., caused by the pathogen)). Without being bound to any specific theory, protection and/or immunity from disease (e.g., the ability of a subject's immune system to prevent or attenuate (e.g., suppress) a sign, symptom or condition of disease) after exposure to an immunogenic composition of the present invention is due to adaptive (e.g., acquired) immune responses (e.g., immune responses mediated by B and T cells following exposure to a NE comprising an immunogen of the present invention (e.g., immune responses that exhibit increased specificity and reactivity towards the pathogen). Thus, in some embodiments, the compositions and methods of the present invention are used prophylactically or therapeutically to prevent or attenuate a sign, symptom or condition associated with the pathogen.

In some embodiments, a nanoemulsion adjuvant is administered alone. In some embodiments, a nanoemulsion adjuvant comprises one or more other agents (e.g., a pharmaceutically acceptable carrier, other adjuvant, excipient, and the like). In some embodiments, a nanoemulsion adjuvant is administered in a manner to induce a humoral immune response. In some embodiments, a nanoemulsion adjuvant is administered in a manner to induce a cellular (e.g., cytotoxic T lymphocyte) immune response, rather than a humoral response. In some embodiments, a nanoemulsion adjuvant induces both a cellular and humoral immune response.

The present invention is not limited by the particular formulation of a composition comprising a nanoemulsion adjuvant (e.g., independently or together with an immunogen) of the present invention. Indeed, a composition comprising a nanoemulsion adjuvant of the present invention may comprise one or more different agents in addition to the nanoemulsion adjuvant. These agents or cofactors include, but are not limited to, additional adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a composition comprising a nanoemulsion adjuvant of the present invention comprises an agent and/or co-factor that enhance the ability of the nanoemulsion adjuvant to induce an immune response. In some preferred embodiments, the presence of one or more co-factors or agents reduces the amount of nanoemulsion adjuvant required for induction of an immune response (e.g., a protective immune response (e.g., protective immunization)). In some embodiments, the presence of one or more co-factors or agents can be used to skew the immune response towards a cellular (e.g., T cell mediated) or humoral (e.g., antibody mediated) immune response. The present invention is not limited by the type of co-factor or agent used in a therapeutic agent of the present invention.

Adjuvants are described in general in Vaccine Design—the Subunit and Adjuvant Approach, edited by Powell and Newman, Plenum Press, New York, 1995. The present invention is not limited by the type of adjuvant utilized (e.g., for use in a composition (e.g., pharmaceutical composition) comprising a nanoemulsion adjuvant). For example, in some embodiments, suitable adjuvants include an aluminium salt such as aluminium hydroxide gel (alum) or aluminium phosphate. In some embodiments, an adjuvant may be a salt of calcium, iron or zinc, or may be an insoluble suspension of acylated tyrosine, or acylated sugars, cationically or anionically derivatised polysaccharides, or polyphosphazenes.

In some embodiments, a composition comprising a nanoemulsion adjuvant described herein (e.g., with or without an immunogen) comprises one or more additional adjuvants that induce and/or skew toward a Th1-type response.

In general, an immune response is generated to an antigen through the interaction of the antigen with the cells of the immune system. Immune responses may be broadly categorized into two categories: humoral and cell mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an immunogen). Immune responses can be measured in many ways including activation, proliferation or differentiation of cells of the immune system (e.g., B cells, T cells, dendritic cells, APCs, macrophages, NK cells, NKT cells etc.); upregulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

Although an understanding of the mechanism is not necessary to practice the present invention and the present invention is not limited to any particular mechanism of action, in some embodiments, compositions and methods of the present invention induce expression and secretion of cytokines (e.g., by macrophages, dendritic cells and CD4+ T cells (See, e.g., Example 8). Modulation of expression of a particular cytokine can occur locally or systemically. It is known that cytokine profiles can determine T cell regulatory and effector functions in immune responses. In some embodiments, Th1-type cytokines can be induced, and thus, the immunostimulatory compositions of the present invention can promote a Th1 type antigen-specific immune response including cytotoxic T-cells. Cytokines play a role in directing the T cell response. Helper (CD4+) T cells orchestrate the immune response of mammals through production of soluble factors that act on other immune system cells, including B and other T cells. Most mature CD4+ T helper cells express one of two cytokine profiles: Th1 or Th2. Th1-type CD4+ T cells secrete IL-2, IL-3, IFN-γ, GM-CSF and high levels of TNF-α. Th2 cells express IL-3, IL-4, IL-5, IL-6, IL-9, IL-10, IL-13, GM-CSF and low levels of TNF-α. Th1 type cytokines promote both cell-mediated immunity, and humoral immunity that is characterized by immunoglobulin class switching to IgG2a in mice and IgG1 in humans. Th1 responses may also be associated with delayed-type hypersensitivity and autoimmune disease. Th2 type cytokines induce primarily humoral immunity and induce class switching to IgG1 and IgE. The antibody isotypes associated with Th1 responses generally have neutralizing and opsonizing capabilities whereas those associated with Th2 responses are associated more with allergic responses.

Several factors have been shown to influence skewing of an immune response towards either a Th1 or Th2 type response. The best characterized regulators are cytokines. IL-12 and IFN-γ are positive Th1 and negative Th2 regulators. IL-12 promotes IFN-γ production, and IFN-γ provides positive feedback for IL-12. IL-4 and IL-10 appear important for the establishment of the Th2 cytokine profile and to down-regulate Th1 cytokine production.

Thus, in some preferred embodiments, the present invention provides a method of stimulating a Th1-type immune response in a subject comprising administering to a subject a composition comprising a nanoemulsion adjuvant described herein (e.g., with or without an immunogen).

Several other types of Th1-type immunogens can be used (e.g., as an adjuvant) in compositions and methods of the present invention. These include, but are not limited to, the following. In some embodiments, monophosphoryl lipid A (e.g., in particular 3-de-O-acylated monophosphoryl lipid A (3D-MPL)), is used. 3D-MPL is a well-known adjuvant manufactured by Ribi Immunochem, Montana. Chemically it is often supplied as a mixture of 3-de-O-acylated monophosphoryl lipid A with either 4, 5, or 6 acylated chains. In some embodiments, diphosphoryl lipid A, and 3-O-deacylated variants thereof are used. Each of these immunogens can be purified and prepared by methods described in GB 2122204B, hereby incorporated by reference in its entirety. Other purified and synthetic lipopolysaccharides have been described (See, e.g., U.S. Pat. No. 6,005,099 and EP 0 729 473; Hilgers et al., 1986, Int. Arch. Allergy. Immunol., 79(4):392-6; Hilgers et al., 1987, Immunology, 60(1):141-6; and EP 0 549 074, each of which is hereby incorporated by reference in its entirety). In some embodiments, 3D-MPL is used in the form of a particulate formulation (e.g., having a small particle size less than 0.2 μm in diameter, described in EP 0 689 454, hereby incorporated by reference in its entirety).

In some embodiments, saponins are used as an immunogen (e.g., Th1-type adjuvant) in a composition of the present invention. Saponins are well known adjuvants (See, e.g., Lacaille-Dubois and Wagner (1996) Phytomedicine vol 2 pp 363-386). Examples of saponins include Quil A (derived from the bark of the South American tree *Quillaja Saponaria* Molina), and fractions thereof (See, e.g., U.S. Pat. No. 5,057,540; Kensil, Crit Rev Ther Drug Carrier Syst, 1996, 12 (1-2):1-55; and EP 0 362 279, each of which is hereby incorporated by reference in its entirety). Also contemplated to be useful in the present invention are the haemolytic saponins QS7, QS17, and QS21 (HPLC purified fractions of Quil A; See, e.g., Kensil et al. (1991). J. Immunology 146, 431-437, U.S. Pat. No. 5,057,540; WO 96/33739; WO 96/11711 and EP 0 362 279, each of which is hereby incorporated by reference in its entirety). Also contemplated to be useful are combinations of QS21 and polysorbate or cyclodextrin (See, e.g., WO 99/10008, hereby incorporated by reference in its entirety).

In some embodiments, an immunogenic oligonucleotide containing unmethylated CpG dinucleotides ("CpG") is used as an adjuvant in the present invention. CpG is an abbreviation for cytosine-guanosine dinucleotide motifs present in DNA. CpG is known in the art as being an adjuvant when administered by both systemic and mucosal routes (See, e.g., WO 96/02555, EP 468520, Davis et al., J. Immunol, 1998, 160(2):870-876; McCluskie and Davis, J. Immunol., 1998, 161(9):4463-6; and U.S. Pat. App. No. 20050238660, each of which is hereby incorporated by reference in its entirety). For example, in some embodiments, the immunostimulatory sequence is Purine-Purine-C-G-pyrimidine-pyrimidine; wherein the CG motif is not methylated.

Although an understanding of the mechanism is not necessary to practice the present invention and the present invention is not limited to any particular mechanism of action, in some embodiments, the presence of one or more CpG oligonucleotides activate various immune subsets including natural killer cells (which produce IFN-γ) and macrophages. In some embodiments, CpG oligonucleotides are formulated into a composition of the present invention for inducing an immune response. In some embodiments, a free solution of CpG is co-administered together with an antigen (e.g., present within a NE solution (See, e.g., WO 96/02555; hereby incorporated by reference). In some embodiments, a CpG oligonucleotide is covalently conjugated to an antigen (See, e.g., WO 98/16247, hereby incorporated by reference), or formulated with a carrier such as aluminium hydroxide (See, e.g., Brazolot-Millan et al., Proc. Natl. Acad Sci., USA, 1998, 95(26), 15553-8).

In some embodiments, adjuvants such as Complete Freunds Adjuvant and Incomplete Freunds Adjuvant, cytokines (e.g., interleukins (e.g., IL-2, IFN-γ, IL-4, etc.), macrophage colony stimulating factor, tumor necrosis factor, etc.), detoxified mutants of a bacterial ADP-ribosylating toxin such as a cholera toxin (CT), a pertussis toxin (PT), or an *E. Coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (See, e.g., WO93/13202 and WO92/19265, each of which is hereby incorporated by reference), and other immunogenic substances (e.g., that enhance the effectiveness of a composition of the present invention) are used with a composition comprising a NE and immunogen of the present invention.

Additional examples of adjuvants that find use in the present invention include poly(di(carboxylatophenoxy) phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.).

Adjuvants may be added to a composition comprising a nanoemulsion adjuvant and an immunogen, or, the adjuvant may be formulated with carriers, for example liposomes, or metallic salts (e.g., aluminium salts (e.g., aluminium hydroxide)) prior to combining with or co-administration with a composition comprising a nanoemulsion adjuvant and an immunogen.

In some embodiments, a composition comprising a nanoemulsion adjuvant and an immunogen comprises a single additional adjuvant. In other embodiments, a composition comprising a nanoemulsion adjuvant and an immunogen comprises two or more additional adjuvants (See, e.g., WO 94/00153; WO 95/17210; WO 96/33739; WO 98/56414; WO 99/12565; WO 99/11241; and WO 94/00153, each of which is hereby incorporated by reference in its entirety).

In some embodiments, a composition comprising a NE adjuvant described herein (e.g., with or without an immunogen) of the present invention comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives are contemplated to be useful in the present invention including, but not limited to, cross-linked derivatives of poly(acrylic acid) (e.g., carbopol and polycarbophil), polyvinyl alcohol, polyvinyl pyrrolidone, polysaccharides (e.g., alginate and chitosan), hydroxypropyl methylcellulose, lectins, fimbrial proteins, and carboxymethylcellulose. In some embodiments, one or more components of the NE adjuvant function as a mucoadhesive (e.g., individually, or in combination with other components of the NE adjuvant). Although an understanding of the mechanism is not necessary to practice the present invention and the present invention is not limited to any particular mechanism of action, in some embodiments, use of a mucoadhesive (e.g., in a composition comprising a NE and immunogen) enhances induction of an immune response (e.g., an innate and/or adaptive immune response) in a subject (e.g., a subject administered a composition of the present invention) due to an increase in duration and/or amount of exposure to NE adjuvant and/or immunogen that a subject experiences when a mucoadhesive is used compared to the duration and/or amount of exposure to an immunogen in the absence of using the mucoadhesive).

In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, subcutaneous, intramuscular, intraperitoneal, intravenous, or administration via other routes may be found in Remington's Pharmaceutical Sciences, Mack Publishing Company, Easton, Pa.

A composition comprising a nanoemulsion adjuvant and an immunogen of the present invention can be used therapeutically (e.g., to enhance an immune response) or as a prophylactic (e.g., for immunization (e.g., to prevent signs or symptoms of disease)). A composition comprising a nanoemulsion adjuvant and an immunogen of the present invention can be administered to a subject via a number of different delivery routes and methods.

For example, the compositions of the present invention can be administered to a subject (e.g., mucosally (e.g., nasal mucosa, vaginal mucosa, etc.)) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal surface); being placed on or impregnated onto a nasal and/or vaginal applicator and applied; being applied by a controlled-release mechanism; being applied as a liposome; or being applied on a polymer.

In some preferred embodiments, compositions of the present invention are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal, pulmonary, vaginal and rectal techniques), as well as European Publication No. 517,565 and Illum et al., J. Controlled Rel., 1994, 29:133-141 (e.g., for techniques of intranasal administration), each of which is hereby incorporated by reference in its entirety). Alternatively, the compositions of the present invention may be administered dermally or transdermally, using standard techniques (See, e.g., Remington: The Science arid Practice of Pharmacy, Mack Publishing Company, Easton, Pa., 19th edition, 1995). The present invention is not limited by the route of administration.

In some embodiments, a composition comprising a nanoemulsion adjuvant and an immunogen of the present invention may be used to protect or treat a subject susceptible to, or suffering from, disease by means of administering a composition of the present invention via a mucosal route (e.g., an oral/alimentary or nasal route). Alternative mucosal routes include intravaginal and intra-rectal routes. In preferred embodiments of the present invention, a nasal route of administration is used, termed "intranasal administration" or "intranasal vaccination" herein. Methods of intranasal vaccination are well known in the art, including the administration of a droplet or spray form of the vaccine into the nasopharynx of a subject to be immunized. In some embodiments, a nebulized or aerosolized composition comprising a nanoemulsion adjuvant and immunogen is provided. Enteric formulations such as gastro resistant capsules for oral administration, suppositories for rectal or vaginal administration also form part of this invention. Compositions of the present invention may also be administered via the oral route. Under these circumstances, a composition comprising a nanoemulsion adjuvant and an immunogen may comprise a pharmaceutically acceptable excipient and/or include alkaline buffers, or enteric capsules. Formulations for nasal delivery may include those with dextran or cyclodextran and saponin as an adjuvant.

Compositions of the present invention may also be administered via a vaginal route. In such cases, a composition comprising a nanoemulsion adjuvant and an immunogen may comprise pharmaceutically acceptable excipients and/or emulsifiers, polymers (e.g., CARBOPOL), and other known stabilizers of vaginal creams and suppositories. In some embodiments, compositions of the present invention are administered via a rectal route. In such cases, a composition comprising a NE and an immunogen may comprise excipients and/or waxes and polymers known in the art for forming rectal suppositories.

In some embodiments, the same route of administration (e.g., mucosal administration) is chosen for both a priming and boosting vaccination. In some embodiments, multiple routes of administration are utilized (e.g., at the same time, or, alternatively, sequentially) in order to stimulate an immune response (e.g., using a composition comprising a nanoemulsion adjuvant and immunogen of the present invention).

For example, in some embodiments, a composition comprising a nanoemulsion adjuvant and an immunogen is administered to a mucosal surface of a subject in either a priming or boosting vaccination regime. Alternatively, in some embodiments, a composition comprising a nanoemulsion adjuvant and an immunogen is administered systemically in either a priming or boosting vaccination regime. In some embodiments, a composition comprising a nanoemulsion adjuvant and an immunogen is administered to a subject in a priming vaccination regimen via mucosal administration and a boosting regimen via systemic administration. In some embodiments, a composition comprising a nanoemulsion adjuvant and an immunogen is administered to a subject in a priming vaccination regimen via systemic administration and a boosting regimen via mucosal administration. Examples of systemic routes of administration include, but are not limited to, a parenteral, intramuscular, intradermal, transdermal, subcutaneous, intraperitoneal or intravenous administration. A composition comprising a NE and an immunogen may be used for both prophylactic and therapeutic purposes.

Thus, in some embodiments, a composition comprising a nanoemulsion adjuvant of the present invention may be used to protect and/or treat a subject susceptible to, or suffering from, a disease by means of administering a compositions comprising a nanoemulsion adjuvant by mucosal, intramuscular, intraperitoneal, intradermal, transdermal, pulmonary, intravenous, subcutaneous or other route of administration described herein. Methods of systemic administration of the adjuvant preparations may include conventional syringes and needles, or devices designed for ballistic delivery of solid vaccines (See, e.g., WO 99/27961, hereby incorporated by reference), or needleless pressure liquid jet device (See, e.g., U.S. Pat. Nos. 4,596,556; 5,993,412, each of which are hereby incorporated by reference), or transdermal patches (See, e.g., WO 97/48440; WO 98/28037, each of which are hereby incorporated by reference). The present invention may also be used to enhance the immunogenicity of antigens applied to the skin (transdermal or transcutaneous delivery, See, e.g., WO 98/20734; WO 98/28037, each of which are hereby incorporated by reference). Thus, in some embodiments, the present invention provides a delivery device for systemic administration, pre-filled with the adjuvant composition of the present invention.

In some embodiments, it is expected that each dose (e.g., of a composition comprising a nanoemulsion adjuvant and an immunogen (e.g., administered to a subject to induce an immune response (e.g., a protective immune response (e.g., protective immunity))) comprises 0.05-5000 μg of each immunogen (e.g., recombinant and/or purified protein), in some embodiments, each dose will comprise 1-500 μg, in some embodiments, each dose will comprise 350-750 μg, in some embodiments, each dose will comprise 50-200 μg, in some embodiments, each dose will comprise 25-75 μg of immunogen (e.g., recombinant and/or purified protein). In some embodiments, each dose comprises an amount of the immunogen sufficient to generate an immune response. An effective amount of the immunogen in a dose need not be quantified, as long as the amount of immunogen generates an immune response in a subject when administered to the subject. An optimal amount for a particular administration (e.g., to induce an immune response (e.g., a protective immune response (e.g., protective immunity))) can be ascertained by one of skill in the art using standard studies involving observation of antibody titers and other responses in subjects.

In some embodiments, it is expected that each dose (e.g., of a composition comprising a nanoemulsion adjuvant and an immunogen (e.g., administered to a subject to induce and immune response)) is from 0.001 to 15% or more (e.g., 0.001-10%, 0.5-5%, 1-3%, 2%, 6%, 10%, 15% or more) by weight immunogen (e.g., neutralized bacteria or virus, or recombinant and/or purified protein). In some embodiments, an initial or prime administration dose contains more immunogen than a subsequent boost dose In some embodiments, a composition comprising a nanoemulsion adjuvant of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising about 0.1-50% of the nanoemulsion adjuvant present in the concentrated composition. In some preferred embodiments, a subject is administered in a single dose a composition comprising 1% of the NE and immunogen present in the concentrated composition. Concentrated compositions are contemplated to be useful in a setting in which large numbers of subjects may be administered a composition of the present invention (e.g., an immunization clinic, hospital, school, etc.). In some embodiments, a composition comprising a nanoemulsion adjuvant of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

Generally, the emulsion compositions of the invention will comprise at least 0.001% to 100%, preferably 0.01 to 90%, of emulsion per ml of liquid composition. It is envisioned that the formulations may comprise about 0.001%, about 0.0025%, about 0.005%, about 0.0075%, about 0.01%, about 0.025%, about 0.05%, about 0.075%, about 0.1%, about 0.25%, about 0.5%, about 1.0%, about 2.5%, about 5%, about 7.5%, about 10%, about 12.5%, about 15%, about 20%, about 25%, about 30%, about 35%, about 40%, about 50%, about 55%, about 60%, about 65%, about 70%, about 75%, about 80%, about 85%, about 90%, about 95% or about 100% of emulsion per ml of liquid composition. It should be understood that a range between any two figures listed above is specifically contemplated to be encompassed within the metes and bounds of the present invention. Some variation in dosage will necessarily occur depending on the condition of the specific pathogen and the subject being immunized.

In some embodiments, following an initial administration of a composition of the present invention (e.g., an initial vaccination), a subject may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eighth, ninth, tenth, and/or more than tenth administration. Although an understanding of the mechanism is not necessary to practice the present invention and the present invention is not limited to any particular mechanism of action, in some embodiments, reintroduction of an immunogen in a boost dose enables vigorous systemic immunity in a subject. The boost can be with the same formulation given for the primary immune response, or can be with a different formulation that contains the immunogen. The dosage regimen will also, at least in part, be determined by the need of the subject and be dependent on the judgment of a practitioner.

Dosage units may be proportionately increased or decreased based on several factors including, but not limited to, the weight, age, and health status of the subject. In addition, dosage units may be increased or decreased for subsequent administrations (e.g., boost administrations).

A composition comprising an immunogen of the present invention finds use where the nature of the infectious and/or disease causing agent (e.g., for which protective immunity is sought to be elicited) is known, as well as where the nature of the infectious and/or disease causing agent is unknown (e.g., in emerging disease (e.g., of pandemic proportion (e.g., influenza or other outbreaks of disease))). For example, the present invention contemplates use of the compositions of the present invention in treatment of or prevention of infections associated with an emergent infectious and/or disease causing agent yet to be identified (e.g., isolated and/or cultured from a diseased person but without genetic, biochemical or other characterization of the infectious and/or disease causing agent).

EXAMPLES

The following examples serve to illustrate certain preferred embodiments and aspects of the present invention and are not to be construed as limiting the scope thereof.

Example 1

Th2 immune responses are characterized by the production of IgE antibodies and high levels of Th2 cytokines and are associated with inadequate protection against some pathogens as well as cancer, colitis, asthma and allergy. Most currently used vaccine adjuvants induce predominantly Th2 response. Immunotherapies that have been attempted to shift immune responses from Th2 to Th1 have generally required prolonged administration/immunization protocols and have not induced long-lasting Th1 responses. Accordingly, experiments were performed during development of embodiments of the invention in order to assess the ability of various nanoemulsion adjuvants to modulate existing Th2 polarized immune responses (e.g., in the context of allergy, inflammatory disease and other Th2 mediated disease) and shift and/or skew the Th2 polarized response towards a balanced Th1/Th17/Th2 profile (e.g., in order to reduce or eliminate signs, symptoms or morbidity associated with Th2 mediated disease).

Several different animal models were analyzed. In one model, an immunization schedule was developed in order to induce a Th2 polarized immune response directed at hepatitis B surface antigen (HBsAg). The immunization schedule is shown in FIG. 1. Mice were immunized with of 20 µg hepatitis B surface antigen (HBsAg) intramuscularly (IM) or intranasally (IN) as shown in FIG. 1, either absorbed on aluminum hydroxide (Alum) or formulated in 20% nanoemulsion (NE). The NE utilized (W805EC, described herein) contained oil, water, ethanol, polysorbate (TWEEN) 80, and cetylpyridinium chloride (CPC). Alum-adjuvanted vaccines were administered IM while NE-based vaccines were administered IN. Serum IgG subclass titers were measured by HBsAg-specific ELISA at time of sacrifice.

Figure 2:
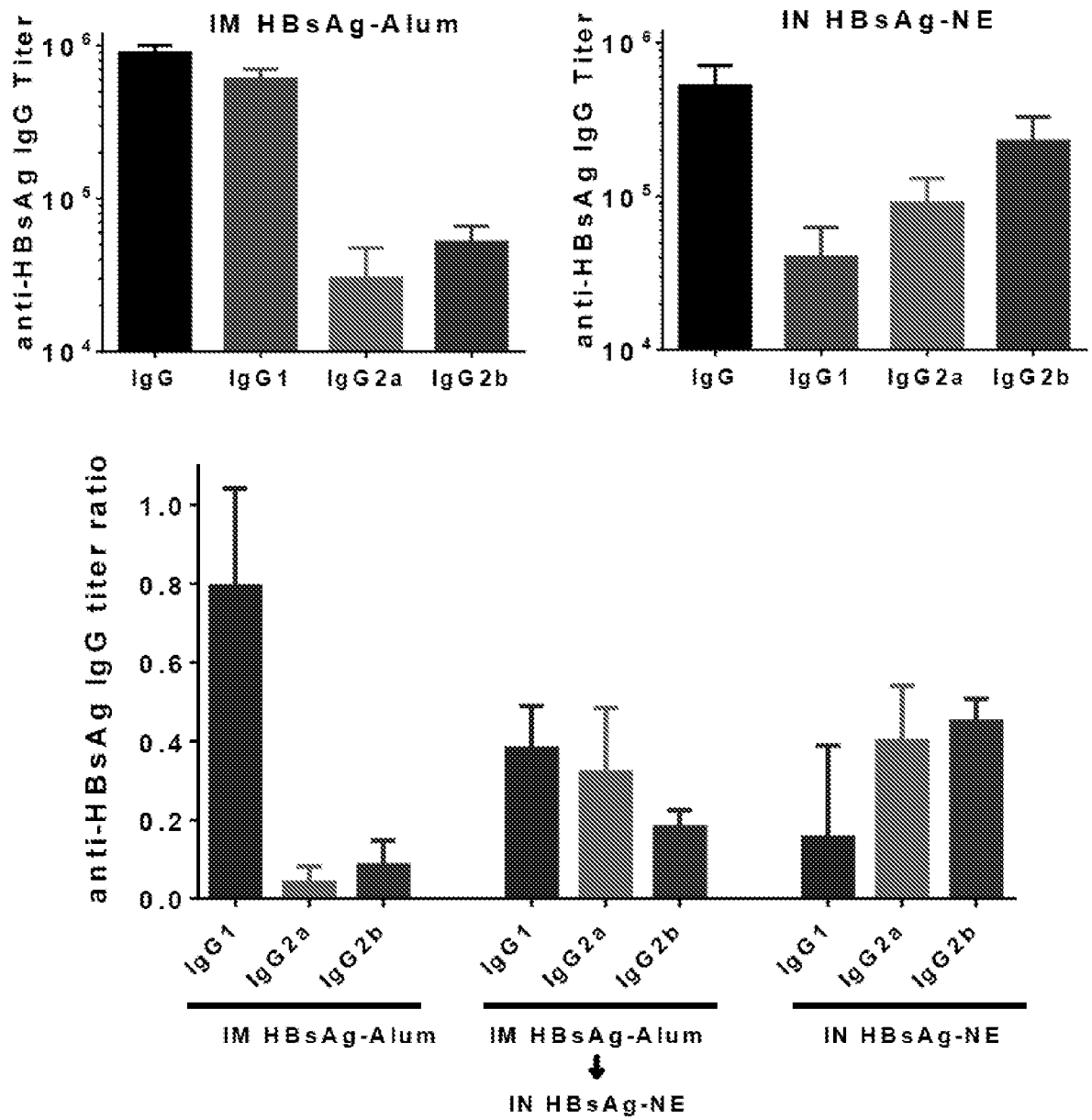
FIG. 2 shows the modification of serum antibody responses obtained using NE-based vaccine.
Figure 3:
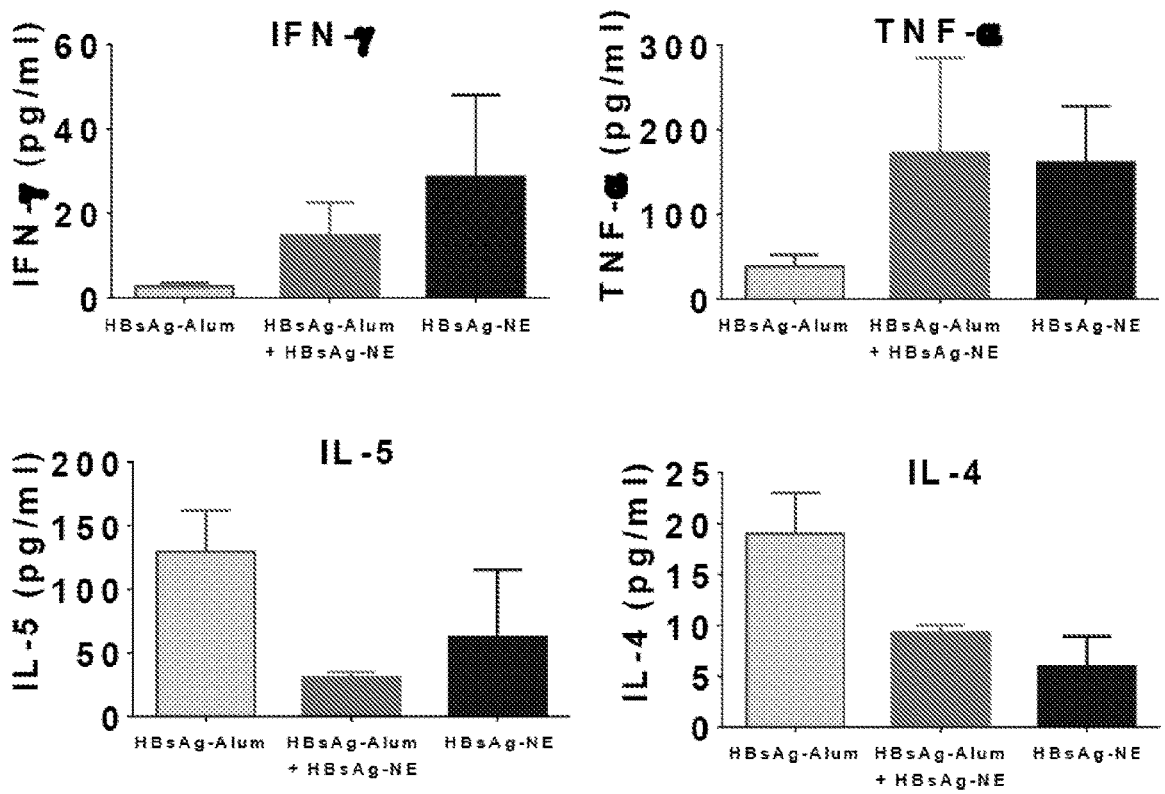
FIG. 3 shows that intranasal immunization with NE adjuvant increased production of Th1 type cytokines. Splenocytes were obtained from mice 12 weeks after initial immunization and were stimulated with 5 µg/ml HBsAg. Cytokine secretion was measured by Luminex.

As shown in FIG. 2 and FIG. 3, IM administration of Alum-adjuvanted vaccine induced strong Th2 cytokine expression and robust expression of IgG1 antibodies. IN administration of NE-based vaccine induced a Th1 type immune response marked by strong expression of Th1 cytokine expression and significant expression of IgG2a and IgG2b antibodies.

However, as shown in FIG. 1., when mice were administered alum-adjuvanted HBsAg at day 0 and week 1 in order to establish a Th2 immune response, but subsequently administered NE-based vaccine at week 7, the NE-based vaccine redirected the established Th2 polarized immune response toward a Th1 immune response, resulting in a balanced Th1/Th2 immune response (See FIG. 2 and FIG. 3). Accordingly, a Th2 immune response established by intramuscular immunization with alum-adjuvanted hepatitis B surface antigen (HBs) could be modulated by a single subsequent IN immunization with NE-HBs, resulting in increased Th1 associated immune responses (IFN-gamma, TNF-alpha, IgG2a, and IgG2b) and IL-17, while decreasing Th2 cytokines (IL-4 and IL-5) and IgG1.

Example 2

Because NE-based vaccine displayed the ability to modulate the Th2 immune response established by intramuscular immunization with alum-adjuvanted hepatitis B surface antigen (HBs), further experiments were conducted during development of embodiments of the invention in order to determine if NE-based vaccine might also be able to modulate robust Th2 mediated immune responses associated with allergic disease (e.g., allergic hyper-responsiveness/hypersensitivity).

Figure 4:
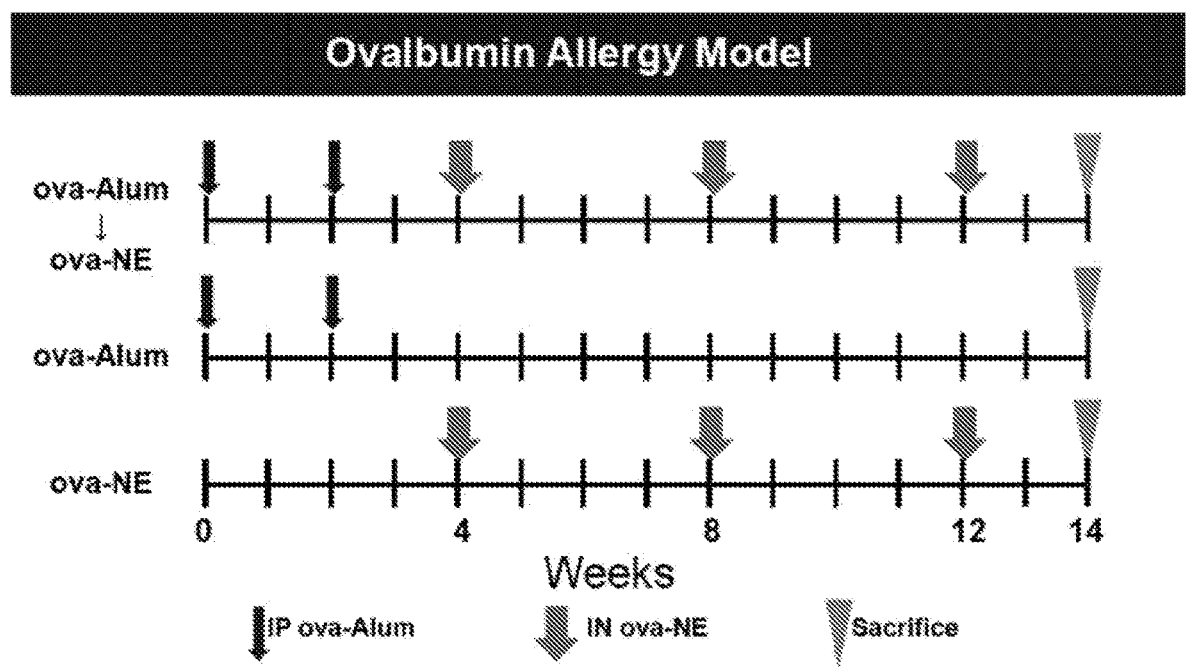
FIG. 4 shows an immunization schedule developed during experiments conducted during development of embodiments of the invention of an ovalbumin allergy model of Th2 mediated disease.

A mouse model of allergic hypersensitivity to ovalbumin was used. Mice were immunized with 20 µg ovalbumin (ova), either absorbed on aluminum hydroxide (alum) or formulated in 20% W805EC nanoemulsion (NE), as shown in FIG. 4. Alum-adjuvanted vaccines were administered IP while NE-based vaccines were administered IN. Change to say Serum IgG subclass, IgE, and IgA titers, as well as IgA in the bronchoalveolar lavage (BAL), were measured by ova-specific ELISA.

Figure 5:
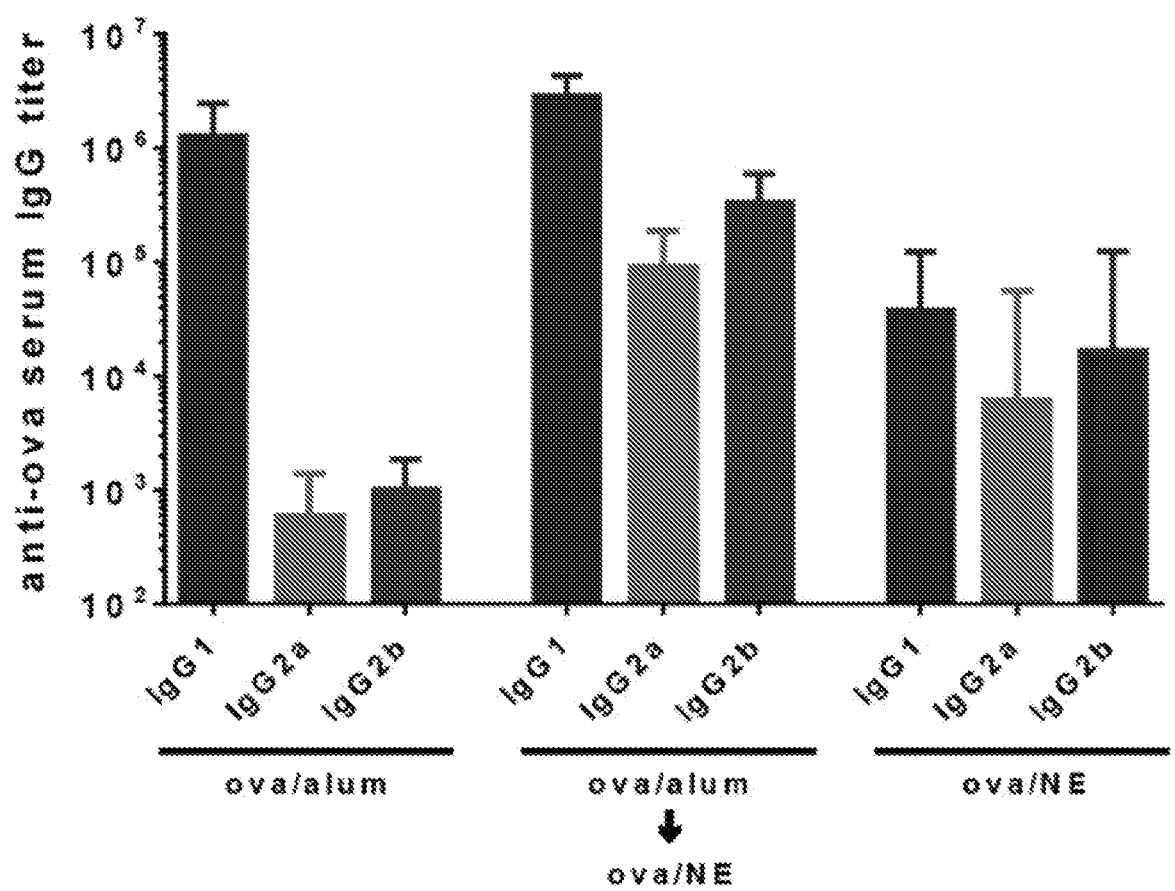
FIG. 5 shows the modification of serum antibody response with NE-based vaccine in the ovalbumin allergy model of Th2 mediated disease.
Figure 6:
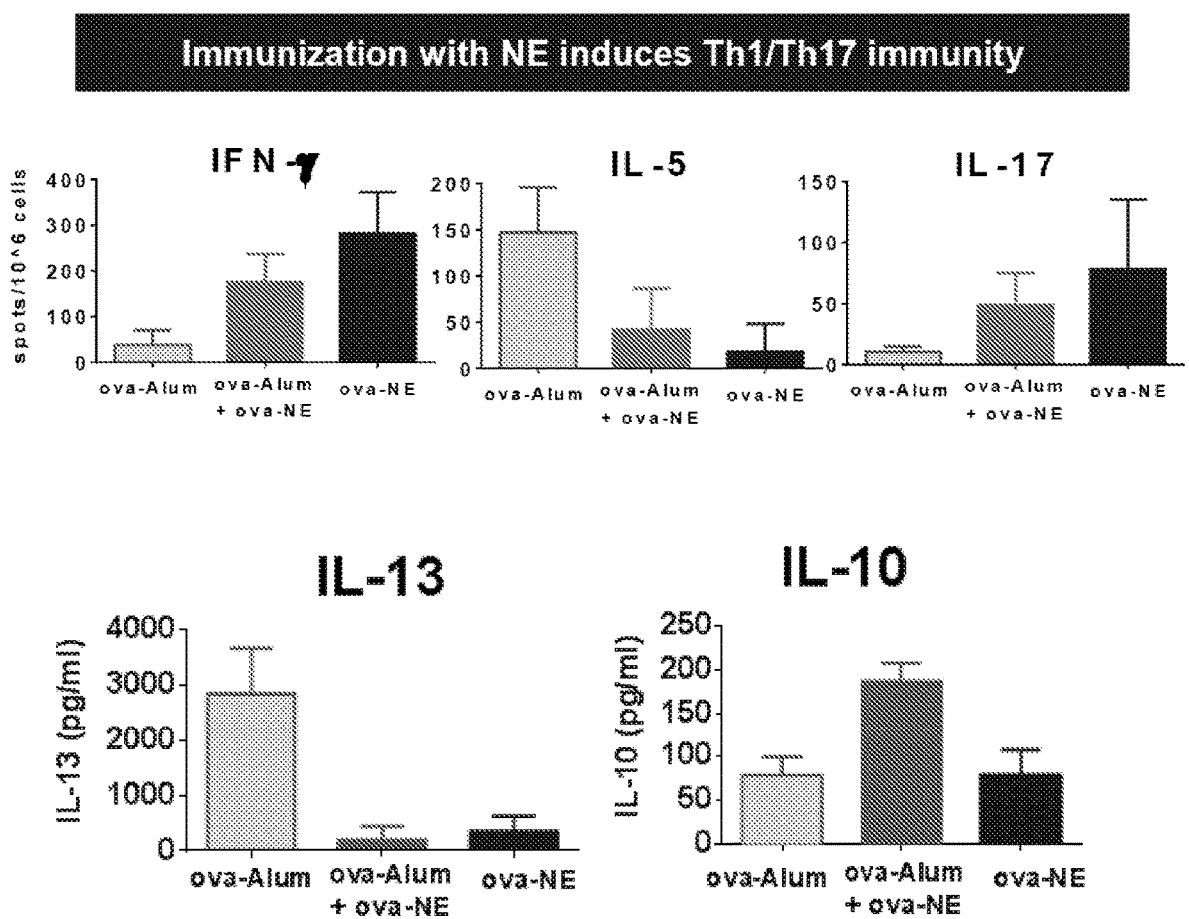
FIG. 6 shows that intranasal immunization with NE-based vaccine decreased number of lymphocytes secreting Th2 cytokines, and increased Th1 and Th17 cells. Splenocytes were obtained from mice 14 weeks after initial immunization and were stimulated with 5 µg/ml ovalbumin. Number of cytokine secreting cells was determined by ELISpot.
Figure 7:
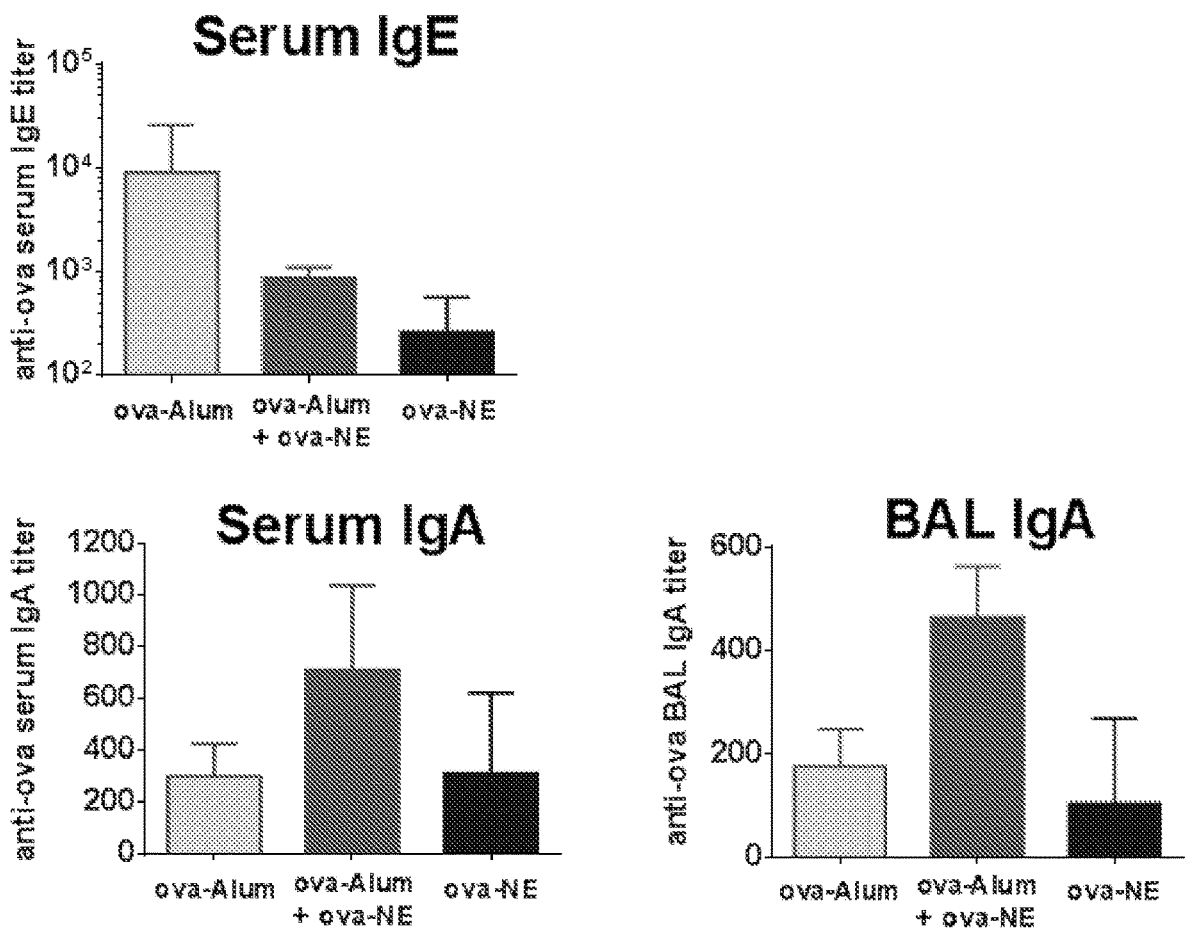
FIG. 7 shows that IP administration of Alum-adjuvanted OVA vaccine induced strong Th2 cytokine expression and robust expression of IgG1 antibodies.

As shown in FIG. 5, FIG. 6, and FIG. 7, IP administration of Alum-adjuvanted OVA vaccine induced strong Th2 cytokine expression and robust expression of IgG1 antibodies. IN administration of NE-based vaccine induced balanced Th1/Th2 type immune response marked by strong expression of Th1 cytokine expression and significant expression of IgG2a, IgG2b, and IgE antibodies.

However, when mice were administered alum-adjuvanted OVA in order to establish a Th2 immune response, but subsequently administered NE-based vaccine, the NE-based vaccine significantly modulated the established Th2 polarized immune response toward a Th1 immune response, resulting in a balanced Th1/Th2 immune response (See FIG. 5 and FIG. 6). The ability of the NE-based vaccine to alter allergic disease associated, robust Th2 immune responses was surprising as other trials described in the literature attempting to do so have failed. Yet, data accumulated using the OVA allergy model clearly indicates the ability of IN immunization with NE-based vaccine to modulate the allergic response away from the disease associated Th2 response (characterized by robust expression of Th2 cytokines (IL-4, IL-5, and IL-13) and IgG1) and toward a balanced Th1/Th2 response (characterized by reduced IgE and Th2 response and increased IFN-gamma, TNF-alpha, IgG2a, IgG2b, IgA, IL-10, and IL-17.

Figure 8:
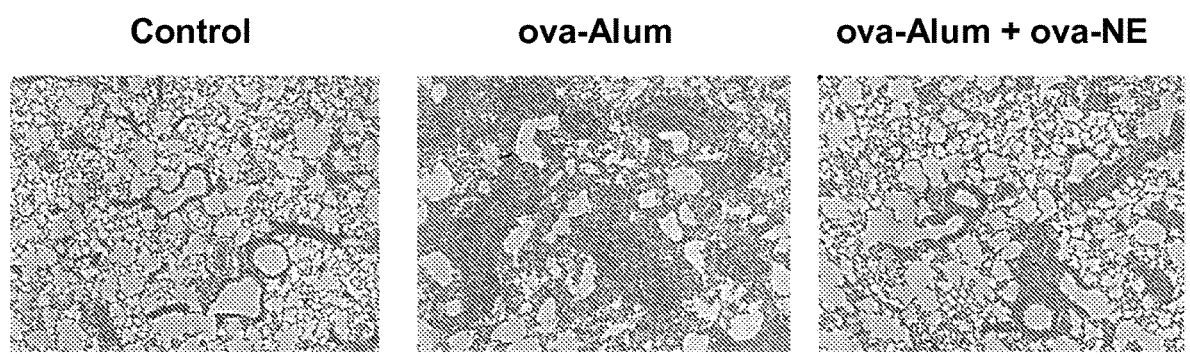
FIG. 8 shows prevention of inflammation in mice receiving therapeutic NE-OVA vaccine.
Figure 9:
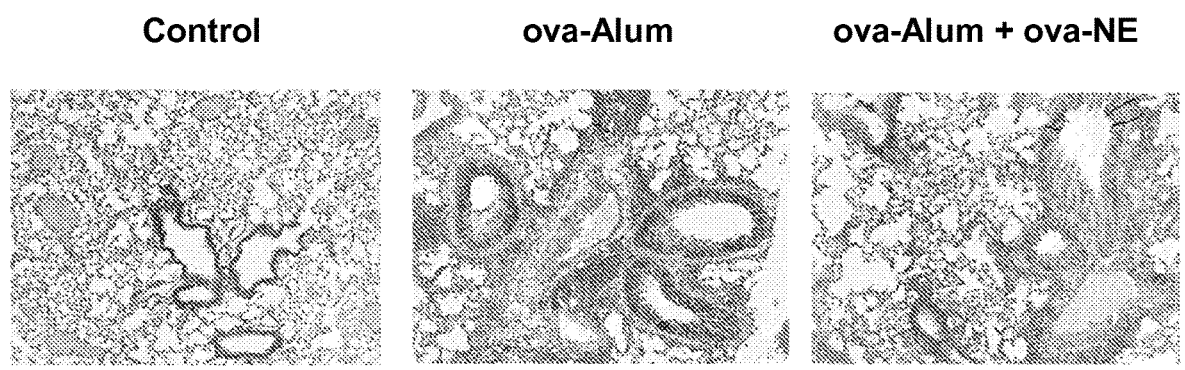
FIGS. 9A and B show prevention of mucus production in mice receiving therapeutic NE-OVA vaccine.
Figure 9:
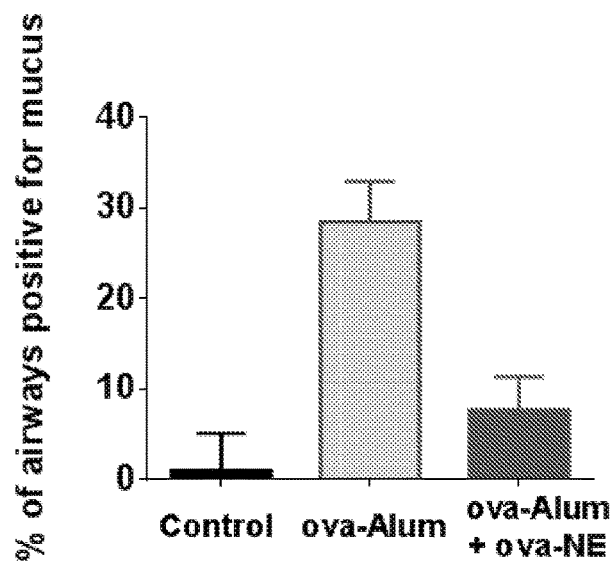

In order to determine protection against development of an allergic response, mice were subjected to an inhalation challenge with OVA. Histopathological analyses of lung tissue was used to assess inflammation and mucus production (See FIG. 8 and FIG. 9). Hematoxylin and eosin staining of lung sections revealed massive mononuclear cell inflammation in the lungs of mice sensitized with the IP Alum-adjuvanted OVA, and this inflammation was largely prevented in mice receiving the therapeutic NE-OVA vaccine. There was a similar prevention of mucus production by the NE vaccine as measured by periodic acid Schiff staining of lung sections, as shown in FIG. 9. Mice receiving the therapeutic NE vaccine had significant reductions in both the severity and percentage of airways producing mucus. These data clearly demonstrate that therapeutic immunization with IN NE-based vaccine protect sensitized mice from developing an allergic response upon exposure to the OVA allergen.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

What is claimed is:

1. A method for treating an allergic reaction to a peanut allergen in a subject, which comprises intranasally administering to the subject a therapeutically effective amount of an immunogenic composition comprising a peanut allergen and a nanoemulsion, wherein:
   (a) the subject has an established Th2 polarized immune response prior to administering the immunogenic composition; and
   (b) the nanoemulsion comprises oil, water, ethanol, a polysorbate surfactant and a cationic compound, whereupon the allergic reaction is treated.

2. The method of claim 1, wherein administering the immunogenic composition to the subject increases the expression of Th1 type cytokines in the subject.

3. The method of claim 2, wherein the Th1 type cytokine is IFN-gamma.

4. The method of claim 2, wherein the Th1 type cytokine is TNF-alpha.

5. The method of claim 2, wherein the Th1 type cytokine is IL-17.

6. The method of claim 1, wherein administering the immunogenic composition to the subject increases Th17 immunity.

7. The method of claim 1, wherein the nanoemulsion comprises a positive surface charge.

8. The method of claim 1, wherein the cationic compound is cetylpyridinium chloride (CPC).

9. The method of claim 1, wherein the nanoemulsion comprises oil, water, ethanol, polysorbate 80 and CPC.

10. The method of claim 1, wherein administering the immunogenic composition to the subject induces antigen-specific IL-10 expression in the subject.

11. The method of claim 1, wherein hypersensitivity to the peanut allergen is decreased in the subject upon subsequent exposure to the peanut allergen.

* * * * *